United States Patent [19]
Collins et al.

[11] Patent Number: 6,165,715
[45] Date of Patent: Dec. 26, 2000

[54] EXPRESSION SYSTEMS

[75] Inventors: Mary Katherine Levinge Collins; Robin Anthony Weiss; Yasuhiro Takeuchi, all of London, United Kingdom; Francois-Lois Cosset, Lyons, France

[73] Assignee: Cancer Research Campaign Technology Limited, United Kingdom

[21] Appl. No.: 09/011,745

[22] PCT Filed: Aug. 23, 1996

[86] PCT No.: PCT/GB96/02061

§ 371 Date: Jun. 22, 1998

§ 102(e) Date: Jun. 22, 1998

[87] PCT Pub. No.: WO97/08330

PCT Pub. Date: Mar. 6, 1997

[30] Foreign Application Priority Data

Aug. 23, 1995 [GB] United Kingdom .................. 9517263

[51] Int. Cl.[7] ................ C12Q 1/68; C12N 5/10; C12N 15/86; C12N 15/63

[52] U.S. Cl. ............... 435/6; 435/69.1; 435/320.1; 435/325; 435/455; 435/456; 435/371; 435/366; 435/354; 435/372.1; 536/23.1; 536/24.1

[58] Field of Search ................ 435/69.1, 320.1, 435/325, 455, 456, 371, 366, 354, 372.1, 6; 536/23.1, 24.1

*Primary Examiner*—David Guzo
*Attorney, Agent, or Firm*—Dann, Dorfman, Herrell and Skillman

[57] ABSTRACT

The invention relates to new expression systems and in particular to an expression system in which a gene of interest is expressed at an optimal level. The invention provides a recombinant expression vector comprising a gene of interest and a selectable marker gene, wherein the selectable marker gene is arranged downstream of the gene of interest and a stop codon associated with the gene of interest is spaced from a start codon of said selectable marker gene at a distance which is sufficient to ensure that translation reinitiation is required before said selectable marker protein is expressed from the corresponding mRNA. Examples of such expression systems are vector viral packaging cell lines and a number of preferred cell lines have been identified.

35 Claims, 22 Drawing Sheets

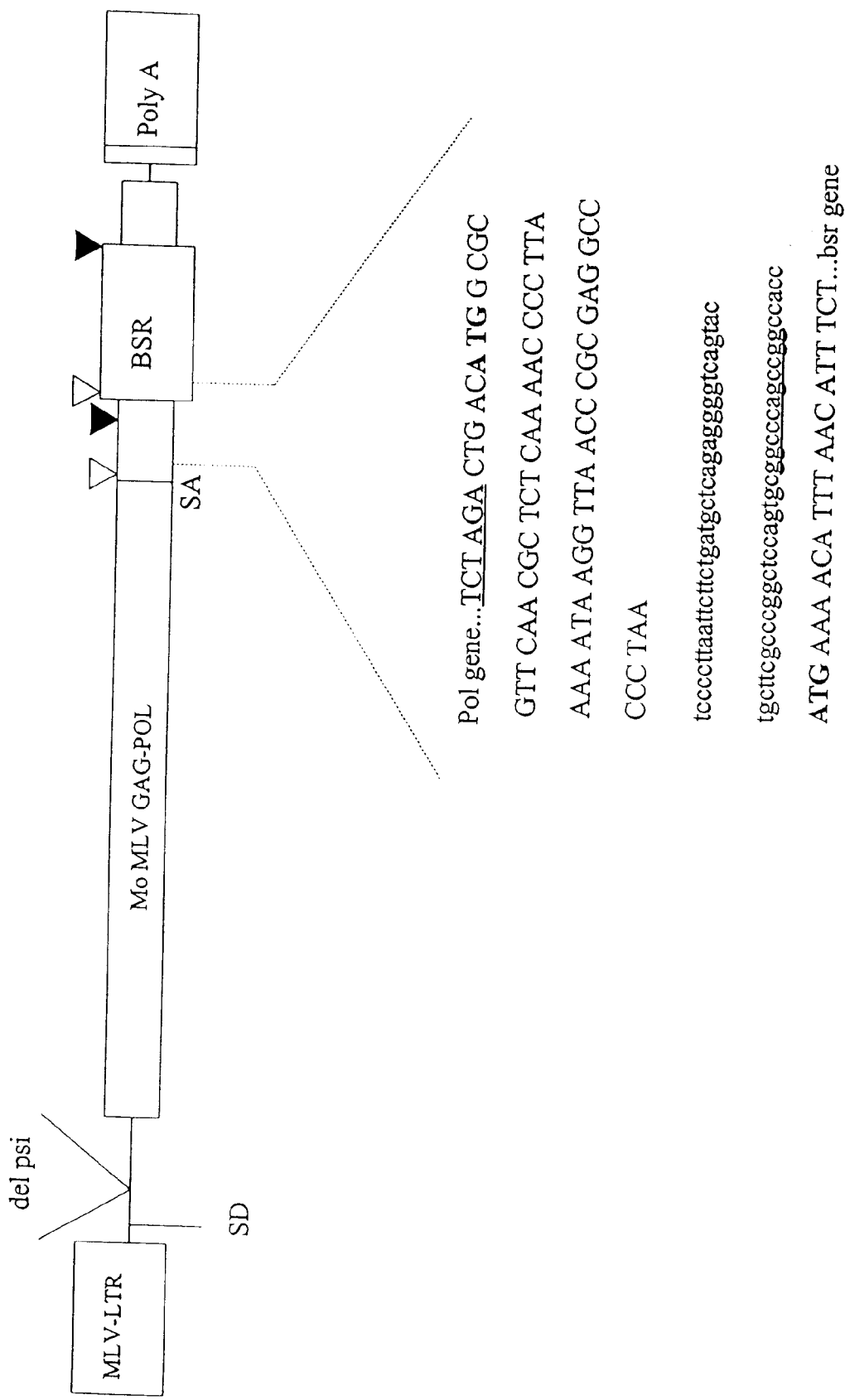
Figure 1. Schematic structure of CeB expression vector

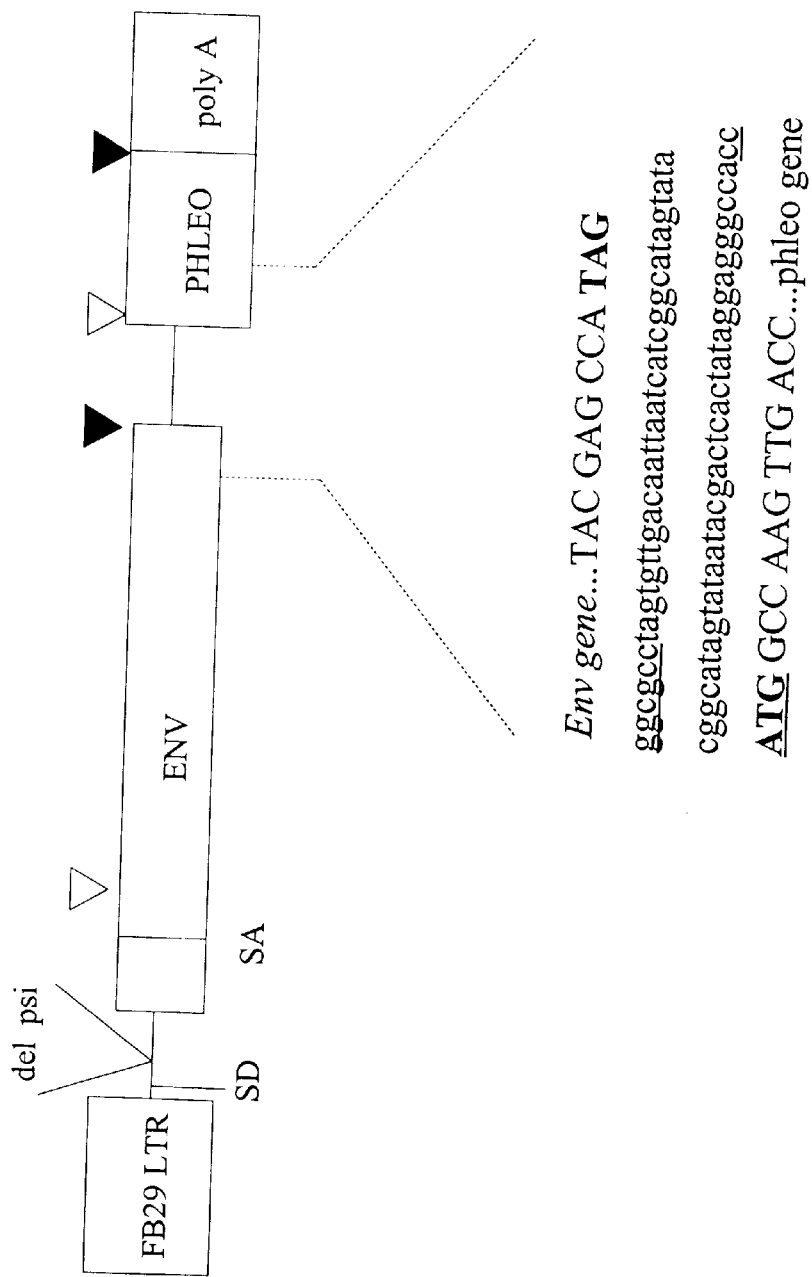
Figure 2. Schematic structure of FbdelPASF expression vector

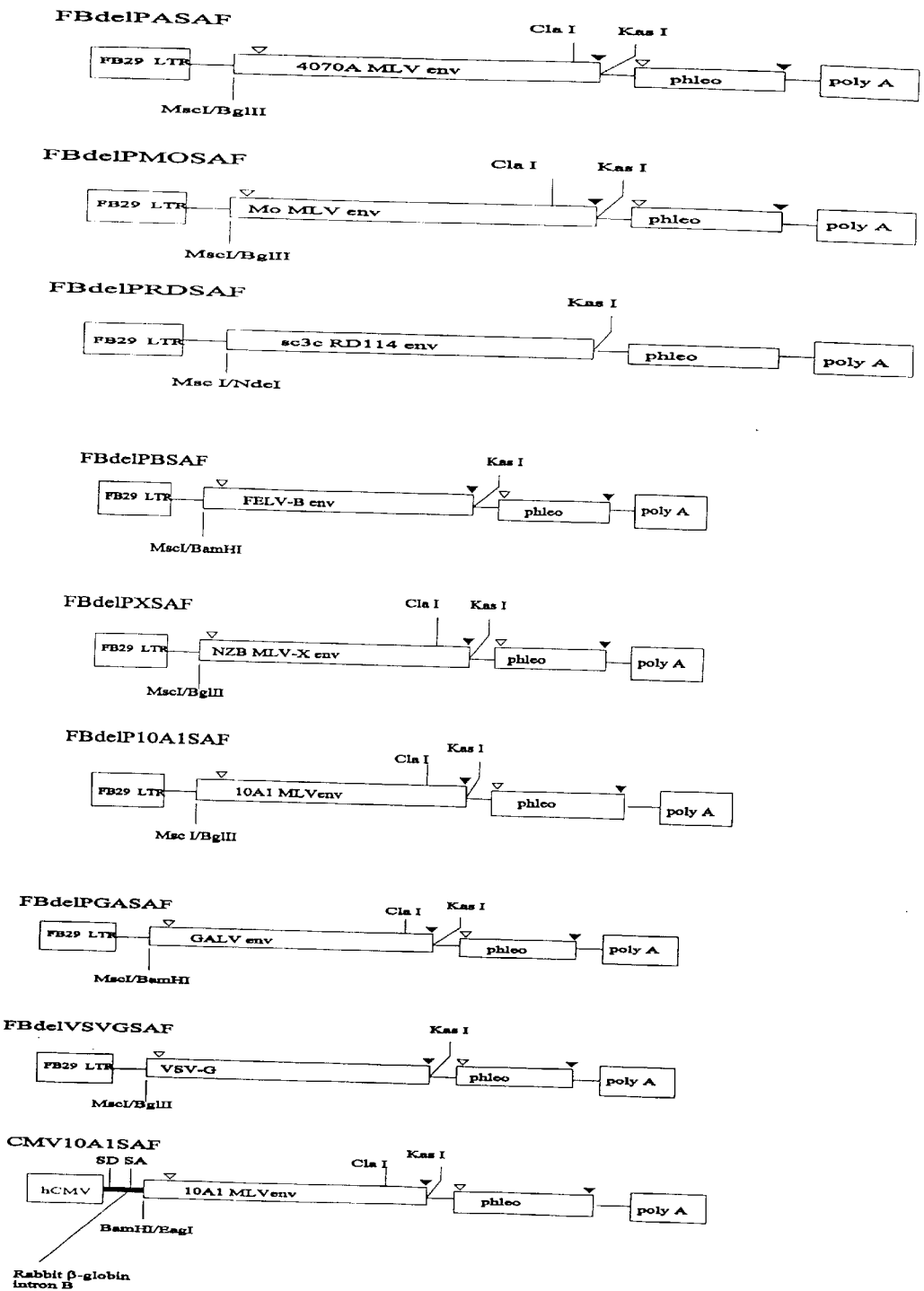
Figure 3. Schematic structure of env expression vectors

```
NGAGCTCAGGACAGGTAGAAAGAATGAATAGAACAATAAAAGAGACCCTTACTAAATTGA   60
CCTTAGAGACTGGCTTAAAAGATTGGAGACGCCTCCTATCTCTGGCTTTGTTAAGAGCCA  120
GAAATACGCCCAACCGTTTTCGGCTCACCCCATATGAAATCCTTTATGGGGACCCCCCC   180
CTTTGTCAACCTTGCTCAATTCCTTCTCCCCCTCCGATCCTAAGACTGATTTACAAGCCC  240
GACTAAAAGGGCTGCAAGGCGTGCAGGCCCAAATCTGGACACCCCTGGCCGAATTGTACC  300
GGCCAGGACATCCACAAACTAGCCACCCATTTCAGGTGGGAGACTCCGTGTACGTCCGGC  360
GGCACCGCTCTCAAGGATTGGAGCCTCGTTGGAAGGGACCTTACATCGTCCTGCTGACCA  420
CGCCCACCGCCATAAAGGTTGACGGGATCGCCGCCTGGATTCACGCATCGCACGCCAAGG  480
CAGCCCCAAAAACCCCTGGACCAGAAACTCCCAAAACCTGGAAGCTCCGCCGTTCGGAGA  540
ACCCTCTTAAGATAAGACTCTCCCGTGTCTGACTGCTAATCCACCTTGTCCCTGTACTAA  600
CCCAAAATGAAACTCCCAACAGGAATGGTCATTTTATGTAGCCTAATAATAGTTCGGGCA  660
GGGTTTGACGACCCCGCAAGGCTATCGCATTAGTACAAAAACAACATGGTAAACCATGC   720
GAATGCAGCGGAGGGCAGGTATCCGAGGCCCCACCGAACTCCATCCAACAGGTAACTTGC  780
CCAGGCAAGACGGCCTACTTAATGACCAACCAAAAATGGAAATGCAGAGTCACTCCAAAA  840
ATCTCACCTAGCGGGGAGAACTCCAGAACTGCCCCTGTAACACTTTCCAGGACTCGATG   900
CACAGTTCTTGTTATACTGAATACCGGCAATGCAGGCGAATTAATAAGACATACTACACG  960
GCCACCTTGCTTAAAATACGGTCTGGGAGCCTCAACGAGGTACAGATATTACAAAACCCC 1020
AATCAGCTCCTACAGTCCCCTTGTAGGGGCTCTATAAATCAGCCCGTTTGCTGGAGTGCC 1080
ACAGCCCCCATCCATATCTCCGATGGTGGAGGACCCCTCGATACTAAGAGAGTGTGGACA 1140
GTCCAAAAAGGCTAGAACAAATTCATAAGGCTATGACTCCTGAACTTCAATACCACCCC  1200
TTAGCCCTGCCCAAAGTCAGAGATGACCTTAGCCTTGATGCACGGACTTTTGATATCCTG 1260
AATACCACTTTTAGGTTACTCCAGATGTCCAATTTTAGCCTTGCCCAAGATTGTTGGCTC 1320
TGTTTAAAACTAGGTACCCCTACCCCTCTTGCGATACCCACTCCCTCTTTAACCTACTCC 1380
CTAGCAGACTCCCTAGCGAATGCCTCCTGTCAGATTATACCTCCCCTCTTGGTTCAACCG 1440
ATGCAGTTCTCCAACTCGTCCTGTTTATCTTCCCCTTTCATTAACGATACGGAACAAATA 1500
GACTTAGGTGCAGTCACCTTTACTAACTGCACCTCTGTAGCCAATGTCAGTAGTCCTTTA 1560
TGTGCCCTAAACGGGTCAGTCTTCCTCTGTGGAAATAACATGGCATACACCTATTTACCC 1620
CAAAACTGGACCAGACTTTGCGTCCAAGCCTCCCTCCTCCCCGACATTGACATCAACCCG 1680
GGGGATGAGCCAGTCCCCATTCCTGCCATTGATCATTATATACATAGACCTAAACGAGCT 1740
GTACAGTTCATCCCTTTACTAGCTGGACTGGGAATCACCGCAGCATTCACCACCGGAGCT 1800
ACAGGCCTAGGTGTCTCCGTCACCCAGTATACAAAATTATCCCATCAGTTAATATCTGAT 1860
GTCCAAGTCTTATCCGGTACCATACAAGATTTACAAGACCAGGTAGACTCGTTAGCTGAA 1920
GTAGTTCTCCAAAATAGGAGGGGACTGGACCTACTAACGGCAGAACAAGGAGGAATTTGT 1980
TTAGCCTTACAAGAAAATGCTGTTTTATGCTAACAAGTCAGGAATTGTGAGAAACAAA   2040
ATAAGAACCCTACAAGAAGAATTACAAAAACGCAGGGAAAGCCTGGCAACCAACCCTCTC 2100
TGGACCGGGCTGCAGGGCTTTCTTCCGTACCTCCTACCTCTCCTGGGACCCCTACTCACC 2160
CTCCTACTCATACTAACCATTGGGCCATGCGTTTTCAGTCGCCTCATGGCCTTCATTAAT 2220
GATAGACTTAATGTTGTACATGCCATGGTGCTGGCCCAGCAATACCAAGCACTCAAAGCT 2280
GAGGAAGAAGCTCAGGATTGAGCTTCCGGGACAAAAGCAGGGGGAATGAGAAGTCAGAA  2340
CCCCCCACCTTTGCTACATAAATAACCGCTTTCATTTCGCTTCTGTAAAACGCTTATGCG 2400
CCCCACCCTAGCCGGAAAGTCCCCAGCCGCTACGCAACCCGGGCCCCGAGTTGCATCAGC 2460
CGTTCGCAACCCGGGCTCCGAGTTGCATCAGCCGAAAGAAACTTCATTTCCCAAGCTT   2518
```

Fig.4

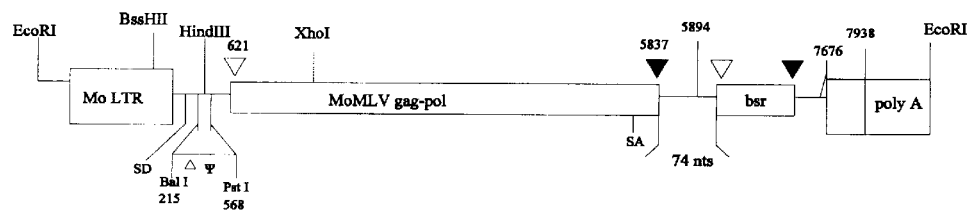
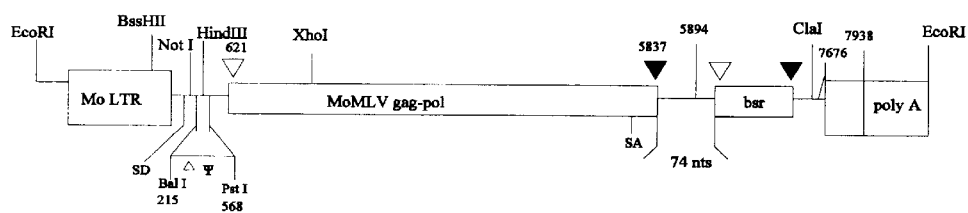
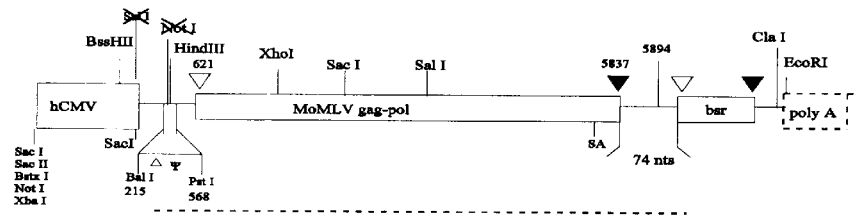
Figure 5. Genetic structure of gag-pol constructs (page 1/3)

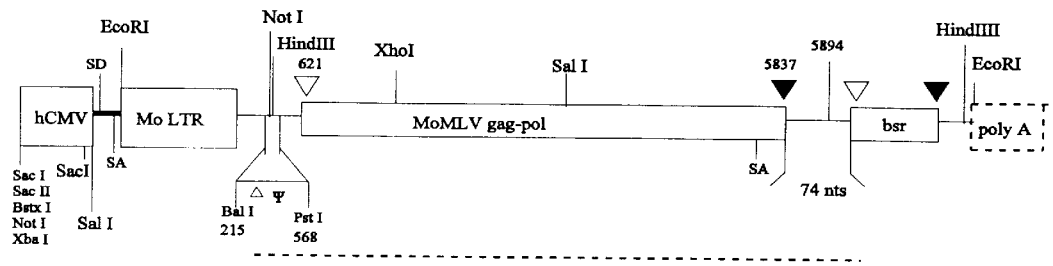
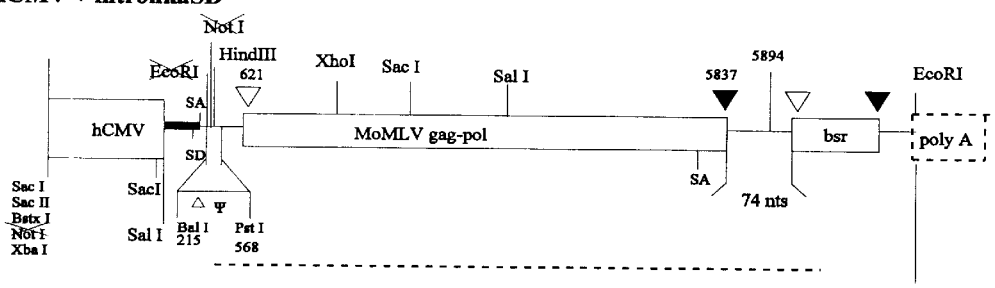
Figure 5. Genetic structure of gal-pol constructs (page 2/3)

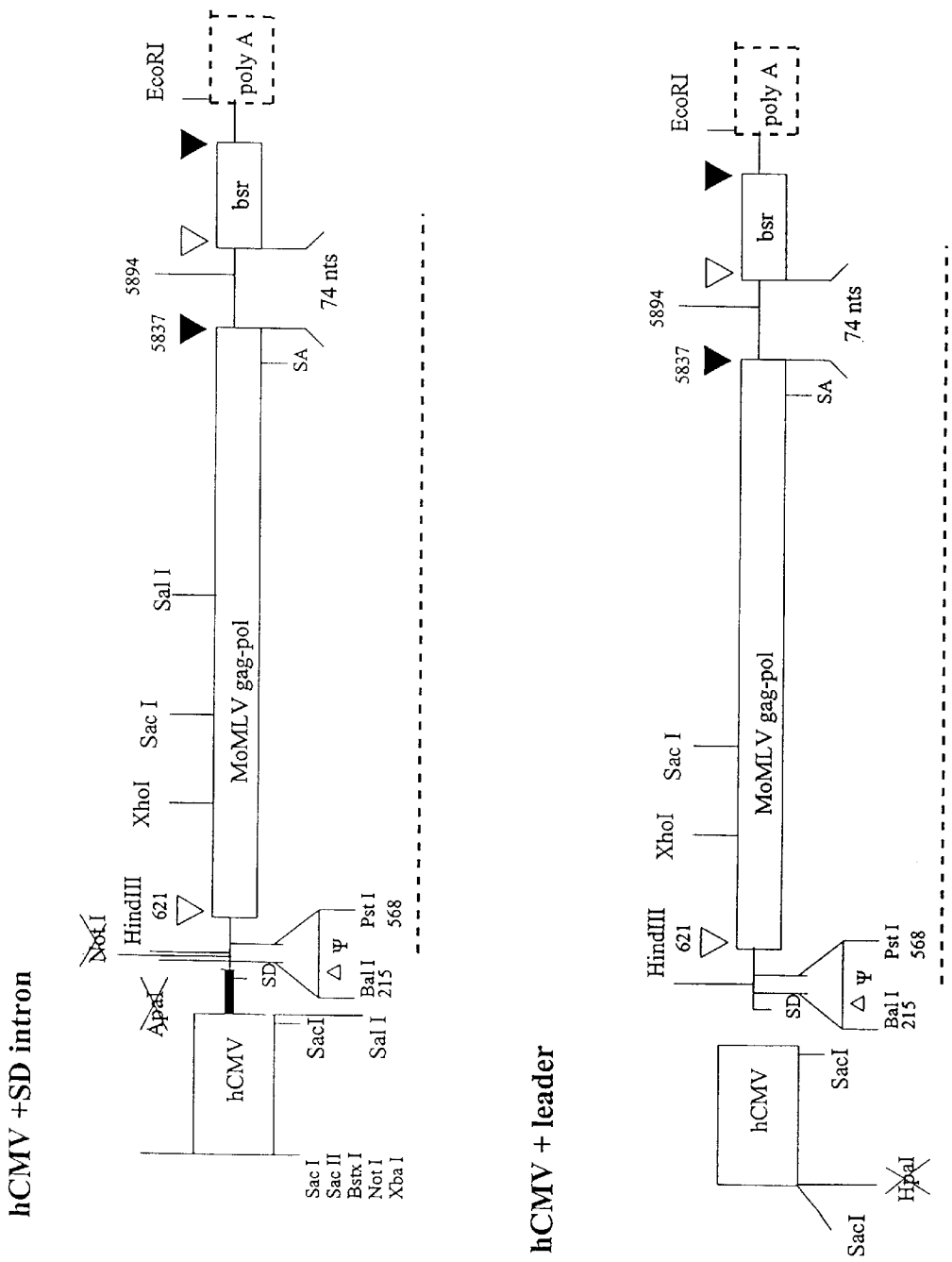
Figure 5. Genetic Structure of gag-pol constructs (page 3/3)

Figure 6a. CeB Sequence

```
AATGAAAGAC CCCACCTGTA GGTTTGGCAA GCTAGCTTAA GTAACGCCAT TTTGCAAGGC    60
ATGGAAAAAT ACATAACTGA GAATAGAGAA GTTCAGATCA AGGTCAGGAA CAGATGGAAC   120
AGCTGAATAT GGGCCAAACA GGATATCTGT GGTAAGCAGT TCCTGCCCCG GCTCAGGGCC   180
AAGAACAGAT GGAACAGCTG AATATGGGCC AAACAGGATA TCTGTGGTAA GCAGTTCCTG   240
CCCCGGCTCA GGGCCAAGAA CAGATGGTCC CCAGATGCGG TCCAGCCCTC AGCAGTTTCT   300
AGAGAACCAT CAGATGTTTC CAGGGTGCCC CAAGGACCTG AAATGACCCT GTGCCTTATT   360
TGAACTAACC AATCAGTTCG CTTCTCGCTT CTGTTCGCGC GCTTCTGCTC CCCGAGCTCA   420
ATAAAAGAGC CCACAACCCC TCACTCGGGG CGCCAGTCCT CCGATTGACT GAGTCGCCCG   480
GGTACCCGTG TATCCAATAA ACCCTCTTGC AGTTGCATCC GACTTGTGGT CTCGCTGTTC   540
CTTGGGAGGG TCTCCTCTGA GTGATTGACT ACCCGTCAGC GGGGGTCTTT CATTTGGGGG   600
CTCGTCCGGG ATCGGGAGAC CCCTGCCCAG GGACCACCGA CCCACCACCG GGAGGTAAGC   660
TGGAAGCTTC TGCAGCATCG TTCTGTGTTG TCTCTGTCTG ACTGTGTTTC TGTATTTGTC   720
TGAGAATATG GGCCAGACTG TTACCACTCC CTTAAGTTTG ACCTTAGGTC ACTGGAAAGA   780
TGTCGAGCGG ATCGCTCACA ACCAGTCGGT AGATGTCAAG AAGAGACGTT GGGTTACCTT   840
CTGCTCTGCA GAATGGCCAA CCTTTAACGT CGGATGGCCG CGAGACGGCA CCTTTAACCG   900
AGACCTCATC ACCCAGGTTA AGATCAAGGT CTTTTCACCT GGCCCGCATG GACACCCAGA   960
CCAGGTCCCC TACATCGTGA CCTGGGAAGC CTTGGCTTTT GACCCCCCTC CCTGGGTCAA  1020
GCCCTTTGTA CACCCTAAGC CTCCGCCTCC TCTTCCTCCA TCCGCCCCGT CTCTCCCCCT  1080
TGAACCTCCT CGTTCGACCC CGCCTCGATC CTCCCTTTAT CCAGCCCTCA CTCCTTCTCT  1140
AGGCGCCAAA CCTAAACCTC AAGTTCTTTC TGACAGTGGG GGGCCGCTCA TCGACCTACT  1200
TACAGAAGAC CCCCCGCCTT ATAGGGACCC AAGACCACCC CCTTCCGACA GGGACGGAAA  1260
TGGTGGAGAA GCGACCCCTG CGGGAGAGGC ACCGGACCCC TCCCAATGG CATCTCGCCT   1320
ACGTGGGAGA CGGGAGCCCC CTGTGGCCGA CTCCACTACC TCGCAGGCAT TCCCCCTCCG  1380
CGCAGGAGGA AACGGACAGC TTCAATACTG GCCGTTCTCC TCTTCTGACC TTTACAACTG  1440
GAAAAATAAT AACCCTTCTT TTTCTGAAGA TCCAGGTAAA CTGACAGCTC TGATCGAGTC  1500
TGTTCTCATC ACCCATCAGC CCACCTGGGA CGACTGTCAG CAGCTGTTGG GGACTCTGCT  1560
GACCGGAGAA GAAAAACAAC GGGTGCTCTT AGAGGCTAGA AAGGCGGTGC GGGGCGATGA  1620
TGGGCGCCCC ACTCAACTGC CCAATGAAGT CGATGCCGCT TTTCCCCTCG AGCGCCCAGA  1680
CTGGGATTAC ACCACCCAGG CAGGTAGGAA CCACCTAGTC CACTATCGCC AGTTGCTCCT  1740
AGCGGGTCTC CAAAACGCGG GCAGAAGCCC CACCAATTTG GCCAAGGTAA AAGGAATAAC  1800
ACAAGGGCCC AATGAGTCTC CCTCGGCCTT CCTAGAGAGA CTTAAGGAAG CCTATCGCAG  1860
GTACACTCCT TATGACCCTG AGGACCCAGG GCAAGAAACT AATGTGTCTA TGTCTTTCAT  1920
TTGGCAGTCT GCCCCAGACA TTGGGAGAAA GTTAGAGAGG TTAGAAGATT TAAAAAACAA  1980
GACGCTTGGA GATTTGGTTA GAGAGGCAGA AAAGATCTTT AATAAACGAG AAACCCCGGA  2040
AGAAAGAGAG GAACGTATCA GGAGAGAAAC AGAGGAAAAA GAAGAACGCC GTAGGACAGA  2100
GGATGAGCAG AAAGAGAAAG AAAGAGATCG TAGGAGACAT AGAGAGATGA GCAAGCTATT  2160
GGCCACTGTC GTTAGTGGAC AGAAACAGGA TAGACAGGGA GGAGAACGAA GGAGGTCCCA  2220
ACTCGATCGC GACCAGTGTG CCTACTGCAA AGAAAAGGGG CACTGGGCTA AAGATTGTCC  2280
CAAGAAACCA CGAGGACCTC GGGGACCAAG ACCCCAGACC TCCCTCCTGA CCCTAGATGA  2340
CTAGGGAGGT CAGGGTCAGG AGCCCCCCCC TGAACCCAGG ATAACCCTCA AAGTCGGGGG  2400
GCAACCCGTC ACCTTCCTGG TAGATACTGG GGCCCAACAC TCCGTGCTGA CCCAAAATCC  2460
TGGACCCCTA AGTGATAAGT CTGCCTGGGT CCAAGGGGCT ACTGGAGGAA AGCGGTATCG  2520
CTGGACCACG GATCGCAAAG TACATCTAGC TACCGGTAAG GTCACCCACT CTTTCCTCCA  2580
TGTACCAGAC TGTCCCTATC CTCTGTTAGG AAGAGATTTG CTGACTAAAC TAAAAGCCCA  2640
AATCCACTTT GAGGGATCAG GAGCTCAGGT TATGGGACCA ATGGGGCAGC CCCTGCAAGT  2700
GTTGACCCTA AATATAGAAG ATGAGCATCG GCTACATGAG ACCTCAAAAG AGCCAGATGT  2760
TTCTCTAGGG TCCACATGGC TGTCTGATTT TCCTCAGGCC TGGGCGGAAA CCGGGGGCAT  2820
GGGACTGGCA GTTCGCCAAG CTCCTCTGAT CATACCTCTG AAAGCAACCT CTACCCCCGT  2880
GTCCATAAAA CAATACCCCA TGTCACAAGA AGCCAGACTG GGATCAAGC CCCACATACA   2940
GAGACTGTTG GACCAGGGAA TACTGGTACC CTGCCAGTCC CCTGGAACA CGCCCCTGCT   3000
ACCCGTTAAG AAACCAGGGA CTAATGATTA TAGGCCTGTC CAGGATCTGA GAGAAGTCAA  3060
CAAGCGGGTG GAAGACATCC ACCCCACCGT GCCCAACCCT TACAACCTCT TGAGCGGGCT  3120
CCCACCGTCC CACCAGTGGT ACACTGTGCT TGATTTAAAG GATGCCTTTT TCTGCCTGAG  3180
ACTCCACCCC ACCAGTCAGC TCTCTTCGC CTTTGAGTGG AGAGATCCAG AGATGGGAAT   3240
CTCAGGACAA TTGACCTGGA CCAGACTCCC ACAGGGTTTC AAAAACAGTC CCACCCTGTT  3300
TGATGAGGCA CTGCACAGAG ACCTAGCAGA CTTCCGGATC CAGCACCCAG ACTTGATCCT  3360
GCTACAGTAC GTGGATGACT TACTGCTGGC CGCCACTTCT GAGCTAGACT GCCAACAAGG  3420
TACTCGGGCC CTGTTACAAA CCCTAGGGAA CCTCGGGTAT CGGGCCTCGG CCAAGAAAGC  3480
CCAAATTTGC CAGAAACAGG TCAAGTATCT GGGGTATCTT CTAAAAGAGG GTCAGAGATG  3540
GCTGACTGAG GCCAGAAAAG AGACTGTGAT GGGGCAGCCT ACTCCGAAGA CCCCTCGACA  3600
ACTAAGGGAG TTCCTAGGGA CGGCAGGCTT CTGTCGCCTC TGGATCCCTG GGTTTGCAGA  3660
AATGGCAGCC CCCTTGTACC CTCTCACCAA AACGGGGACT CTGTTTAATT GGGGCCCAGA  3720
CCAACAAAAG GCCTATCAAG AAATCAAGCA AGCTCTTCTA ACTGCCCCAG CCCTGGGGTT  3780
GCCAGATTTG ACTAAGCCCT TTGAACTCTT TGTCGACGAG AAGCAGGGCT ACGCCAAAGG  3840
TGTCCTAACG CAAAAACTGG GACCTTGGCG TCGGCCGGTG GCCTACCTGT CCAAAAAGCT  3900
AGACCCAGTA GCAGCTGGGT GGCCCCCTTG CCTACGGATG GTAGCAGCCA TTGCCGTACT  3960
GACAAAGGAT GCAGGCAAGC TAACCATGGG ACAGCCACTA GTCATTCTGG CCCCCCATGC  4020
AGTAGAGGCA CTAGTCAAAC AACCCCCCGA CCGCTGGCTT TCCAACGCCC GGATGACTCA  4080
```

Figure 6b. CeB Sequence

```
CTATCAGGCC TTGCTTTTGG ACACGGACCG GGTCCAGTTC GGACCGGTGG TAGCCCTGAA     4140
CCCGGCTACG CTGCTCCCAC TGCCTGAGGA AGGGCTGCAA CACAACTGCC TTGATATCCT     4200
GGCCGAAGCC CACGGAACCC GACCCGACCT AACGGACCAG CCGCTCCCAG ACGCCGACCA     4260
CACCTGGTAC ACGGATGGAA GCAGTCTCTT ACAAGAGGGA CAGCGTAAGG CGGGAGCTGC     4320
GGTGACCACC GAGACCGAGG TAATCTGGGC TAAAGCCCTG CCAGCCGGGA CATCCGCTCA     4380
GCGGGCTGAA CTGATAGCAC TCACCCAGGC CCTAAAGATG GCAGAAGGTA AGAAGCTAAA     4440
TGTTTATACT GATAGCCGTT ATGCTTTTGC TACTGCCCAT ATCCATGGAG AAATATACAG     4500
AAGGCGTGGG TTGCTCACAT CAGAAGGCAA AGAGATCAAA AATAAAGACG AGATCTTGGC     4560
CCTACTAAAA GCCCTCTTTC TGCCCAAAAG ACTTAGCATA ATCCATTGTC CAGGACATCA     4620
AAAGGGACAC AGCGCCGAGG CTAGAGGCAA CCGGATGGCT GACCAAGCGG CCCGAAAGGC     4680
AGCCATCACA GAGACTCCAG ACACCTCTAC CCTCCTCATA GAAAATTCAT CACCCTACAC     4740
CTCAGAACAT TTTCATTACA CAGTGACTGA TATAAAGGAC CTAACCAAGT TGGGGGCCAT     4800
TTATGATAAA ACAAAGAAGT ATTGGGTCTA CCAAGGAAAA CCTGTGATGC CTGACCAGTT     4860
TACTTTTGAA TTATTAGACT TTCTTCATCA GCTGACTCAC CTCAGCTTCT CAAAAATGAA     4920
GGCTCTCCTA GAGAGAAGCC ACAGTCCCTA CTACATGCTG AACCGGGATC GAACACTCAA     4980
AAATATCACT GAGACCTGCA AAGCTTGTGC ACAAGTCAAC GCCAGCAAGT CTGCCGTTAA     5040
ACAGGGAACT AGGGTCCGCG GGCATCGGCC CGGCACTCAT TGGGAGATCG ATTTCACCGA     5100
GATAAAGCCC GGATTGTATG GCTATAAATA TCTTCTAGTT TTTATAGATA CCTTTTCTGG     5160
CTGGATAGAA GCCTTCCCAA CCAAGAAAGA AACCGCCAAG GTCGTAACCA AGAAGCTACT     5220
AGAGGAGATC TTCCCCAGGT TCGGCATGCC TCAGGTATTG GGAACTGACA ATGGGCCTGC     5280
CTTCGTCTCC AAGGTGAGTC AGACAGTGGC CGATCTGTTG GGGATTGATT GGAAATTACA     5340
TTGTGCATAC AGACCCCAAA GCTCAGGCCA GGTAGAAAGA ATGAATAGAA CCATCAAGGA     5400
GACTTTAACT AAATTAACGC TTGCAACTGG CTCTAGAGAC TGGGTGCTCC TACTCCCCTT     5460
AGCCCTGTAC CGAGCCCGCA ACACGCCGGG CCCCCATGGC CTCACCCCAT ATGAGATCTT     5520
ATATGGGGCA CCCCCGCCCC TTGTAAACTT CCCTGACCCT GACATGACAA GAGTTACTAA     5580
CAGCCCCTCT CTCCAAGCTC ACTTACAGGC TCTCTACTTA GTCCAGCACG AAGTCTGGAG     5640
ACCTCTGGCG GCAGCCTACC AAGAACAACT GGACCGACCG GTGGTACCTC ACCCTTACCG     5700
AGTCGGCGAC ACAGTGTGGG TCCGCCGACA CCAGACTAAG AACCTAGAAC CTCGCTGGAA     5760
AGGACCTTAC ACAGTCCTGC TGACCACCCC CACCGCCCTC AAAGTAGACG GCATCGCAGC     5820
TTGGATACAC GCCGCCACG TGAAGGCTGC CGACCCCGGG GGTGGACCAT CCTCTAGACT     5880
GACATGGCGC GTTCAACGCT CTCAAAACCC CTTAAAAATA AGGTTAACCC GCGAGGCCCC     5940
CTAATCCCCT TAATTCTTCT GATGCTCAGA GGGGTCAGTA CTGCTTCGCC CGGCTCCAGT     6000
GCGGCCCAGC CGGCCACCAT GAAAACATTT AACATTTCTC AACAAGATCT AGAATTAGTA     6060
GAAGTAGCGA CAGAGAAGAT TACAATGCTT TATGAGGATA ATAAACATCA TGTGGGAGCG     6120
GCAATTCGTA CGAAAACAGG AGAAATCATT TCGGCAGTAC ATATTGAAGC GTATATAGGA     6180
CGAGTAACTG TTTGTGCAGA AGCCATTGCG ATTGGTAGTG CAGTTTCGAA TGGACAAAAG     6240
GATTTTGACA CGATTGTAGC TGTTAGACAC CCTTATTCTG ACGAAGTAGA TAGAAGTATT     6300
CGAGTGGTAA GTCCTTGTGG TATGTGTAGG GAGTTGATTT CAGACTATGC ACCAGATTGT     6360
TTTGTGTTAA TAGAAATGAA TGGCAAGTTA GTCAAAACTA CGATTGAAGA ACTCATTCCA     6420
CTCAAATATA CCCGAAATTA AAAGTTTTAC CACCAAGCTT ATCGATTAGT CCAATTTGTT     6480
AAAGACAGGA TATCAGTGGT CCAGGCTCTA GTTTTGACTC AACAATATCA CCAGCTGAAG     6540
CCTATAGAGT ACGAGCCATA GATAAAATAA AAGATTTTAT TTAGTCTCCA GAAAAAGGGG     6600
GGAATGAAAG ACCCCACCTG TAGGTTTGGC AAGCTAGCTT AAGTAACGCC ATTTTGCAAG     6660
GCATGGAAAA ATACATAACT GAGAATAGAG AAGTTCAGAT CAAGGTCAGG AACAGATGGA     6720
ACAGTCGAGA ACTTGTTTAT TGCAGCTTAT AATGGTTACA AATAAAGCAA TAGCATCACA     6780
AATTTCACAA ATAAAGCATT TTTTTCACTG CATTCTAGTT GTGGTTTGTC CAAACTCATC     6840
AATGTATCTT ATCATGTCTG GATCCCCAGG AAGCTCCTCT GTGTCCTCAT AAACCCTAAC     6900
CTCCTCTACT TGAGAGGACA TTCCAATCAT AGGCTGCCCA TCCACCCTCT GTGTCCTCCT     6960
GTTAATTAGG TCACTTAACA AAAAGGAAAT TGGGTAGGGG TTTTTCACAG ACCGCTTTCT     7020
AAGGGTAATT TTAAAATATC TGGGAAGTCC CTTCCACTGC TGTGTTCCAG AAGTGTTGGT     7080
AAACAGCCCA CAAATGTCAA CAGCAGAAAC ATACAAGCTG TCAGCTTTGC ACAAGGGCCC     7140
AACACCCTGC TCATCAAGAA GCACTGTGGT TGCTGTGTTA GTAATGTGCA AAACAGGAGG     7200
CACATTTTCC CCACCTGTGT AGGTTCCAAA ATATCTAGTG TTTTCATTTT TACTTGGATC     7260
AGGAACCCAG CACTCCACTG GATAAGCATT ATCCTTATCC AAAACAGCCT TGTGGTCAGT     7320
GTTCATCTGC TGACTGTCAA CTGTAGCATT TTTGGGGTT ACAGTTTGAG CAGGATATTT     7380
GGTCCTGTAG TTTGCTAACA CACCCTGCAG CTCCAAAGGT TCCCCACCAA CAGCAAAAAA     7440
ATGAAAATTT GACCCTTGAA TGGGTTTTCC AGCACCATTT TCATGAGTTT TTTGTGTCCC     7500
TGAATGCAAG TTTAACATAG CAGTTACCCC AATAACCTCA GTTTTAACAG TAACAGCTTC     7560
CCACATCAAA ATATTTCCAC AGGTTAAGTC CTCATTTAAA TTAGGCAAAG GAATTC         7616
```

Figure 7a. HCMV+intron Sequence

```
AGATCTCCCG ATCCCCTATG GTCGACTCTC AGTACAATCT GCTCTGATGC CGCATAGTTA    60
AGCCAGTATC TGCTCCCTGC TTGTGTGTTG GAGGTCGCTG AGTAGTGCGC GAGCAAAATT   120
TAAGCTACAA CAAGGCAAGG CTTGACCGAC AATTGCATGA AGAATCTGCT TAGGGTTAGG   180
CGTTTTGCGC TGCTTCGCGA TGTACGGGCC AGATATACGC GTTGACATTG ATTATTGACT   240
AGTTATTAAT AGTAATCAAT TACGGGGTCA TTAGTTCATA GCCCATATAT GGAGTTCCGC   300
GTTACATAAC TTACGGTAAA TGGCCCGCCT GGCTGACCGC CCAACGACCC CCGCCCATTG   360
ACGTCAATAA TGACGTATGT TCCCATAGTA ACGCCAATAG GGACTTTCCA TTGACGTCAA   420
TGGGTGGACT ATTTACGGTA AACTGCCCAC TTGGCAGTAC ATCAAGTGTA TCATATGCCA   480
AGTACGCCCC CTATTGACGT CAATGACGGT AAATGGCCCG CCTGGCATTA TGCCCAGTAC   540
ATGACCTTAT GGGACTTTCC TACTTGGCAG TACATCTACG TATTAGTCAT CGCTATTACC   600
ATGGTGATGC GGTTTTGGCA GTACATCAAT GGGCGTGGAT AGCGGTTTGA CTCACGGGGA   660
TTTCCAAGTC TCCACCCCAT TGACGTCAAT GGGAGTTTGT TTTGGCACCA AAATCAACGG   720
GACTTTCCAA AATGTCGTAA CAACTCCGCC CCATTGACGC AAATGGGCGG TAGGCGTGTA   780
CGGTGGGAGG TCTATATAAG CAGAGCTCTC TGGCTAACTA GAGAACCCAC TGCTTAACTG   840
GCTTATCGAA ATGTCGACTG AGAACTTCAG GGTGAGTTTG GGGACCCTTG ATTGTTCTTT   900
CTTTTTCGCT ATTGTAAAAT TCATGTTATA TGGAGGGGGC AAAGTTTTCA GGGTGTTGTT   960
TAGAATGGGA AGATGTCCCT TGTATCACCA TGGACCCTCA TGATAATTTT GTTTCTTTCA  1020
CTTTCTACTC TGTTGACAAC CATTGTCTCC TCTTATTTTC TTTTCATTTT CTGTAACTTT  1080
TCGTTAAAC TTTAGCTTGC ATTTGTAACG AATTTTTAAA TTCACTTTTG TTTATTTGTC  1140
AGATTGTAAG TACTTTCTCT AATCACTTTT TTTTCAAGGC AATCAGGGTA TATTATATTG  1200
TACTTCAGCA CAGTTTTAGA GAACAATTGT TATAATTAAA TGATAAGGTA GAATATTTCT  1260
GCATATAAAT TCTGGCTGGC GTGGAAATAT TCTTATTGGT AGAAACAACT ACATCCTGGT  1320
CATCATCCTG CCTTTCTCTT TATGGTTACA ATGATATACA CTGTTTGAGA TGAGGATAAA  1380
ATACTCTGAG TCCAAACCGG GCCCCTCTGC TAACCATGTT CATGCCTTCT TCTTTTTCCT  1440
ACAGCTCCTG GGCAACGTGC TGGTTGTTGT GCTGTCTCAT CATTTTGGCA AGAATTGGCC  1500
GCAAGCTTCT GCAGCATCGT TCTGTGTTGT CTCTGTCTGA CTGTGTTTCT GTATTTGTCT  1560
GAGAATATGG GCCAGACTGT TACCACTCCC TTAAGTTTGA CCTTAGGTCA CTGGAAAGAT  1620
GTCGAGCGGA TCGCTCACAA CCAGTCGGTA GATGTCAAGA AGAGACGTTG GGTTACCTTC  1680
TGCTCTGCAG AATGCCAAC CTTTAACGTC GGATGGCCGC GAGACGGCAC CTTTAACCGA  1740
GACCTCATCA CCCAGGTTAA GATCAAGGTC TTTTCACCTG GCCCGCATGG ACACCCAGAC  1800
CAGGTCCCCT ACATCGTGAC CTGGGAAGCC TTGGCTTTTG ACCCCCCTCC CTGGGTCAAG  1860
CCCTTTGTAC ACCCTAAGCC TCCGCCTCCT CTTCCTCCAT CCGCCCCGTC TCTCCCCCTT  1920
GAACCTCCTC GTTCGACCCC GCCTCGATCC TCCCTTTATC CAGCCCTCAC TCCTTCTCTA  1980
GGCGCCAAAC CTAAACCTCA AGTTCTTTCT GACAGTGGGG GGCCGCTCAT CGACCTACTT  2040
ACAGAAGACC CCCCGCCTTA TAGGGACCCA AGACCACCC CTTCCGACAG GACGGAAAT  2100
GGTGGAGAAG CGACCCCTGC GGGAGAGGCA CCGGACCCCT CCCCAATGGC ATCTCGCCTA  2160
CGTGGGAGAC GGGAGCCCCC TGTGGCCGAC TCCACTACCT CGCAGGCATT CCCCCTCCGC  2220
GCAGGAGGAA ACGGACAGCT TCAATACTGG CCGTTCTCCT CTTCTGACCT TTACAACTGG  2280
AAAAATAATA ACCCTTCTTT TTCTGAAGAT CCAGGTAAAC TGACAGCTCT GATCGAGTCT  2340
GTTCTCATCA CCCATCAGCC CACCTGGGAC GACTGTCAGC AGCTGTTGGG GACTCTGCTG  2400
ACCGGAGAAG AAAAACAACG GGTGCTCTTA GAGGCTAGAA AGGCGGTGCG GGGCGATGAT  2460
GGGCGCCCCA CTCAACTGCC CAATGAAGTC GATGCCGCTT TTCCCCTCGA GCGCCCAGAC  2520
TGGGATTACA CCACCCAGGC AGGTAGGAAC CACCTAGTCC ACTATCGCCA GTTGCTCCTA  2580
GCGGGTCTCC AAAACGCGGG CAGAAGCCCC ACCAATTTGG CCAAGGTAAA AGGAATAACA  2640
CAAGGGCCCA ATGAGTCTCC CTCGGCCTTC CTAGAGAGAC TTAAGGAAGC CTATCGCAGG  2700
TACACTCCTT ATGACCCTGA GGACCCAGGG CAAGAAACTA ATGTGTCTAT GTCTTTCATT  2760
TGGCAGTCTG CCCCAGACAT TGGGAGAAAG TTAGAGAGGT TAGAAGATTT AAAAAACAAG  2820
ACGCTTGGAG ATTTGGTTAG AGAGGCAGAA AAGATCTTTA ATAAACGAGA AACCCCGGAA  2880
GAAAGAGAGG AACGTATCAG GAGAGAAACA GAGGAAAAAG AAGAACGCCG TAGGACAGAG  2940
GATGAGCAGA AAGAGAAAGA AAGAGATCGT AGGAGACATA GAGAGATGAG CAAGCTATTG  3000
GCCACTGTCG TTAGTGGACA GAAACAGGAT AGACAGGGAG GAGAACGAAG GAGGTCCCAA  3060
CTCGATCGCG ACCAGTGTGC CTACTGCAAA GAAAAGGGGC ACTGGGCTAA AGATTGTCCC  3120
AAGAAACCAC GAGGACCTCG GGGACCAAGA CCCCAGACCT CCCTCCTGAC CTAGATGAC   3180
TAGGGAGGTC AGGGTCAGGA GCCCCCCCCT GAACCCAGGA TAACCCTCAA AGTCGGGGGG  3240
CAACCCGTCA CCTTCCTGGT AGATACTGGG GCCCAACACT CCGTGCTGAC CCAAAATCCT  3300
GGACCCCTAA GTGATAAGTC TGCCTGGGTC CAAGGGCTA CTGGAGGAAA GCGGTATCGC  3360
TGGACCACGG ATCGCAAAGT ACATCTAGCT ACCGGTAAGG TCACCCACTC TTTCCTCCAT  3420
GTACCAGACT GTCCCTATCC TCTGTTAGGA AGAGATTTGC TGACTAAACT AAAAGCCCAA  3480
ATCCACTTTG AGGGATCAGG AGCTCAGGTT ATGGGACCAA TGGGGCAGCC CCTGCAAGTG  3540
TTGACCCTAA ATATAGAAGA TGAGCATCGG CTACATGAGA CCTCAAAAGA GCCAGATGTT  3600
TCTCTAGGGT CCACATGGCT GTCTGATTTT CCTCAGGCCT GGGCGGAAAC CGGGGCATG   3660
GGACTGGCAG TTCGCCAAGC TCCTCTGATC ATACCTCTGA AAGCAACCTC TACCCCGTG   3720
TCCATAAAAC AATACCCCAT GTCACAAGAA GCCAGACTGG GGATCAAGCC CCACATACAG  3780
AGACTGTTGG ACCAGGGAAT ACTGGTACCC TGCCAGTCCC CTGGAACAC GCCCCTGCTA  3840
CCCGTTAAGA AACCAGGGAC TAATGATTAT AGGCCTGTCC AGGATCTGAG AGAAGTCAAC  3900
AAGCGGGTGG AAGACATCCA CCCCACCGTG CCCAACCCTT ACAACCTCTT GAGCGGGCTC  3960
CCACCGTCCC ACCAGTGGTA CACTGTGCTT GATTTAAAGG ATGCCTTTTT CTGCCTGAGA  4020
CTCCACCCCA CCAGTCAGCC TCTCTTCGCC TTTGAGTGGA GAGATCCAGA GATGGGAATC  4080
```

Figure 7b. hCMV+intron Sequence

```
TCAGGACAAT TGACCTGGAC CAGACTCCCA CAGGGTTTCA AAAACAGTCC CACCCTGTTT    4140
GATGAGGCAC TGCACAGAGA CCTAGCAGAC TTCCGGATCC AGCACCCAGA CTTGATCCTG    4200
CTACAGTACG TGGATGACTT ACTGCTGGCC GCCACTTCTG AGCTAGACTG CCAACAAGGT    4260
ACTCGGGCCC TGTTACAAAC CCTAGGGAAC CTCGGGTATC GGGCCTCGGC CAAGAAAGCC    4320
CAAATTTGCC AGAAACAGGT CAAGTATCTG GGGTATCTTC TAAAAGAGGG TCAGAGATGG    4380
CTGACTGAGG CCAGAAAAGA GACTGTGATG GGGCAGCCTA CTCCGAAGAC CCCTCGACAA    4440
CTAAGGGAGT TCCTAGGGAC GGCAGGCTTC TGTCGCCTCT GGATCCCTGG GTTTGCAGAA    4500
ATGGCAGCCC CCTTGTACCC TCTCACCAAA ACGGGGACTC TGTTTAATTG GGGCCCAGAC    4560
CAACAAAAGG CCTATCAAGA AATCAAGCAA GCTCTTCTAA CTGCCCCAGC CCTGGGGTTG    4620
CCAGATTTGA CTAAGCCCTT TGAACTCTTT GTCGACGAGA AGCAGGGCTA CGCCAAAGGT    4680
GTCCTAACGC AAAAACTGGG ACCTTGGCGT CGGCCGGTGG CCTACCTGTC CAAAAAGCTA    4740
GACCCAGTAG CAGCTGGGTG GCCCCCTTGC CTACGGATGG TAGCAGCCAT TGCCGTACTG    4800
ACAAAGGATG CAGGCAAGCT AACCATGGGA CAGCCACTAG TCATTCTGGC CCCCCATGCA    4860
GTAGAGGCAC TAGTCAAACA ACCCCCCGAC CGCTGGCTTT CCAACGCCCG GATGACTCAC    4920
TATCAGGCCT TGCTTTTGGA CACGGACCGG GTCCAGTTCG GACCGGTGGT AGCCCTGAAC    4980
CCGGCTACGC TGCTCCCACT GCCTGAGGAA GGGCTGCAAC ACAACTGCCT TGATATCCTG    5040
GCCGAAGCCC ACGGAACCCG ACCCGACCTA ACGGACCAGC CGCTCCCAGA CGCCGACCAC    5100
ACCTGGTACA CGGATGGAAG CAGTCTCTTA CAAGAGGGAC AGCGTAAGGC GGGAGCTGCG    5160
GTGACCACCG AGACCGAGGT AATCTGGGCT AAAGCCCTGC CAGCCGGGAC ATCCGCTCAG    5220
CGGGCTGAAC TGATAGCACT CACCCAGGCC CTAAAGATGG CAGAAGGTAA GAAGCTAAAT    5280
GTTTATACTG ATAGCCGTTA TGCTTTTGCT ACTGCCCATA TCCATGGAGA AATATACAGA    5340
AGGCGTGGGT TGCTCACATC AGAAGGCAAA GAGATCAAAA ATAAAGACGA GATCTTGGCC    5400
CTACTAAAAG CCCTCTTTCT GCCCAAAAGA CTTAGCATAA TCCATTGTCC AGGACATCAA    5460
AAGGGACACA GCGCCGAGGC TAGAGGCAAC CGGATGGCTG ACCAAGCGGC CCGAAAGGCA    5520
GCCATCACAG AGACTCCAGA CACCTCTACC CTCCTCATAG AAAATTCATC ACCCTACACC    5580
TCAGAACATT TTCATTACAC AGTGACTGAT ATAAAGGACC TAACCAAGTT GGGGGCCATT    5640
TATGATAAAA CAAAGAAGTA TTGGGTCTAC CAAGGAAAAC CTGTGATGCC TGACCAGTTT    5700
ACTTTTGAAT TATTAGACTT TCTTCATCAG CTGACTCACC TCAGCTTCTC AAAAATGAAG    5760
GCTCTCCTAG AGAGAAGCCA CAGTCCCTAC TACATGCTGA ACCGGGATCG AACACTCAAA    5820
AATATCACTG AGACCTGCAA AGCTTGTGCA CAAGTCAACG CCAGCAAGTC TGCCGTTAAA    5880
CAGGGAACTA GGGTCCGCGG GCATCGGCCC GGCACTCATT GGGAGATCGA TTTCACCGAG    5940
ATAAAGCCCG GATTGTATGG CTATAAATAT CTTCTAGTTT TTATAGATAC CTTTTCTGGC    6000
TGGATAGAAG CCTTCCCAAC CAAGAAAGAA ACCGCCAAGG TCGTAACCAA GAAGCTACTA    6060
GAGGAGATCT TCCCCAGGTT CGGCATGCCT CAGGTATTGG GAACTGACAA TGGGCCTGCC    6120
TTCGTCTCCA AGGTGAGTCA GACAGTGGCC GATCTGTTGG GGATTGATTG GAAATTACAT    6180
TGTGCATACA GACCCCAAAG CTCAGGCCAG GTAGAAAGAA TGAATAGAAC CATCAAGGAG    6240
ACTTTAACTA AATTAACGCT TGCAACTGGC TCTAGAGACT GGGTGCTCCT ACTCCCCTTA    6300
GCCCTGTACC GAGCCCGCAA CACGCCGGGC CCCCATGGCC TCACCCCATA TGAGATCTTA    6360
TATGGGGCAC CCCCGCCCCT TGTAAACTTC CCTGACCCTG ACATGACAAG AGTTACTAAC    6420
AGCCCCTCTC TCCAAGCTCA CTTACAGGCT CTCTACTTAG TCCAGCACGA AGTCTGGAGA    6480
CCTCTGGCGG CAGCCTACCA AGAACAACTG GACCGACCGG TGGTACCTCA CCCTTACCGA    6540
GTCGGCGACA CAGTGTGGGT CCGCCGACAC CAGACTAAGA ACCTAGAACC TCGCTGGAAA    6600
GGACCTTACA CAGTCCTGCT GACCACCCCC ACCGCCCTCA AGTAGACGG CATCGCAGCT    6660
TGGATACACG CCGCCCACGT GAAGGCTGCC GACCCCGGGG TGGACCATC CTCTAGACTG    6720
ACATGGCGCG TTCAACGCTC TCAAAACCCC TTAAAAATAA GGTTAACCCG CGAGGCCCCC    6780
TAATCCCCTT AATTCTTCTG ATGCTCAGAG GGGTCAGTAC TGCTTCGCCC GGCTCCAGTG    6840
CGGCCCAGCC GGCCACCATG AAAACATTTA ACATTTCTCA ACAAGATCTA GAATTAGTAG    6900
AAGTAGCGAC AGAGAAGATT ACAATGCTTT ATGAGGATAA TAAACATCAT GTGGGAGCGG    6960
CAATTCGTAC GAAAACAGGA GAAATCATTT CGGCAGTACA TATTGAAGCG TATATAGGAC    7020
GAGTAACTGT TTGTGCAGAA GCCATTGCGA TTGGTAGTGC AGTTTCGAAT GGACAAAAGG    7080
ATTTTGACAC GATTGTAGCT GTTAGACACC CTTATTCTGA CGAAGTAGAT AGAAGTATTC    7140
GAGTGGTAAG TCCTTGTGGT ATGTGTAGGG AGTTGATTTC AGACTATGCA CCAGATTGTT    7200
TTGTGTTAAT AGAAATGAAT GGCAAGTTAG TCAAAACTAC GATTGAAGAA CTCATTCCAC    7260
TCAAATATAC CCGAAATTAA AAGTTTTACC ACCAAGCTTA TCGAATTC                 7308
```

Figure 8a. hCMV+intronkaSD Sequence

| | | | | | | |
|---|---|---|---|---|---|---|
| AGATCTCCCG | ATCCCTATG | GTCGACTCTC | AGTACAATCT | GCTCTGATGC | CGCATAGTTA | 60 |
| AGCCAGTATC | TGCTCCCTGC | TTGTGTGTTG | GAGGTCGCTG | AGTAGTGCGC | GAGCAAAATT | 120 |
| TAAGCTACAA | CAAGGCAAGG | CTTGACCGAC | AATTGCATGA | AGAATCTGCT | TAGGGTTAGG | 180 |
| CGTTTTGCGC | TGCTTCGCGA | TGTACGGGCC | AGATATACGC | GTTGACATTG | ATTATTGACT | 240 |
| AGTTATTAAT | AGTAATCAAT | TACGGGGTCA | TTAGTTCATA | GCCCATATAT | GGAGTTCCGC | 300 |
| GTTACATAAC | TTACGGTAAA | TGGCCCGCCT | GGCTGACCGC | CCAACGACCC | CCGCCCATTG | 360 |
| ACGTCAATAA | TGACGTATGT | TCCCATAGTA | ACGCCAATAG | GGACTTTCCA | TTGACGTCAA | 420 |
| TGGGTGGACT | ATTTACGGTA | AACTGCCCAC | TTGGCAGTAC | ATCAAGTGTA | TCATATGCCA | 480 |
| AGTACGCCCC | CTATTGACGT | CAATGACGGT | AAATGGCCCG | CCTGGCATTA | TGCCCAGTAC | 540 |
| ATGACCTTAT | GGGACTTTCC | TACTTGGCAG | TACATCTACG | TATTAGTCAT | CGCTATTACC | 600 |
| ATGGTGATGC | GGTTTTGGCA | GTACATCAAT | GGGCGTGGAT | AGCGGTTTGA | CTCACGGGGA | 660 |
| TTTCCAAGTC | TCCACCCCAT | TGACGTCAAT | GGGAGTTTGT | TTTGGCACCA | AAATCAACGG | 720 |
| GACTTTCCAA | AATGTCGTAA | CAACTCCGCC | CCATTGACGC | AAATGGGCGG | TAGGCGTGTA | 780 |
| CGGTGGGAGG | TCTATATAAG | CAGAGCTCTC | TGGCTAACTA | GAGAACCCAC | TGCTTAACTG | 840 |
| GCTTATCGAA | ATGTCGACTG | AGAACTTCAG | GGTGAGTTTG | GGGACCCTTG | ATTGTTCTTT | 900 |
| CTTTTTCGCT | ATTGTAAAAT | TCATGTTATA | TGGAGGGGGC | AAAGTTTTCA | GGGTGTTGTT | 960 |
| TAGAATGGGA | AGATGTCCCT | TGTATCACCA | TGGACCCTCA | TGATAATTTT | GTTTCTTTCA | 1020 |
| CTTTCTACTC | TGTTGACAAC | CATTGTCTCC | TCTTATTTTC | TTTTCATTTT | CTGTAACTTT | 1080 |
| TTCGTTAAAC | TTTAGCTTGC | ATTTGTAACG | AATTTTTTAAA | TTCACTTTTG | TTTATTTGTC | 1140 |
| AGATTGTAAG | TACTTTCTCT | AATCACTTTT | TTTTCAAGGC | AATCAGGGTA | TATTATATTG | 1200 |
| TACTTCAGCA | CAGTTTTAGA | GAACAATTGT | TATAATTAAA | TGATAAGGTA | GAATATTTCT | 1260 |
| GCATATAAAT | TCTGGCTGGC | GTGGAAATAT | TCTTATTGGT | AGAAACAACT | ACATCCTGGT | 1320 |
| CATCATCCTG | CCTTTCTCTT | TATGGTTACA | ATGATATACA | CTGTTTGAGA | TGAGGATAAA | 1380 |
| ATACTCTGAG | TCCAAACCGG | GCCCCTCTGC | TAACCATGTT | CATGCCTTCT | TCTTTTTCCT | 1440 |
| ACAGCTCCTG | GGCAACGTGC | TGGTTGTTGT | GCTGTCTCAT | CATTTTGGCA | AGAATTGGCC | 1500 |
| GCAAGCTTCT | GCAGCATCGT | TCTGTGTTGT | CTCTGTCTGA | CTGTGTTTCT | GTATTTGTCT | 1560 |
| GAGAATATGG | GCCAGACTGT | TACCACTCCC | TTAAGTTTGA | CCTTAGGTCA | CTGGAAAGAT | 1620 |
| GTCGAGCGGA | TCGCTCACAA | CCAGTCGGTA | GATGTCAAGA | AGAGACGTTG | GGTTACCTTC | 1680 |
| TGCTCTGCAG | AATGGCCAAC | CTTTAACGTC | GGATGGCCGC | GAGACGGCAC | CTTTAACCGA | 1740 |
| GACCTCATCA | CCCAGGTTAA | GATCAAGGTC | TTTTCACCTG | GCCCGCATGG | ACACCCAGAC | 1800 |
| CAGGTCCCCT | ACATCGTGAC | CTGGGAAGCC | TTGGCTTTTG | ACCCCCCTCC | CTGGGTCAAG | 1860 |
| CCCTTTGTAC | ACCCTAAGCC | TCCGCCTCCT | CTTCCTCCAT | CCGCCCCGTC | TCTCCCCCTT | 1920 |
| GAACCTCCTC | GTTCGACCCC | GCCTCGATCC | TCCCTTTATC | CAGCCCTCAC | TCCTTCTCTA | 1980 |
| GGCGCCAAAC | CTAAACCTCA | AGTTCTTTCT | GACAGTGGGG | GCCGCTCAT | CGACCTACTT | 2040 |
| ACAGAAGACC | CCCCGCCTTA | TAGGGACCCA | AGACCACCCC | CTTCCGACAG | GGACGGAAAT | 2100 |
| GGTGGAGAAG | CGACCCCTGC | GGGAGAGGCA | CCGGACCCCT | CCCCAATGGC | ATCTCGCCTA | 2160 |
| CGTGGGAGAC | GGGAGCCCCC | TGTGGCCGAC | TCCACTACCT | CGCAGGCATT | CCCCCTCCGC | 2220 |
| GCAGGAGGAA | ACGGACAGCT | TCAATACTGG | CCGTTCTCCT | CTTCTGACCT | TTACAACTGG | 2280 |
| AAAAATAATA | ACCCTTCTTT | TTCTGAAGAT | CCAGGTAAAC | TGACAGCTCT | GATCGAGTCT | 2340 |
| GTTCTCATCA | CCCATCAGCC | CACCTGGGAC | GACTGTCAGC | AGCTGTTGGG | GACTCTGCTG | 2400 |
| ACCGGAGAAG | AAAAACAACG | GGTGCTCTTA | GAGGCTAGAA | AGGCGGTGCG | GGGCGATGAT | 2460 |
| GGGCGCCCCA | CTCAACTGCC | CAATGAAGTC | GATGCCGCTT | TTCCCCTCGA | GCGCCCAGAC | 2520 |
| TGGGATTACA | CCACCCAGGC | AGGACGCAAC | CACCTAGTCC | ACTATCGCCA | GTTGCTCCTA | 2580 |
| GCGGGTCTCC | AAAACGCGGG | CAGAAGCCCC | ACCAATTTGG | CCAAGGTAAA | AGGAATAACA | 2640 |
| CAAGGGCCCA | ATGAGTCTCC | CTCGGCCTTC | CTAGAGAGAC | TTAAGGAAGC | CTATCGCAGG | 2700 |
| TACACTCCTT | ATGACCCTGA | GGACCCAGGG | CAAGAAACTA | ATGTGTCTAT | GTCTTTCATT | 2760 |
| TGGCAGTCTG | CCCCAGACAT | TGGGAGAAAG | TTAGAGAGGT | TAGAAGATTT | AAAAAACAAG | 2820 |
| ACGCTTGGAG | ATTTGGTTAG | AGAGGCAGAA | AAGATCTTTA | ATAAACGAGA | AACCCCGGAA | 2880 |
| GAAAGAGAGG | AACGTATCAG | GAGAGAAACA | GAGGAAAAAG | AAGAACGCCG | TAGGACAGAG | 2940 |
| GATGAGCAGA | AAGAGAAAGA | AAGAGATCGT | AGGAGACATA | GAGAGATGAG | CAAGCTATTG | 3000 |
| GCCACTGTCG | TTAGTGGACA | GAAACAGGAT | AGACAGGGAG | GAGAACGAAG | GAGGTCCCAA | 3060 |
| CTCGATCGCG | ACCAGTGTGC | CTACTGCAAA | GAAAAGGGGC | ACTGGGCTAA | AGATTGTCCC | 3120 |
| AAGAAACCAC | GAGGACCTCG | GGACCAAGA | CCCAGACCT | CCCTCCTGAC | CCTAGATGAC | 3180 |
| TAGGGAGGTC | AGGGTCAGGA | GCCCCCCCT | GAACCCAGGA | TAACCCTCAA | AGTCGGGGGG | 3240 |
| CAACCCGTCA | CCTTCCTGGT | AGATACTGGG | GCCCAACACT | CCGTGCTGAC | CCAAAATCCT | 3300 |
| GGACCCTAA | GTGATAAGTC | TGCCTGGGTC | CAAGGGGCTA | CTGGAGGAAA | GCGGTATCGC | 3360 |
| TGGACCACGG | ATCGCAAAGT | ACATCTAGCT | ACCGGTAAGG | TCACCCACTC | TTTCCTCCAT | 3420 |
| GTACCAGACT | GTCCCTATCC | TCTGTTAGGA | AGAGATTTGC | TGACTAAACT | AAAAGCCCAA | 3480 |
| ATCCACTTTG | AGGGATCAGG | AGCTCAGGTT | ATGGGACCAA | TGGGGCAGCC | CCTGCAAGTG | 3540 |
| TTGACCCTAA | ATATAGAAGA | TGAGCATCGG | CTACATGAGA | CCTCAAAAGA | GCCAGATGTT | 3600 |
| TCTCTAGGGT | CCACATGGCT | GTCTGATTTT | CCTCAGGCCT | GGGCGGAAAC | CGGGGGCATG | 3660 |
| GGACTGGCAG | TTCGCCAAGC | TCCTCTGATC | ATACCTCTGA | AAGCAACCTC | TACCCCCGTG | 3720 |
| TCCATAAAAC | AATACCCCAT | GTCACAAGAA | GCCAGACTGG | GGATCAAGCC | CCACATACAG | 3780 |
| AGACTGTTGG | ACCAGGGAAT | ACTGGTACCC | TGCCAGTCCC | CCTGGAACAC | GCCCCTGCTA | 3840 |
| CCCGTTAAGA | AACCAGGGAC | TAATGATTAT | AGGCCTGTCC | AGGATCTGAG | AGAAGTCAAC | 3900 |
| AAGCGGGTGG | AAGACATCCA | CCCCACCGTG | CCCAACCCTT | ACAACCTCTT | GAGCGGGCTC | 3960 |
| CCACCGTCCC | ACCAGTGGTA | CACTGTGCTT | GATTTAAAGG | ATGCCTTTTT | CTGCCTGAGA | 4020 |
| CTCCACCCCA | CCAGTCAGCC | TCTCTTCGCC | TTTGAGTGGA | GAGATCCAGA | GATGGGAATC | 4080 |

Figure 8b. hCMV+intronkaSD Sequence

```
TCAGGACAAT TGACCTGGAC CAGACTCCCA CAGGGTTTCA AAAACAGTCC CACCCTGTTT      4140
GATGAGGCAC TGCACAGAGA CCTAGCAGAC TTCCGGATCC AGCACCCAGA CTTGATCCTG      4200
CTACAGTACG TGGATGACTT ACTGCTGGCC GCCACTTCTG AGCTAGACTG CCAACAAGGT      4260
ACTCGGGCCC TGTTACAAAC CCTAGGGAAC CTCGGGTATC GGGCCTCGGC CAAGAAAGCC      4320
CAAATTTGCC AGAAACAGGT CAAGTATCTG GGTATCTTC  TAAAAGAGGG TCAGAGATGG      4380
CTGACTGAGG CCAGAAAAGA GACTGTGATG GGGCAGCCTA CTCCGAAGAC CCCTCGACAA      4440
CTAAGGGAGT TCCTAGGGAC GGCAGGCTTC TGTCGCCTCT GGATCCCTGG GTTTGCAGAA      4500
ATGGCAGCCC CCTTGTACCC TCTCACCAAA ACGGGGACTC TGTTTAATTG GGGCCCAGAC      4560
CAACAAAAGG CCTATCAAGA AATCAAGCAA GCTCTTCTAA CTGCCCCAGC CCTGGGGTTG      4620
CCAGATTTGA CTAAGCCCTT TGAACTCTTT GTCGACGAGA AGCAGGGCTA CGCCAAAGGT      4680
GTCCTAACGC AAAAACTGGG ACCTTGGCGT CGGCCGGTGG CCTACCTGTC CAAAAAGCTA      4740
GACCCAGTAG CAGCTGGGTG GCCCCCTTGC CTACGGATGG TAGCAGCCAT TGCCGTACTG      4800
ACAAAGGATG CAGGCAAGCT AACCATGGGA CAGCCACTAG TCATTCTGGC CCCCCATGCA      4860
GTAGAGGCAC TAGTCAAACA ACCCCCCGAC CGCTGGCTTT CCAACGCCCG GATGACTCAC      4920
TATCAGGCCT TGCTTTTGGA CACGGACCGG GTCCAGTTCG GACCGGTGGT AGCCCTGAAC      4980
CCGGCTACGC TGCTCCCACT GCCTGAGGAA GGGCTGCAAC ACAACTGCCT TGATATCCTG      5040
GCCGAAGCCC ACGGAACCCG ACCCGACCTA ACGGACCAGC CGCTCCCAGA CGCCGACCAC      5100
ACCTGGTACA CGGATGGAAG CAGTCTCTTA CAAGAGGGAC AGCGTAAGGC GGGAGCTGCG      5160
GTGACCACCG AGACCGAGGT AATCTGGGCT AAAGCCCTGC CAGCCGGGAC ATCCGCTCAG      5220
CGGGCTGAAC TGATAGCACT CACCCAGGCC CTAAAGATGG CAGAAGGTAA GAAGCTAAAT      5280
GTTTATACTG ATAGCCGTTA TGCTTTTGCT ACTGCCCATA TCCATGGAGA AATATACAGA      5340
AGGCGTGGGT TGCTCACATC AGAAGGCAAA GAGATCAAAA ATAAAGACGA GATCTTGGCC      5400
CTACTAAAAG CCCTCTTTCT GCCCAAAAGA CTTAGCATAA TCCATTGTCC AGGACATCAA      5460
AAGGGACACA GCGCCGAGGC TAGAGGCAAC CGGATGGCTG ACCAAGCGGC CGAAAGGCA       5520
GCCATCACAG AGACTCCAGA CACCTCTACC CTCCTCATAG AAAATTCATC ACCCTACACC      5580
TCAGAACATT TTCATTACAC AGTGACTGAT ATAAAGGACC TAACCAAGTT GGGGGCCATT      5640
TATGATAAAA CAAAGAAGTA TTGGGTCTAC CAAGGAAAAC CTGTGATGCC TGACCAGTTT      5700
ACTTTTGAAT TATTAGACTT TCTTCATCAG CTGACTCACC TCAGCTTCTC AAAAATGAAG      5760
GCTCTCCTAG AGAGAAGCCA CAGTCCCTAC TACATGCTGA ACCGGGATCG AACACTCAAA      5820
AATATCACTG AGACCTGCAA AGCTTGTGCA CAAGTCAACG CCAGCAAGTC TGCCGTTAAA      5880
CAGGGAACTA GGGTCCGCGG GCATCGGCCC GGCACTCATT GGGAGATCGA TTTCACCGAG      5940
ATAAAGCCCG GATTGTATGG CTATAAATAT CTTCTAGTTT TTATAGATAC CTTTTCTGGC      6000
TGGATAGAAG CCTTCCCAAC CAAGAAAGAA ACCGCCAAGG TCGTAACCAA GAAGCTACTA      6060
GAGGAGATCT TCCCCAGGTT CGGCATGCCT CAGGTATTGG GAACTGACAA TGGGCCTGCC      6120
TTCGTCTCCA AGGTGAGTCA GACAGTGGCC GATCTGTTGG GGATTGATTG GAAATTACAT      6180
TGTGCATACA GACCCCAAAG CTCAGGCCAG GTAGAAAGAA TGAATAGAAC CATCAAGGAG      6240
ACTTTAACTA AATTAACGCT TGCAACTGGC TCTAGAGACT GGGTGCTCCT ACTCCCCTTA      6300
GCCCTGTACC GAGCCCGCAA CACGCCGGGC CCCCATGGCC TCACCCCATA TGAGATCTTA      6360
TATGGGCAC  CCCCGCCCCT TGTAAACTTC CCTGACCCTG ACATGACAAG AGTTACTAAC      6420
AGCCCCTCTC TCCAAGCTCA CTTACAGGCT CTCTACTTAG TCCAGCACGA AGTCTGGAGA      6480
CCTCTGGCGG CAGCCTACCA AGAACAACTG GACCGACCGG TGGTACCTCA CCCTTACCGA      6540
GTCGGCGACA CAGTGTGGGT CCGCCGACAC CAGACTAAGA ACCTAGAACC TCGCTGGAAA      6600
GGACCTTACA CAGTCCTGCT GACCACCCCC ACCGCCCTCA AGTAGACGG  CATCGCAGCT      6660
TGGATACACG CCGCCCACGT GAAGGCTGCC GACCCGGGG  GTGGACCATC CTCTAGACTG      6720
ACATGGCGCG TTCAACGCTC TCAAAACCCC TTAAAATAA  GGTTAACCCG CGAGGCCCCC      6780
TAATCCCCTT AATTCTTCTG ATGCTCAGAG GGGTCAGTAC TGCTTCGCCC GGCTCCAGTG      6840
CGGCCCAGCC GGCCACCATG AAAACATTTA ACATTTCTCA ACAAGATCTA GAATTAGTAG      6900
AAGTAGCGAC AGAGAAGATT ACAATGCTTT ATGAGGATAA TAAACATCAT GTGGGAGCGG      6960
CAATTCGTAC GAAAACAGGA GAAATCATTT CGGCAGTACA TATTGAAGCG TATATAGGAC      7020
GAGTAACTGT TTGTGCAGAA GCCATTGCGA TTGGTAGTGC AGTTTCGAAT GGACAAAAGG      7080
ATTTTGACAC GATTGTAGCT GTTAGACACC CTTATTCTGA CGAAGTAGAT AGAAGTATTC      7140
GAGTGGTAAG TCCTTGTGGT ATGTGTAGGG AGTTGATTTC AGACTATGCA CCAGATTGTT      7200
TTGTGTTAAT AGAAATGAAT GGCAAGTTAG TCAAAACTAC GATTGAAGAA CTCATTCCAC      7260
TCAAATATAC CCGAAATTAA AAGTTTTACC ACCAAGCTTA TCGAATTC                  7308
```

Figure 9a. FBdelPASAF Sequence

```
CATATGCGGT GTGAAATACC GCACAGATGC GTAAGGAGAA AATACCGCAT CAGGCGCCAT    60
TCGCCATTCA GGCTGCGCAA CTGTTGGGAA GGGCGATCGG TGCGGGCCTC TTCGCTATTA   120
CGCCAGCTGG CGAAAGGGGG ATGTGCTGCA AGGCGATTAA GTTGGGTAAC GCCAGGGTTT   180
TCCCAGTCAC GACGTTGTAA AACGACGGCC AGTGAATTCC GATTAGTTCA ATTTGTTAAA   240
GACAGGATCT CAGTAGTCCA GGCTTTAGTC CTGACTCAAC AATACCACCA GCTAAAACCA   300
CTAGAATACG AGCCACAATA AATAAAAGAT TTTATTTAGT TTCCAGAAAA AGGGGGGAAT   360
GAAAGACCCC ACCAAATTGC TTAGCCTGAT AGCCGCAGTA ACGCCATTTT GCAAGGCATG   420
GAAAAATACC AAACCAAGAA TAGAGAAGTT CAGATCAAGG GCGGGTACAC GAAAACAGCT   480
AACGTTGGGC CAAACAGGAT ATCTGCGGTG AGCAGTTTCG GCCCCGGCCC GGGGCCAAGA   540
ACAGATGGTC ACCGCGGTTC GGCCCCGGCC CGGGGCCAAG AACAGATGGT CCCCAGATAT   600
GGCCCAACCC TCAGCAGTTT CTTAAGACCC ATCAGATGTT TCCAGGCTCC CCCAAGGACC   660
TGAAATGACC CTGTGCCTTA TTTGAATTAA CCAATCAGCC TGCTTCTCGC TTCTGTTCGC   720
GCGCTTCTGC TTCCCGAGCT CTATAAAAGA GCTACAACCC CCTCACTCGG CGCGCCAGTC   780
CTCCGATAGA CTGAGTCGCC CGGGTACCCG TGTATCCAAT AAATCCTCTT GCTGTTGCAT   840
CCGACTCGTG GTCTCGCTGT TCCTTGGGAG GGTCTCCTCA GAGTGATTGA CTACCCGTCT   900
CGGGGGTCTT TCATTTGGGG GCTCGTCCGG GATCTGGAGA CCCCTGCCCA GGGACCACCG   960
ACCCACCACC GGGAGGTAAG CTGGCCAAGA TCTTATATGG GGCACCCCCG CCCCTTGTAA  1020
ACTTCCCTGA CCCTGACATG ACCAGAGTTA CTAACAGCCC CTCTCTCCAA GCTCACTTAC  1080
AGGCTCTCTA CTTAGTCCAG CACGAAGTTT GGAGACCACT GGCGGCAGCT TACCAAGAAC  1140
AACTGGACCG GCCGGTGGTG CCTCACCCTT ACCGGGTCGG CGACACAGTG TGGGTCCGCC  1200
GACATCAAAC CAAGAACCTA GAACCTCGCT GGAAAGGACC TTACACAGTC CTGCTGACCA  1260
CCCCCACCGC CCTCAAAGTA GACGGTATCG CAGCTTGGAT ACACGCAGCC CACGTAAAGG  1320
CGGCCGACAC CGAGAGTGGA CCATCCTCTG GACGGACATG GCGCGTTCAA CGCTCTCAAA  1380
ACCCCCTCAA GATAAGATTA ACCCGTGGAA GCCCTTAATA GTCATGGGAG TCCTGTTAGG  1440
AGTAGGGATG GCAGAGAGCC CCCATCAGGT CTTTAATGTA ACCTGGAGAG TCACCAACCT  1500
GATGACTGGG CGTACCGCCA ATGCCACCTC CCTCCTGGGA ACTGTACAAG ATGCCTTCCC  1560
AAAATTATAT TTTGATCTAT GTGATCTGGT CGGAGAGGAG TGGGACCCTT CAGACCAGGA  1620
ACCGTATGTC GGGTATGGCT GCAAGTACCC CGCAGGGAGA CAGCGGACCC GGACTTTTGA  1680
CTTTTACGTG TGCCCTGGGC ATACCGTAAA GTCGGGGTGT GGGGGACCAG GAGAGGGCTA  1740
CTGTGGTAAA TGGGGGTGTG AAACCACCGG ACAGGCTTAC TGGAAGCCCA CATCATCGTG  1800
GGACCTAATC TCCCTTAAGC GCGGTAACAC CCCTGGGAC ACGGGATGCT CTAAAGTTGC   1860
CTGTGGCCCC TGCTACGACC TCTCCAAAGT ATCCAATTCC TTCAAGGGG CTACTCGAGG   1920
GGGCAGATGC AACCCTCTAG TCCTAGAATT CACTGATGCA GGAAAAAAGG CTAACTGGGA  1980
CGGGCCCAAA TCGTGGGGAC TGAGACTGTA CCGGACAGGA ACAGATCCTA TTACCATGTT  2040
CTCCCTGACC CGGCAGGTCC TTAATGTGGG ACCCCGAGTC CCCATAGGGC CAACCCAGT   2100
ATTACCCGAC CAAAGACTCC CTTCCTCACC AATAGAGATT GTACCGGCTC CACAGCCACC  2160
TAGCCCCCTC AATACCAGTT ACCCCCCTTC CACTACCAGT ACACCCTCAA CCTCCCCTAC  2220
AAGTCCAAGT GTCCCACAGC CACCCCCAGG AACTGGAGAT AGACTACTAG CTCTAGTCAA  2280
AGGAGCCTAT CAGGCGCTTA ACCTCACCAA TCCCGACAAG ACCCAAGAAT GTTGGCTGTG  2340
CTTAGTGTCG GGACCTCCTT ATTACGAAGG AGTAGCGGTC GTGGGCACTT ATACCAATCA  2400
TTCCACCGCT CCGGCCAACT GTACGGCCAC TTCCCAACAT AAGCTTACCC TATCTGAAGT  2460
GACAGGACAG GGCCTATGCA TGGGGGCAGT ACCTAAAACT CACCAGGCCT TATGTAACAC  2520
CACCCAAAGC GCCGGCTCAG GATCCTACTA CCTTGCAGCA CCCGCCGGAA CAATGTGGGC  2580
TTGCAGCACT GGATTGACTC CCTGCTTGTC CACCACGGTG CTCAATCTAA CCACAGATTA  2640
TTGTGTATTA GTTGAACTCT GGCCCAGAGT AATTTACCAC TCCCCCGATT ATATGTATGG  2700
TCAGCTTGAA CAGCGTACCA AATATAAAAG AGAGCCAGTA TCATTGACCC TGGCCCTTCT  2760
ACTAGGAGGA TTAACCATGG GAGGGATTGC AGCTGGAATA GGGACGGGGA CCACTGCCTT  2820
AATTAAAACC CAGCAGTTTG AGCAGCTTCA TGCCGCTATC CAGACAGACC TCAACGAAGT  2880
CGAAAAGTCA ATTACCAACC TAGAAAAGTC ACTGACCTCG TTGTCTGAAG TAGTCCTACA  2940
GAACCGCAGA GGCCTAGATT TGCTATTCCT AAAGGAGGGA GGTCTCTGCG CAGCCCTAAA  3000
AGAAGAATGT TGTTTTATG CAGACCACAC GGGGCTAGTG AGAGACAGCA TGGCCAAATT  3060
AAGAGAAAGG CTTAATCAGA GACAAAAACT ATTTGAGACA GGCCAAGGAT GGTTCGAAGG  3120
GCTGTTTAAT AGATCCCCCT GGTTTACCAC CTTAATCTCC ACCATCATGG GACCTCTAAT  3180
AGTACTCTTA CTGATCTTAC TCTTTGGACC TTGCATTCTC AATCGATTAG TTCAATTTGT  3240
TAAAGACAGG ATCTCAGTAG TCCAGGCTTT AGTCCTGACT CAACAATACC ACCAGCTAAA  3300
GCCTATAGAG TACGAGCCAT AGGGCGCCTA GTGTTGACAA TTAATCATCG GCATAGTATA  3360
CGGCATAGTA TAATACGACT CACTATAGGA GGGCCACCAT GGCCAAGTTG ACCAGTGCCG  3420
TTCCGGTGCT CACCGCGCGC GACGTCGCCG GAGCGGTCGA GTTCTGGACC GACCGGCTCG  3480
GGTTCTCCCG GGACTTCGTG GAGGACGACT TCGCCGGTGT GGTCCGGGAC GACGTGACCC  3540
TGTTCATCAG CGCGGTCCAG GACCAGGTGG TGCCGGACAA CACCCTGGCC TGGGTGTGGG  3600
TGCGCGGCCT GGACGAGCTG TACGCCGAGT GGTCGGAGGT CGTGTCCACG AACTTCCGGG  3660
ACGCCTCCGG GCCGGCCATG ACCGAGATCG GCGAGCAGCC GTGGGGGCGG GAGTTCGCCC  3720
TGCGCGACCC GGCCGGCAAC TGCGTGCACT TCGTGGCCGA GGAGCAGGAC TGANNNNCGG  3780
ACCGGTCGAC TTGTTAACTT GTTTATTGCA GCTTATAATG GTTACAAATA AAGCAATAGC  3840
ATCACAAATT TCACAAATAA AGCATTTTTT TCACTGCATT CTAGTTGTGG TTTGTCCAAA  3900
CTCATCAATG TATCTTATCA TGTCTGGATC CAGATCTGGG CCCATGCGGC CGCGGATCGA  3960
TNNNNACATG TGAGCAAAAG GCCAGCAAAA GGCCAGGAAC CGTAAAAAGG CCGCGTTGCT  4020
GGCGTTTTTC CATAGGCTCC GCCCCCCTGA CGAGCATCAC AAAAATCGAC GCTCAAGTCA  4080
```

Figure 9b. FBdelPASAF Sequence

```
GAGGTGGCGA AACCCGACAG GACTATAAAG ATACCAGGCG TTTCCCCCTG GAAGCTCCCT      4140
CGTGCGCTCT CCTGTTCCGA CCCTGCCGCT TACCGGATAC CTGTCCGCCT TTCTCCCTTC      4200
GGGAAGCGTG GCGCTTTCTC AATGCTCACG CTGTAGGTAT CTCAGTTCGG TGTAGGTCGT      4260
TCGCTCCAAG CTGGGCTGTG TGCACGAACC CCCCGTTCAG CCCGACCGCT GCGCCTTATC      4320
CGGTAACTAT CGTCTTGAGT CCAACCCGGT AAGACACGAC TTATCGCCAC TGGCAGCAGC      4380
CACTGGTAAC AGGATTAGCA GAGCGAGGTA TGTAGGCGGT GCTACAGAGT TCTTGAAGTG      4440
GTGGCCTAAC TACGGCTACA CTAGAAGGAC AGTATTTGGT ATCTGCGCTC TGCTGAAGCC      4500
AGTTACCTTC GGAAAAAGAG TTGGTAGCTC TTGATCCGGC AAACAAACCA CCGCTGGTAG      4560
CGGTGGTTTT TTTGTTTGCA AGCAGCAGAT TACGCGCAGA AAAAAAGGAT CTCAAGAAGA      4620
TCCTTTGATC TTTTCTACGG GGTCTGACGC TCAGTGGAAC GAAAACTCAC GTTAAGGGAT      4680
TTTGGTCATG AGATTATCAA AAAGGATCTT CACCTAGATC CTTTTAAATT AAAAATGAAG      4740
TTTTAAATCA ATCTAAAGTA TATATGAGTA AACTTGGTCT GACAGTTACC AATGCTTAAT      4800
CAGTGAGGCA CCTATCTCAG CGATCTGTCT ATTTCGTTCA TCCATAGTTG CCTGACTCCC      4860
CGTCGTGTAG ATAACTACGA TACGGGAGGG CTTACCATCT GGCCCCAGTG CTGCAATGAT      4920
ACCGCGAGAC CCACGCTCAC CGGCTCCAGA TTTATCAGCA ATAAACCAGC CAGCCGGAAG      4980
GGCCGAGCGC AGAAGTGGTC CTGCAACTTT ATCCGCCTCC ATCCAGTCTA TTAATTGTTG      5040
CCGGGAAGCT AGAGTAAGTA GTTCGCCAGT TAATAGTTTG CGCAACGTTG TTGCCATTGC      5100
TACAGGCATC GTGGTGTCAC GCTCGTCGTT TGGTATGGCT TCATTCAGCT CCGGTTCCCA      5160
ACGATCAAGG CGAGTTACAT GATCCCCCAT GTTGTGCAAA AAAGCGGTTA GCTCCTTCGG      5220
TCCTCCGATC GTTGTCAGAA GTAAGTTGGC CGCAGTGTTA TCACTCATGG TTATGGCAGC      5280
ACTGCATAAT TCTCTTACTG TCATGCCATC CGTAAGATGC TTTTCTGTGA CTGGTGAGTA      5340
CTCAACCAAG TCATTCTGAG AATAGTGTAT GCGGCGACCG AGTTGCTCTT GCCCGGCGTC      5400
AATACGGGAT AATACCGCGC CACATAGCAG AACTTTAAAA GTGCTCATCA TTGGAAAACG      5460
TTCTTCGGGG CGAAAACTCT CAAGGATCTT ACCGCTGTTG AGATCCAGTT CGATGTAACC      5520
CACTCGTGCA CCCAACTGAT CTTCAGCATC TTTTACTTTC ACCAGCGTTT CTGGGTGAGC      5580
AAAAACAGGA AGGCAAAATG CCGCAAAAAA GGGAATAAGG GCGACACGGA AATGTTGAAT      5640
ACTCATACTC TTCCTTTTTC AATATTATTG AAGCATTTAT CAGGGTTATT GTCTCATGAG      5700
CGGATACATA TTTGAATGTA TTTAGAAAAA TAAACAAATA GGGGTTCCGC GCACATTTCC      5760
CCGAAAAGTG CCACCTGACG TCTAAGAAAC CATTATTATC ATGACATTAA CCTATAAAAA      5820
TAGGCGTATC ACGAGGCCCT TTCGTCTCGC GCGTTTCGGT GATGACGGTG AAAACCTCTG      5880
ACACATGCAG CTCCCGGAGA CGGTCACAGC TTGTCTGTAA GCGGATGCCG GGAGCAGACA      5940
AGCCCGTCAG GGCGCGTCAG CGGGTGTTGG CGGGTGTCGG GCTGGCTTA ACTATGCGGC       6000
ATCAGAGCAG ATTGTACTGA GAGTGCAC                                        6028
```

Figure 10a. FBdelPMOSAF Sequence

```
CATATGCGGT GTGAAATACC GCACAGATGC GTAAGGAGAA AATACCGCAT CAGGCGCCAT      60
TCGCCATTCA GGCTGCGCAA CTGTTGGGAA GGGCGATCGG TGCGGGCCTC TTCGCTATTA     120
CGCCAGCTGG CGAAAGGGGG ATGTGCTGCA AGGCGATTAA GTTGGGTAAC GCCAGGGTTT     180
TCCCAGTCAC GACGTTGTAA AACGACGGCC AGTGAATTCC GATTAGTTCA ATTTGTTAAA     240
GACAGGATCT CAGTAGTCCA GGCTTTAGTC CTGACTCAAC AATACCACCA GCTAAAACCA     300
CTAGAATACG AGCCACAATA AATAAAAGAT TTTATTTAGT TTCCAGAAAA AGGGGGGAAT     360
GAAAGACCCC ACCAAATTGC TTAGCCTGAT AGCCGCAGTA ACGCCATTTT GCAAGGCATG     420
GAAAAATACC AAACCAAGAA TAGAGAAGTT CAGATCAAGG GCGGGTACAC GAAAACAGCT     480
AACGTTGGGC CAAACAGGAT ATCTGCGGTG AGCAGTTTCG GCCCCGGCCC GGGGCCAAGA     540
ACAGATGGTC ACCGCGGTTC GGCCCCGGCC CGGGGCCAAG AACAGATGGT CCCCAGATAT     600
GGCCCAACCC TCAGCAGTTT CTTAAGACCC ATCAGATGTT TCCAGGCTCC CCCAAGGACC     660
TGAAATGACC CTGTGCCTTA TTTGAATTAA CCAATCAGCC TGCTTCTCGC TTCTGTTCGC     720
GCGCTTCTGC TTCCCGAGCT CTATAAAGA GCTCACAACC CCTCACTCGG CGCGCCAGTC     780
CTCCGATAGA CTGAGTCGCC CGGGTACCCG TGTATCCAAT AAATCCTCTT GCTGTTGCAT     840
CCGACTCGTG GTCTCGCTGT TCCTTGGGAG GGTCTCCTCA GAGTGATTGA CTACCCGTCT     900
CGGGGGTCTT TCATTTGGGG GCTCGTCCGG GATCTGGAGA CCCCTGCCCA GGGACCACCG     960
ACCCACCACC GGGAGGTAAG CTGGCCAAGA TCTTATATGG GGCACCCCCG CCCCTTGTAA    1020
ACTTCCCTGA CCCTGACATG ACAAGAGTTA CTAACAGCCC CTCTCTCCAA GCTCACTTAC    1080
AGGCTCTCTA CTTAGTCCAG CACGAAGTCT GGAGACCTCT GGCGGCAGCC TACCAAGAAC    1140
AACTGGACCG ACCGGTGGTA CCTCACCCTT ACCGAGTCGG CGACACAGTG TGGGTCCGCC    1200
GACACCAGAC TAAGAACCTA GAACCTCGCT GGAAAGGACC TTACACAGTC CTGCTGACCA    1260
CCCCCACCGC CCTCAAAGTA GACGGCATCG CAGCTTGGAT ACACGCCGCC CACGTGAAGG    1320
CTGCCGACCC CGGGGGTGGA CCATCCTCTA GACTGACATG GCGCGTTCAA CGCTCTCAAA    1380
ACCCCTTAAA AATAAGGTTA ACCCGCGAGG CCCCCTAATC CCCTTAATTC TTCTGATGCT    1440
CAGAGGGGTC AGTACTGCTT CGCCCGGCTC CAGTCCTCAT CAAGTCTATA ATATCACCTG    1500
GGAGGTAACC AATGGAGATC GGGAGACGGT ATGGGCAACT TCTGGCAACC ACCCTCTGTG    1560
GACCTGGTGG CCTGACCTTA CCCCAGATTT ATGTATGTTA GCCCACCATG GACCATCTTA    1620
TTGGGGGCTA GAATATCAAT CCCCTTTTTC TTCTCCCCCG GGGCCCCCTT GTTGCTCAGG    1680
GGGCAGCAGC CCAGGCTGTT CCAGAGACTG CGAAGAACCT TTAACCTCCC TCACCCCTCG    1740
GTGCAACACT GCCTGGAACA GACTCAAGCT AGACCAGACA ACTCATAAAT CAAATGAGGG    1800
ATTTTATGTT TGCCCCGGGC CCCACCGCCC CCGAGAATCC AAGTCATGTG GGGGTCCAGA    1860
CTCCTTCTAC TGTGCCTATT GGGGCTGTGA GACAACCGGT AGAGCTTACT GGAAGCCCTC    1920
CTCATCATGG GATTTCATCA CAGTAAACAA CAATCTCACC TCTGACCAGG CTGTCCAGGT    1980
ATGCAAAGAT AATAAGTGGT GCAACCCCTT AGTTATTCGG TTTACAGACG CCGGGAGACG    2040
GGTTACTTCC TGGACCACAG GACATTACTG GGGCTTACGT TTGTATGTCT CCGGACAAGA    2100
TCCAGGGCTT ACATTTGGGA TCCGACTCAG ATACCAAAAT CTAGGACCCC GCGTCCCAAT    2160
AGGGCCAAAC CCCGTTCTGG CAGACCAACA GCCACTCTCC AAGCCCAAAC CTGTTAAGTC    2220
GCCTTCAGTC ACCAAACCAC CCAGTGGGAC TCCTCTCTCC CCTACCCAAC TTCCACCGGC    2280
GGGAACGGAA AATAGGCTGC TAAACTTAGT AGACGGAGCC TACCAAGCCC TCAACCTCAC    2340
CAGTCCTGAC AAAACCCAAG AGTGCTGGTT GTGTCTAGTA GCGGGACCCC CCTACTACGA    2400
AGGGGTTGCC GTCCTGGGTA CCTACTCCAA CCATACCTCT GCTCCAGCCA ACTGCTCCGT    2460
GGCCTCCCAA CACAAGTTGA CCCTGTCCGA AGTGACCGGA CAGGGACTCT GCATAGGAGC    2520
AGTTCCCAAA ACACATCAGG CCCTATGTAA TACCACCCAG ACAAGCAGTC GAGGGTCCTA    2580
TTATCTAGTT GCCCCTACAG GTACCATGTG GGCTTGTAGT ACCGGGCTTA CTCCATGCAT    2640
CTCCACCACC ATACTGAACC TTACCACTGA TTATTGTGTT CTTGTCGAAC TCTGGCCAAG    2700
AGTCACCTAT CATTCCCCCA GCTATGTTTA CGGCCTGTTT GAGAGATCCA ACCGACACAA    2760
AAGAGAACCG GTGTCGTTAA CCCTGGCCCT ATTATTGGGT GGACTAACCA TGGGGGGAAT    2820
TGCCGCTGGA ATAGGAACAG GGACTACTGC TCTAATGGCC ACTCAGCAAT TCCAGCAGCT    2880
CCAAGCCGCA GTACAGGATG ATCTCAGGGA GGTTGAAAAA TCAATCTCTA ACCTAGAAAA    2940
GTCTCTCACT TCCCTGTCTG AAGTTGTCCT ACAGAATCGA AGGGGCCTAG ACTTGTTATT    3000
TCTAAAAGAA GGAGGGCTGT GTGCTGCTCT AAAAGAAGAA TGTTGCTTCT ATGCGGACCA    3060
CACAGGACTA GTGAGAGACA GCATGGCCAA ATTGAGAGAG AGGCTTAATC AGAGACAGAA    3120
ACTGTTTGAG TCAACTCAAG GATGGTTTGA GGGACTGTTT AACAGATCCC CTTGGTTTAC    3180
CACCTTGATA TCTACCATTA TGGGACCCCT CATTGTACTC CTAATGATTT TGCTCTTCGG    3240
ACCCTGCATT CTTAATCGAT TAGTTCAATT TGTTAAAGAC AGGATCTCAG TAGTCCAGGC    3300
TTTAGTCCTG ACTCAACAAT ACCACCAGCT AAAGCCTATA GAGTACGAGC CATAGGGCGC    3360
CTAGTGTTGA CAATTAATCA TCGCATAGT ATACGCATA GTATAATACG ACTCACTATA    3420
GGAGGGCCAC CATGGCCAAG TTGACCAGTG CCGTTCCGGT GCTCACCGCG CGCGACGTCG    3480
CCGGAGCGGT CGAGTTCTGG ACCGACCGGC TCGGGTTCTC CCGGGACTTC GTGGAGGACG    3540
ACTTCGCCGG TGTGGTCCGG GACGACGTGA CCCTGTTCAT CAGCGCGGTC AGGACCAGG    3600
TGGTGCCGGA CAACACCCTG GCCTGGGTGT GGGTGCGCGG CCTGGACGAG CTGTACGCCG    3660
AGTGGTCGGA GGTCGTGTCC ACGAACTTCC GGGACGCCTC CGGGCCGGCC ATGACCGAGA    3720
TCGGCGAGCA GCCGTGGGGG CGGGAGTTCG CCCTGCGCGA CCCGGCCGGC AACTGCGTGC    3780
ACTTCGTGGC CGAGGAGCAG GACTGANNNN CGGACCGGTC GACTTGTTAA CTTGTTTATT    3840
GCAGCTTATA ATGGTTACAA ATAAAGCAAT AGCATCACAA ATTTCACAAA TAAAGCATTT    3900
TTTTCACTGC ATTCTAGTTG TGGTTTGTCC AAACTCATCA ATGTATCTTA TCATGTCTGG    3960
ATCCAGATCT GGGCCCATGC GGCCGCGGAT CGATNNNNAC ATGTGAGCAA AAGGCCAGCA    4020
AAAGGCCAGG AACCGTAAAA AGGCCGCGTT GCTGGCGTTT TTCCATAGGC TCCGCCCCCC    4080
```

Figure 10b. FBdelPMOSAF Sequence

```
TGACGAGCAT CACAAAAATC GACGCTCAAG TCAGAGGTGG CGAAACCCGA CAGGACTATA    4140
AAGATACCAG GCGTTTCCCC CTGGAAGCTC CCTCGTGCGC TCTCCTGTTC CGACCCTGCC    4200
GCTTACCGGA TACCTGTCCG CCTTTCTCCC TTCGGGAAGC GTGGCGCTTT CTCAATGCTC    4260
ACGCTGTAGG TATCTCAGTT CGGTGTAGGT CGTTCGCTCC AAGCTGGGCT GTGTGCACGA    4320
ACCCCCCGTT CAGCCCGACC GCTGCGCCTT ATCCGGTAAC TATCGTCTTG AGTCCAACCC    4380
GGTAAGACAC GACTTATCGC CACTGGCAGC AGCCACTGGT AACAGGATTA GCAGAGCGAG    4440
GTATGTAGGC GGTGCTACAG AGTTCTTGAA GTGGTGGCCT AACTACGGCT ACACTAGAAG    4500
GACAGTATTT GGTATCTGCG CTCTGCTGAA GCCAGTTACC TTCGGAAAAA GAGTTGGTAG    4560
CTCTTGATCC GGCAAACAAA CCACCGCTGG TAGCGGTGGT TTTTTTGTTT GCAAGCAGCA    4620
GATTACGCGC AGAAAAAAAG GATCTCAAGA AGATCCTTTG ATCTTTTCTA CGGGGTCTGA    4680
CGCTCAGTGG AACGAAAACT CACGTTAAGG GATTTTGGTC ATGAGATTAT CAAAAAGGAT    4740
CTTCACCTAG ATCCTTTTAA ATTAAAAATG AAGTTTTAAA TCAATCTAAA GTATATATGA    4800
GTAAACTTGG TCTGACAGTT ACCAATGCTT AATCAGTGAG GCACCTATCT CAGCGATCTG    4860
TCTATTTCGT TCATCCATAG TTGCCTGACT CCCCGTCGTG TAGATAACTA CGATACGGGA    4920
GGGCTTACCA TCTGGCCCCA GTGCTGCAAT GATACCGCCA GACCCACGCT CACCGGCTCC    4980
AGATTTATCA GCAATAAACC AGCCAGCCGG AAGGGCCGAG CGCAGAAGTG GTCCTGCAAC    5040
TTTATCCGCC TCCATCCAGT CTATTAATTG TTGCCGGGAA GCTAGAGTAA GTAGTTCGCC    5100
AGTTAATAGT TTGCGCAACG TTGTTGCCAT TGCTACAGGC ATCGTGGTGT CACGCTCGTC    5160
GTTTGGTATG GCTTCATTCA GCTCCGGTTC CCAACGATCA AGGCGAGTTA CATGATCCCC    5220
CATGTTGTGC AAAAAAGCGG TTAGCTCCTT CGGTCCTCCG ATCGTTGTCA GAAGTAAGTT    5280
GGCCGCAGTG TTATCACTCA TGGTTATGGC AGCACTGCAT AATTCTCTTA CTGTCATGCC    5340
ATCCGTAAGA TGCTTTTCTG TGACTGGTGA GTACTCAACC AAGTCATTCT GAGAATAGTG    5400
TATGCGGCGA CCGAGTTGCT CTTGCCCGGC GTCAATACGG GATAATACCG CGCCACATAG    5460
CAGAACTTTA AAAGTGCTCA TCATTGGAAA ACGTTCTTCG GGGCGAAAAC TCTCAAGGAT    5520
CTTACCGCTG TTGAGATCCA GTTCGATGTA ACCCACTCGT GCACCCAACT GATCTTCAGC    5580
ATCTTTTACT TTCACCAGCG TTTCTGGGTG AGCAAAAACA GGAAGGCAAA ATGCCGCAAA    5640
AAAGGGAATA AGGGCGACAC GGAAATGTTG AATACTCATA CTCTTCCTTT TTCAATATTA    5700
TTGAAGCATT TATCAGGGTT ATTGTCTCAT GAGCGGATAC ATATTTGAAT GTATTTAGAA    5760
AAATAAACAA ATAGGGGTTC CGCGCACATT TCCCCGAAAA GTGCCACCTG ACGTCTAAGA    5820
AACCATTATT ATCATGACAT TAACCTATAA AAATAGGCGT ATCACGAGGC CCTTTCGTCT    5880
CGCGCGTTTC GGTGATGACG GTGAAAACCT CTGACACATG CAGCTCCCGG AGACGGTCAC    5940
AGCTTGTCTG TAAGCGGATG CCGGGAGCAG ACAAGCCCGT CAGGGCGCGT CAGCGGGTGT    6000
TGGCGGGTGT CGGGGCTGGC TTAACTATGC GGCATCAGAG CAGATTGTAC TGAGAGTGCA    6060
C                                                                    6061
```

Figure 11a. FBdelPGASAF Sequence

```
CATATGCGGT GTGAAATACC GCACAGATGC GTAAGGAGAA AATACCGCAT CAGGCGCCAT    60
TCGCCATTCA GGCTGCGCAA CTGTTGGGAA GGGCGATCGG TGCGGGCCTC TTCGCTATTA   120
CGCCAGCTGG CGAAAGGGGG ATGTGCTGCA AGGCGATTAA GTTGGGTAAC GCCAGGGTTT   180
TCCCAGTCAC GACGTTGTAA AACGACGGCC AGTGAATTCC GATTAGTTCA ATTTGTTAAA   240
GACAGGATCT CAGTAGTCCA GGCTTTAGTC CTGACTCAAC AATACCACCA GCTAAAACCA   300
CTAGAATACG AGCCACAATA AATAAAAGAT TTTATTTAGT TTCCAGAAAA AGGGGGGAAT   360
GAAAGACCCC ACCAAATTGC TTAGCCTGAT AGCCGCAGTA ACGCCATTTT GCAAGGCATG   420
GAAAAATACC AAACCAAGAA TAGAGAAGTT CAGATCAAGG GCGGGTACAC GAAAACAGCT   480
AACGTTGGGC CAAACAGGAT ATCTGCGGTG AGCAGTTTCG GCCCCGGCCC GGGGCCAAGA   540
ACAGATGGTC ACCGCGGTTC GGCCCCGGCC CGGGGCCAAG AACAGATGGT CCCCAGATAT   600
GGCCCAACCC TCAGCAGTTT CTTAAGACCC ATCAGATGTT CCAGGCTCC  CCCAAGGACC   660
TGAAATGACC CTGTGCCTTA TTTGAATTAA CCAATCAGCC TGCTTCTCGC TTCTGTTCGC   720
GCGCTTCTGC TTCCCGAGCT CTATAAAAGA GCTCACAACC CCTCACTCGG CGCGCCAGTC   780
CTCCGATAGA CTGAGTCGCC CGGGTACCCG TGTATCCAAT AAATCCTCTT GCTGTTGCAT   840
CCGACTCGTG GTCTCGCTGT TCCTTGGGAG GGTCTCCTCA GAGTGATTGA CTACCCGTCT   900
CGGGGGTCTT TCATTTGGGG GCTCGTCCGG GATCTGGAGA CCCCTGCCCA GGGACCACCG   960
ACCCACCACC GGGAGGTAAG CTGGCCAAGA TCCCTAAGGT ACTCGGGTCA GACAATGGCC  1020
CGGCCTTTGT TGCTCAGGTA AGTCAGGGAC TGGCCACTCA ACTGGGGATA AATTGGAAGT  1080
TACATTGTGC GTATAGACCC CAGAGCTCAG GTCAGGTAGA AAGAATGAAC AGAACAATTA  1140
AAGAGACCTT GACCAAATTA GCCTTAGAGA CCGGTGGAAA AGACTGGGTG ACCCTCCTTC  1200
CCTTAGCGCT GCTTAGGGCC AGGAATACCC CTGGCCGGTT TGGTTTAACT CCTTATGAAA  1260
TTCTCTATGG AGGACCACCC CCCATACTTG AGTCTGGAGA AACTTTGGGT CCCGATGATA  1320
GATTTCTCCC TGTCTTATTT ACTCACTTAA AGGCTTTAGA AATTGTAAGG ACCCAAATCT  1380
GGGACCAGAT CAAAGAGGTG TATAAGCCTG GTACCGTAAC AATCCCTCAC CCGTTCCAGG  1440
TCGGGGATCA AGTGCTTGTC AGACGCCATC GACCCAGCAG CCTTGAGCCT CGGTGGAAAG  1500
GCCCATACCT GGTGTTGCTG ACTACCCCGA CCGCGGTAAA AGTCGATGGT ATTGCTGCCT  1560
GGGTCCATGC TTCTCACCTC AAACCTGCAC CACCTTCGGC ACCAGATGAG TCCTGGGAGC  1620
TGGAAAAGAC TGATCATCCT CTTAAGCTGC GTATTCGGCG GCGGCGGGAC GAGTCTGCAA  1680
AATAAGAACC CCCACCAGCC CATGACCCTC ACTTGGCAGG TACTGTCCCA AACTGGAGAC  1740
GTTGTCTGGG ATACAAAGGC AGTCCAGCCC CTTGGACTT  GGTGGCCCAC ACTTAAACCT  1800
GATGTATGTG CCTTGGCGGC TAGTCTTGAG TCCTGGGATA TCCCGGGAAC CGATGTCTCG  1860
TCCTCTAAAC GAGTCAGACC TCCGGACTCA GACTATACTG CCGCTTATAA GCAAATCACC  1920
TGGGGAGCCA TAGGGTGCAG CTACCCTCGG GCTAGGACTA GAATGGCAAG CTCTACCTTC  1980
TACGTATGTC CCCGGGATGG CCGGACCCTT TCAGAAGCTA GAAGGTGCGG GGGGCTAGAA  2040
TCCCTATACT GTAAAGAATG GGATTGTGAG ACCACGGGGA CCGGTTATTG GCTATCTAAA  2100
TCCTCAAAAG ACCTCATAAC TGTAAAATGG GACCAAAATA GCGAATGGAC TCAAAAATTT  2160
CAACAGTGTC ACCAGACCGG CTGGTGTAAC CCCCTTAAAA TAGATTTCAC AGACAAAGGA  2220
AAATTATCCA AGGACTGGAT AACGGGAAAA ACCTGGGGAT TAAGATTCTA TGTGTCTGGA  2280
CATCCAGGCG TACAGTTCAC CATTCGCTTA AAAATCACCA ACATGCCAGC TGTGGCAGTA  2340
GGTCCTGACC TCGTCCTTGT GGAACAAGGA CCTCCTAGAA CGTCCCTCGC TCTCCCACCT  2400
CCTCTTCCCC CAAGGGAAGC GCCACCGCCA TCTCTCCCCG ACTCTAACTC CACAGCCCTG  2460
GCGACTAGTG CACAAACTCC CACGGTGAGA AAAACAATTG TTACCCTAAA CACTCCGCCT  2520
CCCACCACAG GCGACAGACT TTTTGATCTT GTGCAGGGGG CCTTCCTAAC CTTAAATGCT  2580
ACCAACCAG GGGCCACTGA GTCTTGCTGG CTTTGTTTGG CCATGGGCCC CCCTTATTAT  2640
GAAGCAATAG CCTCATCAGG AGAGGTCGCC TACTCCACCG ACCTTGACCG GTGCCGCTGG  2700
GGGACCCAAG GAAAGCTCAC CCTCACTGAG GTCTCAGGAC ACGGGTTGTG CATAGGAAAG  2760
GTGCCCTTTA CCCATCAGCA TCTCTGCAAT CAGACCCTAT CCATCAATTC CTCCGGAGAC  2820
CATCAGTATC TGCTCCCCTC CAACCATAGC TGGTGGGCTT GCAGCACTGG CCTCACCCCT  2880
TGCCTCTCCA CCTCAGTTTT TAATCAGACT AGAGATTTCT GTATCCAGGT CCAGCTGATT  2940
CCTCGCATCT ATTACTATCC TGAAGAAGTT TTGTTACAGG CCTATGACAA TTCTCACCCC  3000
AGGACTAAAA GAGAGGCTGT CTCACTTACC CTAGCTGTTT TACTGGGAAT CACG         3060
GCGGGAATAG GTACTGGTTC AACTGCCTTA ATTAAGGAC CTATAGACCT CCAGCAAGGC  3120
CTGACAAGCC TCCAGATCGC CATAGATGCT GACCTCCGGG CCCTCCAAGA CTCAGTCAGC  3180
AAGTTAGAGG ACTCACTGAC TTCCCTGTCC GAGGTAGTGC TCCAAAATAG GAGAGGCCTT  3240
GACTTGCTGT TTCTAAAAGA AGGTGGCCTC TGTGCGGCCC TAAAGGAAGA GTGCTGTTTT  3300
TACATAGACC ACTCAGGTGC AGTACGGGAC TCCATGAAAA AACTCAAAGA AAAACTGGAT  3360
AAAAGACAGT TAGAGCGCCA GAAAAGCCAA AACTGGTATG AAGGATGGTT CAATAACTCC  3420
CCTTGGTTCA CTACCCTGCT ATCAACCATC GCTGGGCCCC TATTACTCCT CCTTCTGTTG  3480
CTCATCCTCG GGCCATGCAT CATCAATCGA TTAGTTCAAT TTGTTAAAGA CAGGATCTCA  3540
GTAGTCCAGG CTTTAGTCCT GACTCAACAA TACCACCAGC TAAAGCCTAT AGAGTACGAG  3600
CCATAGGGCG CCTAGTGTTG ACAATTAATC ATCGGCATAG TATACGGCAT AGTATAATAC  3660
GACTCACTAT AGGAGGGCCA CCATGGCCAA GTTGACCAGT GCCGTTCCG  TGCTCACCGC  3720
GCGCGACGTC GCCGGAGCGG TCGAGTTCTG GACCGACCGG CTCGGGTTCT CCCGGGACTT  3780
CGTGGAGGAC GACTTCGCCG GTGTGGTCCG GGACGACGTG ACCCTGTTCA TCAGCGCGGT  3840
CCAGGACCAG GTGGTGCCGG ACAACACCCT GGCCTGGGTG TGGGTGCGCG GCCTGGACGA  3900
GCTGTACGCC GAGTGGTCGG AGGTCGTGTC CACGAACTTC CGGGACGCCT CCGGGCCGGC  3960
CATGACCGAG ATCGGCGAGC AGCCGTGGGG GCGGGAGTTC GCCCTGCGCG ACCCGGCCGG  4020
CAACTGCGTG CACTTCGTGG CCGAGGAGCA GGACTGANNN NCGGACCGGT CGACTTGTTA  4080
```

Figure 11b. FBdelPGASAF Sequence

```
ACTTGTTTAT TGCAGCTTAT AATGGTTACA AATAAAGCAA TAGCATCACA AATTTCACAA      4140
ATAAAGCATT TTTTTCACTG CATTCTAGTT GTGGTTTGTC CAAACTCATC AATGTATCTT      4200
ATCATGTCTG GATCCAGATC TGGGCCCATG CGGCCGCGGA TCGATNNNNA CATGTGAGCA      4260
AAAGGCCAGC AAAAGGCCAG GAACCGTAAA AAGGCCGCGT TGCTGGCGTT TTTCCATAGG      4320
CTCCGCCCCC CTGACGAGCA TCACAAAAAT CGACGCTCAA GTCAGAGGTG GCGAAACCCG      4380
ACAGGACTAT AAAGATACCA GGCGTTTCCC CCTGGAAGCT CCCTCGTGCG CTCTCCTGTT      4440
CCGACCCTGC CGCTTACCGG ATACCTGTCC GCCTTTCTCC CTTCGGGAAG CGTGGCGCTT      4500
TCTCAATGCT CACGCTGTAG GTATCTCAGT TCGGTGTAGG TCGTTCGCTC CAAGCTGGGC      4560
TGTGTGCACG AACCCCCCGT TCAGCCCGAC CGCTGCGCCT TATCCGGTAA CTATCGTCTT      4620
GAGTCCAACC CGGTAAGACA CGACTTATCG CCACTGGCAG CAGCCACTGG TAACAGGATT      4680
AGCAGAGCGA GGTATGTAGG CGGTGCTACA GAGTTCTTGA AGTGGTGGCC TAACTACGGC      4740
TACACTAGAA GGACAGTATT TGGTATCTGC GCTCTGCTGA AGCCAGTTAC CTTCGGAAAA      4800
AGAGTTGGTA GCTCTTGATC CGGCAAACAA ACCACCGCTG GTAGCGGTGG TTTTTTTGTT      4860
TGCAAGCAGC AGATTACGCG CAGAAAAAAA GGATCTCAAG AAGATCCTTT GATCTTTTCT      4920
ACGGGGTCTG ACGCTCAGTG GAACGAAAAC TCACGTTAAG GGATTTTGGT CATGAGATTA      4980
TCAAAAGGA TCTTCACCTA GATCCTTTTA AATTAAAAAT GAAGTTTTAA ATCAATCTAA      5040
AGTATATATG AGTAAACTTG GTCTGACAGT TACCAATGCT TAATCAGTGA GGCACCTATC      5100
TCAGCGATCT GTCTATTTCG TTCATCCATA GTTGCCTGAC TCCCCGTCGT GTAGATAACT      5160
ACGATACGGG AGGGCTTACC ATCTGGCCCC AGTGCTGCAA TGATACCGCG AGACCCACGC      5220
TCACCGGCTC CAGATTTATC AGCAATAAAC CAGCCAGCCG GAAGGGCCGA GCGCAGAAGT      5280
GGTCCTGCAA CTTTATCCGC CTCCATCCAG TCTATTAATT GTTGCCGGGA AGCTAGAGTA      5340
AGTAGTTCGC CAGTTAATAG TTTGCGCAAC GTTGTTGCCA TTGCTACAGG CATCGTGGTG      5400
TCACGCTCGT CGTTTGGTAT GGCTTCATTC AGCTCCGGTT CCCAACGATC AAGGCGAGTT      5460
ACATGATCCC CCATGTTGTG CAAAAAAGCG GTTAGCTCCT TCGGTCCTCC GATCGTTGTC      5520
AGAAGTAAGT TGGCCGCAGT GTTATCACTC ATGGTTATGG CAGCACTGCA TAATTCTCTT      5580
ACTGTCATGC CATCCGTAAG ATGCTTTTCT GTGACTGGTG AGTACTCAAC CAAGTCATTC      5640
TGAGAATAGT GTATGCGGCG ACCGAGTTGC TCTTGCCCGG CGTCAATACG GGATAATACC      5700
GCGCCACATA GCAGAACTTT AAAAGTGCTC ATCATTGGAA AACGTTCTTC GGGGCGAAAA      5760
CTCTCAAGGA TCTTACCGCT GTTGAGATCC AGTTCGATGT AACCCACTCG TGCACCCAAC      5820
TGATCTTCAG CATCTTTTAC TTTCACCAGC GTTTCTGGGT GAGCAAAAAC AGGAAGGCAA      5880
AATGCCGCAA AAAAGGGAAT AAGGGCGACA CGGAAATGTT GAATACTCAT ACTCTTCCTT      5940
TTTCAATATT ATTGAAGCAT TTATCAGGGT TATTGTCTCA TGAGCGGATA CATATTTGAA      6000
TGTATTTAGA AAAATAAACA AATAGGGGTT CCGCGCACAT TTCCCCGAAA AGTGCCACCT      6060
GACGTCTAAG AAACCATTAT TATCATGACA TTAACCTATA AAAATAGGCG TATCACGAGG      6120
CCCTTTCGTC TCGCGCGTTT CGGTGATGAC GGTGAAAACC TCTGACACAT GCAGCTCCCG      6180
GAGACGGTCA CAGCTTGTCT GTAAGCGGAT GCCGGGAGCA GACAAGCCCG TCAGGGCGCG      6240
TCAGCGGGTG TTGGCGGGTG TCGGGCTGG CTTAACTATG CGGCATCAGA GCAGATTGTA      6300
CTGAGAGTGC AC                                                          6312
```

Figure 12a. FBdelPRDSAF Sequence

```
CATATGCGGT GTGAAATACC GCACAGATGC GTAAGGAGAA AATACCGCAT CAGGCGCCAT    60
TCGCCATTCA GGCTGCGCAA CTGTTGGGAA GGGCGATCGG TGCGGGCCTC TTCGCTATTA   120
CGCCAGCTGG CGAAAGGGGG ATGTGCTGCA AGGCGATTAA GTTGGGTAAC GCCAGGGTTT   180
TCCCAGTCAC GACGTTGTAA AACGACGGCC AGTGAATTCC GATTAGTTCA ATTTGTTAAA   240
GACAGGATCT CAGTAGTCCA GGCTTTAGTC CTGACTCAAC AATACCACCA GCTAAAACCA   300
CTAGAATACG AGCCACAATA AATAAAAGAT TTTATTTAGT TTCCAGAAAA AGGGGGAAT    360
GAAAGACCCC ACCAAATTGC TTAGCCTGAT AGCCGCAGTA ACGCCATTTT GCAAGGCATG   420
GAAAAATACC AAACCAAGAA TAGAGAAGTT CAGATCAAGG GCGGGTACAC GAAAACAGCT   480
AACGTTGGGC CAAACAGGAT ATCTGCGGTG AGCAGTTTCG GCCCCGGCCC GGGGCCAAGA   540
ACAGATGGTC ACCGCGGTTC GGCCCCGGCC CGGGGCCAAG AACAGATGGT CCCCAGATAT   600
GGCCCAACCC TCAGCAGTTT CTTAAGACCC ATCAGATGTT TCCAGGCTCC CCCAAGGACC   660
TGAAATGACC CTGTGCCTTA TTTGAATTAA CCAATCAGCC TGCTTCTCGC TTCTGTTCGC   720
GCGCTTCTGC TTCCCGAGCT CTATAAAAGA GCTCACAACC CCTCACTCGG CGCGCCAGTC   780
CTCCGATAGA CTGAGTCGCC CGGGTACCCG TGTATCCAAT AAATCCTCTT GCTGTTGCAT   840
CCGACTCGTG GTCTCGCTGT TCCTTGGGAG GGTCTCCTCA GAGTGATTGA CTACCCGTCT   900
CGGGGGTCTT TCATTTGGGG GCTCGTCCGG GATCTGGAGA CCCCTGCCCA GGGACCACCG   960
ACCCACCACC GGGAGGTAAG CTGGCCAAGA TCCCCGGGC TGCAGGAATT TATGAAATCC  1020
TTTATGGGGG ACCCCCCCCT TTGTCAACCT TGCTCAATTC CTTCTCCCCC TCCGATCCTA  1080
AGACTGATTT ACAAGCCCGA CTAAAAGGGC TGCAAGGCGT GCAGGCCCAA ATCTGGACAC  1140
CCCTGGCCGA ATTGTACCGG CCAGGACATC CACAAACTAG CCACCCATTT CAGGTGGGAG  1200
ACTCCGTGTA CGTCCGGCGG CACCGCTCTC AAGGATTGGA GCCTCGTTGG AAGGGACCTT  1260
ACATCGTCCT GCTGACCACG CCCACCGCCA TAAAGGTTGA CGGGATCGCC GCCTGGATTC  1320
ACGCATCGCA CGCCAAGGCA GCCCCAAAAA CCCCTGGACC AGAAACTCCC AAAACCTGGA  1380
AGCTCCGCCG TTCGGAGAAC CCTCTTAAGA TAAGACTCTC CCGTGTCTGA CTGCTAATCC  1440
ACCTTGTCCC TGTACTAACC CAAAATGAAA CTCCCAACAG GAATGGTCAT TTTATGTAGC  1500
CTAATAATAG TTCGGGCAGG GTTTGACGAC CCCCGCAAGG CTATCGCATT AGTACAAAAA  1560
CAACATGGTA AACCATGCGA ATGCAGCGGA GGGCAGGTAT CCGAGGCCCC ACCGAACTCC  1620
ATCCAACAGG TAACTTGCCC AGGCAAGACG GCCTACTTAA TGACCAACCA AAAATGGAAA  1680
TGCAGAGTCA CTCCAAAAAT CTCACCTAGC GGGGGAGAAC TCCAGAACTG CCCCTGTAAC  1740
ACTTTCCAGG ACTCGATGCA CAGTTCTTGT TATACTGAAT ACCGGCAATG CAGGCGAATT  1800
AATAAGACAT ACTACACGGC CACCTTGCTT AAAATACGGT CTGGGAGCCT CAACGAGGTA  1860
CAGATATTAC AAAACCCCAA TCAGCTCCTA CAGTCCCCTT GTAGGGGCTC TATAAATCAG  1920
CCCGTTTGCT GGAGTGCCAC AGCCCCCATC CATATCTCCG ATGGTGGAGG ACCCCTCGAT  1980
ACTAAGAGAG TGTGGACAGT CCAAAAAAGG CTAGAACAAA TTCATAAGGC TATGACTCCT  2040
GAACTTCAAT ACCACCCCTT AGCCCTGCCC AAAGTCAGAG ATGACCTTAG CCTTGATGCA  2100
CGGACTTTTG ATATCCTGAA TACCACTTTT AGGTTACTCC AGATGTCCAA TTTTAGCCTT  2160
GCCCAAGATT GTTGGCTCTG TTTAAAACTA GGTACCCCTA CCCCTCTTGC GATACCCACT  2220
CCCTCTTTAA CCTACTCCCT AGCAGACTCC CTAGCGAATG CCTCCTGTCA GATTATACCT  2280
CCCCTCTTGG TTCAACCGAT GCAGTTCTCC AACTCGTCCT GTTTATCTTC CCCTTTCATT  2340
AACGATACGG AACAAATAGA CTTAGGTGCA GTCACCTTTA CTAACTGCAC CTCTGTAGCC  2400
AATGTCAGTA GTCCTTTATG TGCCCTAAAC GGGTCAGTCT TCCTCTGTGG AAATAACATG  2460
GCATACACCT ATTTACCCCA AAACTGGACC AGACTTTGCG TCCAAGCCTC CCTCCTCCCC  2520
GACATTGACA TCAACCCGGG GGATGAGCCA GTCCCCATTC CTGCCATTGA TCATTATATA  2580
CATAGACCTA AACGAGCTGT ACAGTTCATC CCTTTACTAG CTGGACTGGG AATCACCGCA  2640
GCATTCACCA CCGGAGCTAC AGGCCTAGGT GTCTCCGTCA CCCAGTATAC AAAATTATCC  2700
CATCAGTTAA TATCTGATGT CCAAGTCTTA TCCGGTACCA TACAAGATTT ACAAGACCAG  2760
GTAGACTCGT TAGCTGAAGT AGTTCTCCAA AATAGGAGGG GACTGGACCT ACTAACGGCA  2820
GAACAAGGAG GAATTTGTTT AGCCTTACAA GAAAAATGCT GTTTTTATGC TAACAAGTCA  2880
GGAATTGTGA GAAACAAAAT AAGAACCCTA CAAGAAGAAT TACAAAAACG CAGGGAAAGC  2940
CTGCAACCA ACCCTCTCTG GACCGGGCTG CAGGGCTTTC TTCCGTACCT CCTACCTCTC  3000
CTGGGACCCC TACTCACCCT CCTACTCATA CTAACCATTG GGCCATGCGT TTTCAGTCGC  3060
CTCATGGCCT TCATTAATGA TAGACTTAAT GTTGTACATG CCATGGTGCT GGCCCAGCAA  3120
TACCAAGCAC TCAAAGCTGA GGAAGAAGCT CAGGATTGAG GCGCCTAGTG TTGACAATTA  3180
ATCATCGGCA TAGTATACGG CATAGTATAA TACGACTCAC TATAGGAGGG CCACCATGGC  3240
CAAGTTGACC AGTGCCGTTC CGGTGCTCAC CGCGCGCGAC GTCGCCGGAG CGGTCGAGTT  3300
CTGGACCGAC CGGCTCGGGT TCTCCCGGGA CTTCGTGGAG GACGACTTCG CCGGTGTGGT  3360
CCGGGACGAC GTGACCCTGT TCATCAGCGC GGTCCAGGAC CAGGTGGTGC CGGACAACAC  3420
CCTGGCCTGG GTGTGGGTGC GCGGCCTGGA CGAGCTGTAC GCCGAGTGGT CGGAGGTCGT  3480
GTCCACGAAC TTCCGGGACG CCTCCGGGCC GGCCATGACC GAGATCGGCG AGCAGCCGTG  3540
GGGGCGGGAG TTCGCCCTGC GCGACCCGGC CGGCAACTGC GTGCACTTCG TGGCCGAGGA  3600
GCAGGACTGA NNNNCGGACC GGTCGACTTG TTAACTTGTT TATTGCAGCT TATAATGGTT  3660
ACAAATAAAG CAATAGCATC ACAAATTTCA CAAATAAAGC ATTTTTTTCA CTGCATTCTA  3720
GTTGTGGTTT GTCCAAACTC ATCAATGTAT CTTATCATGT CTGGATCGAT ATCTGGGCCC  3780
ATGCGGCCGC GGATCGATNN NNACATGTGA GCAAAAGGCC AGCAAAAGGC CAGGAACCGT  3840
AAAAAGGCCG CGTTGCTGGC GTTTTTCCAT AGGCTCCGCC CCCTGACGA GCATCACAAA  3900
AATCGACGCT CAAGTCAGAG GTGGCGAAAC CCGACAGGAC TATAAAGATA CCAGGCGTTT  3960
CCCCCTGGAA GCTCCCTCGT GCGCTCTCCT GTTCCGACCC TGCCGCTTAC CGGATACCTG  4020
TCCGCCTTTC TCCCTTCGGG AAGCGTGGCG CTTTCTCAAT GCTCACGCTG TAGGTATCTC  4080
```

Figure 12b. FBdelPRDSAF Sequence

```
AGTTCGGTGT AGGTCGTTCG CTCCAAGCTG GCTGTGTGC  ACGAACCCCC CGTTCAGCCC     4140
GACCGCTGCG CCTTATCCGG TAACTATCGT CTTGAGTCCA ACCCGGTAAG ACACGACTTA     4200
TCGCCACTGG CAGCAGCCAC TGGTAACAGG ATTAGCAGAG CGAGGTATGT AGGCGGTGCT     4260
ACAGAGTTCT TGAAGTGGTG GCCTAACTAC GGCTACACTA GAAGGACAGT ATTTGGTATC     4320
TGCGCTCTGC TGAAGCCAGT TACCTTCGGA AAAAGAGTTG GTAGCTCTTG ATCCGGCAAA     4380
CAAACCACCG CTGGTAGCGG TGGTTTTTTT GTTTGCAAGC AGCAGATTAC GCGCAGAAAA     4440
AAAGGATCTC AAGAAGATCC TTTGATCTTT TCTACGGGGT CTGACGCTCA GTGGAACGAA     4500
AACTCACGTT AAGGGATTTT GGTCATGAGA TTATCAAAAA GGATCTTCAC CTAGATCCTT     4560
TTAAATTAAA AATGAAGTTT TAAATCAATC TAAAGTATAT ATGAGTAAAC TTGGTCTGAC     4620
AGTTACCAAT GCTTAATCAG TGAGGCACCT ATCTCAGCGA TCTGTCTATT TCGTTCATCC     4680
ATAGTTGCCT GACTCCCCGT CGTGTAGATA ACTACGATAC GGGAGGGCTT ACCATCTGGC     4740
CCCAGTGCTG CAATGATACC GCGAGACCCA CGCTCACCGG CTCCAGATTT ATCAGCAATA     4800
AACCAGCCAG CCGGAAGGGC CGAGCGCAGA AGTGGTCCTG CAACTTTATC CGCCTCCATC     4860
CAGTCTATTA ATTGTTGCCG GGAAGCTAGA GTAAGTAGTT CGCCAGTTAA TAGTTTGCGC     4920
AACGTTGTTG CCATTGCTAC AGGCATCGTG GTGTCACGCT CGTCGTTTGG TATGGCTTCA     4980
TTCAGCTCCG GTTCCCAACG ATCAAGGCGA GTTACATGAT CCCCCATGTT GTGCAAAAAA     5040
GCGGTTAGCT CCTTCGGTCC TCCGATCGTT GTCAGAAGTA AGTTGGCCGC AGTGTTATCA     5100
CTCATGGTTA TGGCAGCACT GCATAATTCT CTTACTGTCA TGCCATCCGT AAGATGCTTT     5160
TCTGTGACTG GTGAGTACTC AACCAAGTCA TTCTGAGAAT AGTGTATGCG GCGACCGAGT     5220
TGCTCTTGCC CGGCGTCAAT ACGGGATAAT ACCGCGCCAC ATAGCAGAAC TTTAAAAGTG     5280
CTCATCATTG GAAAACGTTC TTCGGGGCGA AAACTCTCAA GGATCTTACC GCTGTTGAGA     5340
TCCAGTTCGA TGTAACCCAC TCGTGCACCC AACTGATCTT CAGCATCTTT TACTTTCACC     5400
AGCGTTTCTG GGTGAGCAAA AACAGGAAGG CAAAATGCCG CAAAAAAGGG AATAAGGGCG     5460
ACACGGAAAT GTTGAATACT CATACTCTTC CTTTTTCAAT ATTATTGAAG CATTTATCAG     5520
GGTTATTGTC TCATGAGCGG ATACATATTT GAATGTATTT AGAAAAATAA ACAAATAGGG     5580
GTTCCGCGCA CATTTCCCCG AAAAGTGCCA CCTGACGTCT AAGAAACCAT TATTATCATG     5640
ACATTAACCT ATAAAAATAG GCGTATCACG AGGCCCTTTC GTCTCGCGCG TTTCGGTGAT     5700
GACGGTGAAA ACCTCTGACA CATGCAGCTC CCGGAGACGG TCACAGCTTG TCTGTAAGCG     5760
GATGCCGGGA GCAGACAAGC CCGTCAGGGC GCGTCAGCGG GTGTTGGCGG GTGTCGGGGC     5820
TGGCTTAACT ATGCGGCATC AGAGCAGATT GTACTGAGAG TGCAC                    5865
```

Figure 13. hCMV10A1 Sequence

```
AGATCTCCCG ATCCCCTATG GTCGACTCTC AGTACAATCT GCTCTGATGC CGCATAGTTA    60
AGCCAGTATC TGCTCCCTGC TTGTGTGTTG GAGGTCGCTG AGTAGTGCGC GAGCAAAATT   120
TAAGCTACAA CAAGGCAAGG CTTGACCGAC AATTGCATGA AGAATCTGCT TAGGGTTAGG   180
CGTTTTGCGC TGCTTCGCGA TGTACGGGCC AGATATACGC GTTGACATTG ATTATTGACT   240
AGTTATTAAT AGTAATCAAT TACGGGGTCA TTAGTTCATA GCCCATATAT GGAGTTCCGC   300
GTTACATAAC TTACGGTAAA TGGCCCGCCT GGCTGACCGC CCAACGACCC CCGCCCATTG   360
ACGTCAATAA TGACGTATGT TCCCATAGTA ACGCCAATAG GGACTTTCCA TTGACGTCAA   420
TGGGTGGACT ATTTACGGTA AACTGCCCAC TTGGCAGTAC ATCAAGTGTA TCATATGCCA   480
AGTACGCCCC CTATTGACGT CAATGACGGT AAATGGCCCG CCTGGCATTA TGCCCAGTAC   540
ATGACCTTAT GGGACTTTCC TACTTGGCAG TACATCTACG TATTAGTCAT CGCTATTACC   600
ATGGTGATGC GGTTTTGGCA GTACATCAAT GGGCGTGGAT AGCGGTTTGA CTCACGGGGA   660
TTTCCAAGTC TCCACCCCAT TGACGTCAAT GGGAGTTTGT TTTGGCACCA AAATCAACGG   720
GACTTTCCAA AATGTCGTAA CAACTCCGCC CCATTGACGC AAATGGGCGG TAGGCGTGTA   780
CGGTGGGAGG TCTATATAAG CAGAGCTCTC TGGCTAACTA GAGAACCCAC TGCTTAACTG   840
GCTTATCGAA ATGTCGACTG AGAACTTCAG GGTGAGTTTG GGACCCTTG ATTGTTCTTT    900
CTTTTTCGCT ATTGTAAAAT TCATGTTATA TGGAGGGGC AAAGTTTTCA GGGTGTTGTT    960
TAGAATGGGA AGATGTCCCT TGTATCACCA TGGACCCTCA TGATAATTTT GTTTCTTTCA  1020
CTTTCTACTC TGTTGACAAC CATTGTCTCC TCTTATTTTC TTTTCATTTT CTGTAACTTT  1080
TTCGTTAAAC TTTAGCTTGC ATTTGTAACG AATTTTTAAA TTCACTTTTG TTTATTTGTC  1140
AGATTGTAAG TACTTTCTCT AATCACTTTT TTTTCAAGGC AATCAGGGTA TATTATATTG  1200
TACTTCAGCA CAGTTTTAGA GAACAATTGT TATAATTAAA TGATAAGGTA GAATATTTCT  1260
GCATATAAAT TCTGGCTGGC GTGGAAATAT TCTTATTGGT AGAAACAACT ACATCCTGGT  1320
CATCATCCTG CCTTTCTCTT TATGGTTACA ATGATATACA CTGTTTGAGA TGAGGATAAA  1380
ATACTCTGAG TCCAAACCGG GCCCCTCTGC TAACCATGTT CATGCCTTCT TCTTTTTCCT  1440
ACAGCTCCTG GGCAACGTGC TGGTTGTTGT GCTGTCTCAT CATTTTGGCA AGGATCGGCC  1500
GGAACAGCAT CAGGACCGAC ATGGAAGGTC CAGCGTTCTC AAAACCCCTT AAAGATAAGA  1560
TTAACCCGTG GAAGTCCTTA ATGGTCATGG GGGTCTATTT AAGAGTAGGG ATGGCAGAGA  1620
GCCCCCATCA GGTCTTTAAT GTAACCTGGA GAGTCACCAA CCTGATGACT GGGCGTACCG  1680
CCAATGCCAC CTCCCTTTTA GGAACTGTAC AAGATGCCTT CCCAAGATTA TATTTTGATC  1740
TATGTGATCT GGTCGGAGAA GAGTGGGACC CTTCAGACCA GGAACCATAT GTCGGGTATG  1800
GCTGCAAATA CCCCGGAGGG AGAAAGCGGA CCCGGACTTT TGACTTTTAC GTGTGCCCTG  1860
GGCATACCGT AAAATCGGGG TGTGGGGGC CAAGAGAGGG CTACTGTGGT GAATGGGGTT   1920
GTGAAACCAC CGGACAGGCT TACTGGAAGC CCACATCATC ATGGGACCTA ATCTCCCTTA  1980
AGCGCGGTAA CACCCCCTGG GACACGGGAT GCTCCAAAAT GGCTTGTGGC CCCTGCTACG  2040
ACCTCTCCAA AGTATCCAAT TCCTTCCAAG GGGCTACTCG AGGGGGCAGA TGCAACCCTC  2100
TAGTCCTAGA ATTCACTGAT GCAGGAAAAA AGGCTAATTG GACGGGCC AAATCGTGGG    2160
GACTGAGACT GTACCGGACA GGAACAGATC CTATTACCAT GTTCTCCCTG ACCCGCCAGG  2220
TCCTCAATAT AGGGCCCGC ATCCCCATTG GGCCTAATCC CGTGATCACT GGTCAACTAC   2280
CCCCCTCCCG ACCCGTGCAG ATCAGGCTCC CCAGGCCTCC TCAGCCTCCT CCTACAGGCG  2340
CAGCCTCTAT AGTCCCCAC ACTGCCCCAC CTTCTCAACA ACCTGGGACG GGAGACAGGC   2400
TGCTAAACCT GGTAGAAGGA GCCTATCAGG CGCTTAACCT CACCAATCCC GACAAGACCC  2460
AAGAATGTTG GCTGTGCTTA GTGTCGGGAC CTCCTTATTA CGAAGGAGTA GCGGTCGTGG  2520
GCACTTATAC CAATCATTCT ACCGCCCCGG CCAGCTGTAC GGCCACTTCC CAACATAAGC  2580
TTACCCTATC TGAAGTGACA GGACAGGGCC TATGCATGGG AGCACTACCT AAAACTCACC  2640
AGGCCTTATG TAACACCACC CAAAGTGCCG GCTCAGGATC CTACTACCTT GCAGCACCCG  2700
CTGGAACAAT GTGGGCTTGT AGCACTGGAT TGACTCCCTG CTTGTCCACC ACGATGCTCA  2760
ATCTAACCAC AGACTATTGT GTATTAGTTG AGCTCTGGCC CAGAATAATT TACCACTCCC  2820
CCGATTATAT GTATGGTCAG CTTGAACAGC GTACCAAATA TAAGAGGGAG CCAGTATCGT  2880
TGACCCTGGC CCTTCTGCTA GGAGGATTAA CCATGGGAGG GATTGCAGCT GGAATAGGGA  2940
CGGGGACCAC TGCCCTAATC AAAACCCAGC AGTTTGAGCA GCTTCACGCC GCTATCCAGA  3000
CAGACCTCAA CGAAGTCGAA AAATCAATTA CCAACCTAGA AAAGTCACTG ACCTCGTTGT  3060
CTGAAGTAGT CCTACAGAAC CGAAGGGCC TAGATTTGCT CTTCCTAAAA GAGGGAGGTC   3120
TCTGCGCAGC CCTAAAAGAA GAATGTTGTT TTTATGCAGA CCACACGGGA CTAGTGAGAG  3180
ACAGCATGGC CAAACTAAGG GAAAGGCTTA ATCAGAGACA AAAACTATTT GAGTCAGGCC  3240
AAGGTTGGTT CGAAGGGCAG TTTAATAGAT CCCCTGGTT TACCACCTTA ATCTCCACCA   3300
TCATGGGACC TCTAATAGTA CTCTTACTGA TCTTACTCTT TGGACCCTGC ATTCTCAATC  3360
GATTAGTTCA ATTTGTTAAA GACAGGATCT CAGTAGTCCA GGCTTTAGTC CTGACTCAAC  3420
AATACCACCA GCTAAAGCCT ATAGAGTACG AGCCATAGGG CGCCTAGTGT TGACAATTAA  3480
TCATCGGCAT AGTATACGGC ATAGTATAAT ACGACTCACT ATAGGAGGGC CACCATGGCC  3540
AAGTTGACCA GTGCCGTTCC GGTGCTCACC GCGCGCGACG TCGCCGGAGC GGTCGAGTTC  3600
TGGACCGACC GGCTCGGGTT CTCCCGGGAC TTCGTGGAGG ACGACTTCGC CGGTGTGGTC  3660
CGGGACGACG TGACCTGTT CATCAGCGCG GTCCAGGACC AGGTGGTGCC GGACAACACC   3720
CTGGCCTGGG TGTGGGTGCG CGGCCTGGAC GAGCTGTACG CCGAGTGGTC GGAGGTCGTG  3780
TCCACGAACT TCCGGGACGC CTCCGGGCCG GCCATGACCG AGATCGGCGA GCAGCCGTGG  3840
GGGCGGGAGT TCGCCCTGCG CGACCCGGCC GGCAACTGCG TGCACTTCGT GGCCGAGGAG  3900
CAGGACTGAN NNNCGGACCG GTCGA                                        3925
```

EXPRESSION SYSTEMS

The present invention relates to new expressions systems, and in particular to expression systems in which a gene of interest is expressed at an optimal level. Particular examples of such expression systems are retroviral packaging cell lines and a number of preferred cell lines have been identified.

The ability of eukaryotic and prokaryotic ribosomes to reinitiate translation at an internal start codon within an mRNA sequence has previously been recognised. Studies have been reported in which the efficiency of the process, which is generally regarded as being low, has been connected with the length of the intercistronic sequence (Kozak (1987) Mol. Cell Biol. 7, 3438–3445). Selection of this sequence or spacer as 70 bp in length, and containing no other start codons, has been previously reported as being optimal for reinitiation in a eukaryotic cell line (Cosset F-L., Virology (1991) 185, 862).

The applicants have found a way in which the inefficiency associated with the translation reinitiation process can be used to good effect.

According to the present invention there is provided a recombinant expression vector comprising a gene of interest and a selectable marker gene, wherein the selectable marker gene is arranged downstream of the gene of interest and a stop codon associated with the gene of interest is spaced from a start codon of said selectable marker gene at a distance which is sufficient to ensure that translation re-initiation is required before said selectable marker protein is expressed from the corresponding mRNA.

The invention further provides a process for producing cell lines in which a gene of interest is expressed, which process comprises transforming host cells with an expression vector comprising said gene of interest and a selectable marker gene, wherein the selectable marker gene is arranged downstream of the gene of interest and a stop codon associated with the gene of interest is spaced from a start codon of said selectable marker gene at a distance which is sufficient to ensure that translation re-initiation is required before said selectable marker protein is expressed from the corresponding mRNA, and selecting those cells where expression of the selectable marker gene may be detected.

Since re-initiation of translation is a relatively inefficient process, this means that the selectable marker protein will be expressed at lower levels than the product of the gene of interest. When the marker protein is expressed at detectable levels, the gene of interest will be expressed at higher levels. This will ensure that during the subsequent selection procedure, only those cell clones which express the gene of interest at higher or optimal levels will survive. Low expressing clones will be eliminated by the selection process.

Cells transformed with the above-described expression vectors form a further aspect of the invention.

The host cells are suitably eukaryotic or prokaryotic host cells, preferably eukaryotic host cells.

The number of nucleotides in the space between the stop codon of the gene of interest and the start codon of the selectable marker will suitably be in the range of from 20–200 nucleotides, preferably from 60–80 nucleotides, even more preferably 70–80 nucleotides.

The vectors used in the process of the invention may be any of the known types, for example expression plasmids or viral vectors.

Selected cells may be cultured and if required, the protein product of the gene of interest isolated from the culture using conventional techniques. Alternatively, expression of the gene of interest may result in other desired effects, for example, where the gene of interest is included as part of a viral packaging construct.

Some experimental and clinical gene transfer protocols require the design of gene transfer vectors suitable for in vivo gene delivery (Miller, A.D. 1992. Nature 357: 455–460). Retroviral vectors are attractive candidates for such applications, because they can provide stable gene transfer and expression (Samarut J. et al., Meth. Enzymol. in press) and because packaging cells have been designed which produce non-replication competent viruses (Miller A. D (1990) Hum Gene Ther. 1 5–14). However currently available recombinant retroviruses suffer from a number of drawbacks.

Packaging cell lines provide in trans the retroviral proteins encoded by the qag, pol, and env genes required to obtain infectious retroviral particles. The qag and pol products are respectively the structural components of the virion cores and the replication machinery (enzymes) of the retroviral particles whereas the env products are envelope proteins responsible for the host-range of the virions and for the initiation of infection and for sensitivity to humoral factors. An ideal packaging cell line should produce retroviruses that only contain the retroviral vector genome, and absolutely no replication-competent genomes or defective genomes encoding some of the viral structural genes.

A number of packaging cell lines designed for human gene transfer have been designed in the past by introducing plasmid DNAs which contain "helper genomes" encoding gag, pol and/or env genes into cells.

Recroviral packaging cell lines are cells that have been engineered to provide in trans all the functions required to express infectious retroviral vectors. A helper genome (or construct or unit), is herein also referred to as "retroviral packaging construct (or unit)" or "packaging-deficient construct (or genome unit)" or "gag-pol/env expression plasmids".

Much efforts has been made to design strategies to optimize the helper-genomes in order (i) to get the highest production of retroviral packaging functions (which correlates which infection titers of retroviral particles) and (ii) to minimise the chance that the helper genome can be transmitted via the viral particles (which may lead to emergence of unwanted retroviral forms).

The first of these packaging cell lines used full length retroviral genomes as helper genomes that had been crippled for important cis-regulated replicative functions (reviewed in Miller, Hum. Gene. Ther. 1: 5–14 1990). In order to reduce the possibility of occurrence of replication-competent viruses and of transfer of virus structural genes, a second generation of safer packaging cell lines has been designed by using two separate and complementary helper genomes which express either gag-pol or env and are packaging-deficient (Miller supra).

The cells into which these helper genomes were introduced were isolated by cotransfecting them with plasmids encoding selectable markers. However, as no selection was applied on the packaging-deficient retroviral genome itself, the helper functions can be lost during the passages of the cells in culture and the current packaging systems provide limited titers of infectious retroviral vectors, usually only of the order of $10^5$–$10^6$ infectious units i.u/ml. Indeed the cotransfection with a plasmid encoding a selectable marker does not directly select the best gag-pol-env-expressing cells.

The invention further provides a retroviral packaging cell line comprising a host cell transformed with (i) a packaging deficient construct which expresses a viral gag-pol gene and a first selectable marker gene, and/or (ii) a packaging-deficient construct which expresses a viral env gene and a second selectable marker gene; wherein a start codon of the first and second selectable markers are spaced from the stop codons of the viral gag-pol gene and the viral env gene respectively by a distance which ensures that reinitiation of mRNA translation is required for expression of marker protein product of said first and/or second selectable marker gene.

The retroviral packaging cell line may be obtained by the above described process which will involve selecting transfected cells which express said first and/or second marker genes.

By using helper constructs which are directly selectable and which provide for high expression of the viral gene, high titre retroviral vectors may be obtained.

Helper constructs for use in the process form a furtner aspect of the invention.

The retroviral vectors prepared from the conventional packaging cell lines are usually not contaminated by replication-competent retroviruses (RCRs). However, recombinant amphotropic murine retroviruses have been shown to arise spontaneously from certain packaging cell lines. The generation of such RCRs involves recombination at least between gag-pol/env packaging sequence and vector sequences (Cosset et al., Virology, (1993) 193: 385–395).

Recombinant RCRs have been associated with the development of lymphomas in some severely immunosuppressed monkeys (Donahue et al., J. Exp Med (1992) 176: 1125–1135). In addition, retroviral vector preparations may also contain, at low frequencies, retroviruses coding for functional envelope glycoproteins (Kozak and Kabat, 1990, J. Virol. 64: 3500–3508) or for gag-pol proteins. Although the pathogenicity of these gag-pol or env recombinant retroviruses is probably low, more evolved recombinant retroviruses with higher pathogenic potential may occur when injected in vivo, by recombination and/or complementation of the initial recombinant viruses with some endogenous retroviruses.

In a preferred embodiment of the retroviral packaging cell lines of the invention, the overlapping sequences between the genomes of the retroviral vector and the helper construct are reduced, for-example as compared to constructs such as CRIPenv and CRIPAMgag (Danos et al., Proc. Natl. Acad. Sci USA 85: 6460–6464). In particular, the viral sequences in the helper construct are reduced, for example, not only the packaging sequence but also the 3' Long Terminal Repeat (LTR), the 3' non-coding sequence and/or the 5' LTR may be eliminated.

The possibility of generation of such RCRs and recombinant retroviruses can be reduced by reducing the overlapping sequences between the genomes of both the retroviral vector and the helper construct.

Conventional retroviral vectors are strongly inactivated by human serum which makes them of limited or no use for in situ gene transfer in gene therapy applications. It has previously been shown that inactivation by complement in human serum is controlled by the cell line used to produce the virions and by viral envelope determinants (Takeuchi et al., J. Virol (1994) 68: 8001–8007). In particular, inactivation is caused by some properties of the cell lines that have been used to construct the packaging cells (NIH-3T3) and also by viral determinants located in the retroviral envelope as shown (Takeuchi et al., J. Virol (1994) 68: 8001–8007). In vivo gene delivery is an important goal for a number of human gene therapy strategies.

The applicants have found that certain cell lines form preferred packaging cell lines.

Particularly preferred packaging cell lines are the HT1080 line, the TE671 line, the 3T3 line, the 293 line and the Mv-1-Lu line. One example of retroviral packaging cells that will produce complement-resistant virus comprise human HT1080 cells and express RD114 envelope. Such cells form a preferred aspect of the invention.

Packaging cell lines according to the invention provide 50–100 fold increased titers of retroviral vectors as compared to conventional packaging cell lines. Retroviral vectors provided by these new cells are safe, in terms of generation of RCRs, and considerably more resistant to inactivation by human complement.

Packaging cell lines according to the invention may be able to transduce helper-free, human complement-resistant retroviral vectors at titers consistently higher than $10^7$ i.u./ml.

Suitable semi-packaging cell lines in accordance with the invention are those which express only the gag-pol genes. Such cell lines may suitably be derived from TE671, MINK Mv-1-Lu, HT1080, 293 or NIH-3T3 cells by introduction of plasmid CeB (the MoMLV gag-pol expression unit).

Particularly preferred expression vectors in accordance with the invention for use in retroviral packaging cell lines are those which include MLV gag and pol genes such as CeB. Other plasmids may include gag and pol genes from other retroviruses or chimeric or mutated gag and pol genes.

Various viral and retroviral envelope genes may be included in the plasmids such as MLV-A envelope, GALV envelope, VSV-G protein, BaEV envelope, RD114 envelope and chimeric or mutated envelopes. Plasmids which include the RD114 env gene such as FBdelPRDSAF as illustrated hereinafter, provide one example of suitable constructs.

The novel retroviral packaging cells described hereinafter, have been designated FLY cells, and may be designed for in vivo gene delivery.

Considerable variations were found between the various cell lines screened for their ability to release type C mammalian retroviruses. In addition, few cell lines were able to produce retroviruses completely resistant to human complement. Based on these two criteria, human fibrosarcoma HT1080 and rhabdomyosarcoma TE671 cells were selected for optimum construction of packaging cells. Other studies have shown the importance of endogenous retrovirus expression in the generation of recombinant retroviruses from retroviral packaging lines (Ronfort et al., Virology, (1995), 207, 271–275, Vanin, E. F. et al., J Virol (1994) 68: 4241–4250.). The co-packaging of an endogenous genome and a vector can lead to emergence of recombinant retroviruses (Vanin et al., supra). Recombination involves template switching during reverse transcription of such hybrid retroviruses (Hu et al., Science, (1990) 250: 1227) and homologies between the two genomes considerably enhance the frequency of reverse transcriptase jumps (Zhang et al., J. Virol. (1994) 68: 2409–2414). Therefore an ideal packaging cell line should not express endogenous MLV-like (or type C retrovirus-like) retroviral genomes which can be packaged by type C gag proteins (Scadden et al., J. Virol. (1990) 64: 424–427, Torrent et al., J. Mol. Biol. (1994) 240 434–444).

Packaging of human endogenous retroviral RNA was not detected in TELCeB and FLY packaging cells when virion associated RNA was analysed by RT-PCR using generic primers. HT1080- and TE671 derived packaging cell lines may be safer in this respect than those generated from NIH3T3 cells, such as GP+EAM12 cells, which are known to express and package sequences related to type C retroviruses (Scadden et al. supra).

To generate the FLY packaging cell lines, HT1080 cells were transfected with gag-pol and env expression plasmids designed to optimise viral protein expression. Direct selection for viral gene expression was achieved in accordance with the invention by expression of a selectable marker gene by re-initiation of translation of the mRNA expressing the viral proteins. This strategy resulted in packaging cell lines capable of producing extremely high titer viruses. Furthermore, long-term expression of packaging functions can be maintained in these cells. Many unnecessary viral sequences were eliminated from the packaging constructs to reduce the risk of helper virus generation; indeed the final packaging cells did not produce helper virus, in that no replication competent virus (RCR) could be detected per $10^7$ vector particles.

The FLY packaging cells described herein are safer than, for example, psiCRIP cells, at least for generation of env recombinant retroviruses as is illustrated in Table 4 hereinafter, probably because less retroviral sequences overlapping with the vector were present in the present env-expression plasmid. Few reports have addressed the question of the characterization of recombinant retroviruses (RVs) (Cosset, F. L., et al., Virology (1993) 193: 385–395). It is possible that such RVs could not be detected in previous packaging cell lines due to lower overall titers. RVs are defective in normal cell culture conditions but are likely to evolve to replication competent viruses if they are allowed to replicate in cells complementing their expression like co-cultivated packaging cells (Bestwick et al., Proc. Natl Acad Sci USA, (1988) 85: 5404–5408, Cosset et al., (1993) supra)

In preferred retroviral packaging systems according to the invention, RVs are eradicated for example by removal of viral LTRs from the packaging construct.

Consistent with our previous studies (Takeuchi, Y., et al., J Virol (1994) 68: 8001–8007), LacZ(RD114) and lacZ (MLV-A) pseudotypes produced from HT1080 and TE671cells were more resistant to human complement than LacZ(RD114) or LacZ(MLV-A) pseudotypes produced by 3T3 of dog cells. It was therefore decided to use RD114 and MLV-A env genes to generate recombinant virions with MoMLV cores.

The sequence of RD114 env gene was determined and is shown in FIG. 4 (SEQ ID NO: 1). It was found to be very close to BaEV (baboon endogenous virus) a type C retrovirus (Benveniste, R. E. et al., Proc. Natl. Acad. Sci. USA (1973) 70: 3316–3320; Kato, S. et al., Japan. J. Genet. (1987) 62: 127–137) with an envelope gene displaying similarities to the external part of type D simian retroviruses (SRVs). RD114 uses the SRV receptor on human cells (Sommerfelt & Weiss, Virology (1990) 176: 58–69; Sommerfelt, M. A. et al., J Virol (1990) 64: 6214–6220) making the FLY packaging cells with RD114 envelope capable of generating virions with different tropism. Retroviral vectors prepared so far for human gene therapy have used either MLV-A or GALV (gibbon ape leukemia virus) envelopes which display some similarities (Battini, J. L.,et al., J Virol. (1992) 66: 1468–1475) and which use two related cell surface receptors for infection (Miller, D. G. et al., J Virol (1994) 68: 8270–8276). Differences in tissue-specific expression of MLV-A or GALV receptors have been reported (Kavanaugh et al., Proc Natl Acad Sci USA (1994) 91: 7071–7075).

The invention will now be particularly described by way of example with reference to the accompanying drawings in which:

BRIEF DESCRIPTION OF THE DRAWINGS

FIG. 1. illustrates the structure and expression of CeB. The env gene (Xbal-Clal) of plasmid pCRIP was removed and was replaced by coinsertion of the two fragments Xbal-Sfil (restriction sites underlined) from pOXEnv and a Sfil-Clal PCR product containing the bsr selectable marker. This results in positioning the bsr start codon (shadowed) 74 bp downstream to the pol stop codon (bold). The sequence shown in the figure corresponds to SEQ ID NO: 28.

Open triangle are start codons (gag and bsr), black triangles are stop codons (pol and bsr). The shadowed triangle is the start codon of env, in the same reading frame with that of bsr. SD and SA are the splice donnor and splice acceptor sites.

FIG. 2 illustrates the structure and expression of FbdelPASAF.

Immediately after the stop codon of env (bold) was inserted a non retroviral Kasl-Ncol (restriction sites underlined) linker which positions the phleo start codon (shadowed) 76 bp downstream. Open triangle are start codons (env and phleo), black triangles are stop codons (env and phleo). SD and SA are the splice donnor and splice acceptor sites. The sequence shown in the figure corresponds to SEQ ID NO: 29.

FIG. 3 illustrates plasmids for expression of Ampho, Eco, RD114, Xeno, 10A1, GALV, VSV-G and FeLVB envelopes. All genes are expressed in the same backbone as detailed in FIG. 2. The BglII sites for ecotropic (MoMLV strain), 10A1, xenotropic (NZB.1.V6 strain) and amphotropic (4070A strain), the Ndel site of RD114 (SC3C strain, the BamHl site for both FeLVB and GALV were used as 5' ends, and linked to Mscl site immediately after the splice donor site in the leader of FB29 LTR.

FIG. 4 shows the sequence of the RD114 env gene (SEQ ID No 1).

FIG. 5 shows the genetic structure of gag-pol constructs. Initiation (▽) and termination (▼) codons are shown. The thick dotted line below each construct shows MLV-derived sequences. Nucleotide positions of MLV-derived sequences are shown according to: Shinnick et al. (1981) (from nt 1 to nt 6000 with deletion of the packaging signal (DY) from Ball (nt 215) to PstI (nt 568), and with some further MOMLV sequences in both CeB and CeB DS- from nt 7676 to nt 7938. gag-pol and bsr genes were expressed from the same transcription unit using the either a retroviral promoter (Mo LTR) or a non retroviral promoter (hCMV) and non retroviral polyadenylation sequence (polyA). Splice donor (SD) and acceptor (SA) sites are indicated. The thin line denotes retroviral non coding sequences. The thick line shows the rabbit beta-1 globin intron B. The position of some restriction sites is indicated.

FIG. 6. FIG. 6 shows the nucleic acid sequence of a portion of CeB (SEQ ID NO:2).

FIG. 7. FIG. 7 shows the nucleic acid sequence of a portion of hCMV+intron (SEQ ID NO:3).

FIG. 8. FIG. 8 shows the nucleic acid sequence of a portion of hCMV+intronka (SEQ ID NO:4).

FIG. 9. FIG. 9 shows the nucleic acid sequence of a portion of FbdelPASAF (SEQ ID NO:5).

FIG. 10. FIG. 10 shows the nucleic acid sequence of a portion of FbdelPMOSAF (SEQ ID NO:6).

FIG. 11. FIG. 11 shows the nucleic acid sequence of a portion of FbdelPGASAF (SEQ ID NO:7).

FIG. 12. FIG. 12 shows the nucleic acid sequence of a portion of FbdelPRDSAF (SEQ ID NO:8).

FIG. 13. FIG. 13 shows the nucleic acid sequence of a portion of CMV10A1 (SEQ ID NO:9).

The components of the viral particles are produced by two independent expression plasmids (gag-pol or env) which also contain selectable markers (bsr or Phleo) expressed from the same transcriptional units as gag-pol or env (FIGS. 1 & 2). The selectable markers are located downstream to gag-pol or env genes and there is an optimal distance between the stop codon of the upstream reading frames and the start codon of the selectable genes that should allow re-initiation of translation (Kozak, Mol Cell Biol. (1987) 7,: 3438–3445). Because there is no "Kozak" sequence (Kozak, Cell,(1986) 44: 283–292) required for a normal initiation of translation for the marker gene, they can only be expressed by re-initiation of translation after the upstream viral gene has been successfully expressed. Consequently and also because re-initiation of translation is a poorly efficient process, after transfection of these plasmids, cells resistant to the drugs corresponding to those selectable genes express high levels of the viral proteins.

To avoid viral transmission of these "helper" genomes the constructs used suitably have the classical deletions of both the packaging sequence located in the leader region and of the 3' LTR, the latter being replaced by SV40 polyadenylation sequences (FIGS. 1 & 2).

Plasmid CeB is the MoMLV gag-pol-expression unit. It derives from pCRIP, a plasmid used to generate the constructs introduced in the CRIP and CRE packaging cell lines (Danos and Mulligan, 1988). As shown in FIG. 1 for generation of plasmid CeB the env gene of pCRIP has been deleted mostly and the bsr selectable marker, -encoding a protein conferring resistance to blasticidin (Izumi et al., Experimental Cell Research (1991) 197, 229–233)– has been inserted downstream to pol gene. There are exactly 74 bp with no ATG triplets between the stop codon of pol and the start codon of bsr, this allows its expression by re-initiation of translation on the gag-pol mRNA, after translation of the gag-pol reading frame.

FbdelPASAF is a plasmid expressing the amphotropic env gene and the phleo selectable marker conferring resistance to phleomycin (Gatignol et al., FEBS Letters (1988) 230: 171–175). By using a PCR-mediated mutagenesis strategy which modifies the end of env gene (see FIG. 2), a 76 bp linker was inserted between the stop codon of env and the start codon of phleo. This allows expression of phleo from the env mRNA by re-initiation of translation. In addition compared to known env-expressing constructs, this strategy of construction has reduced the length of sequences overlapping with the ends of conventional retroviral vectors. The env genes of Mo-MLV, FeLVB, NZB.1V6, 10A1, GALV and RD114 are expressed by plasmids FBdelPMoSAF, FBdelPBSAF, FBdelXSAF, FBdelpGSAF, FBdelp10A1SALF and FBdelPRDSAF, respectively, by using the same backbone as FBdelPASAF (FIG. 3). Retroviral vectors produced with the RD114 envelope will be useful for in vivo gene delivery as comparatively to MLV ecotropic or amphotropic envelopes, virions pseudotyped with RD114 envelopes are not inactivated by human complement when they are produced by Mink Mv-1-Lu cells or by some human cells (Table 1).

The HT1080 cell line, isolated from a human fibrosarcoma (ATCC CCL121). The TE671 cell line isolated from a human rhabdomyosarcoma (ATCC CRL 8805)(purchased from ATCC, and tested for absence of usual cell culture contaminants by ECACC), has been used for the definitive construction of packaging cell lines. HT1080 line was chosen among a panel of primate and human lines because MLV-A and RD114 efficiently rescued retroviral vectors from these cells and also because RD114 pseudotypes produced by this cell line were stable when incubated in human serum. In a standard assay (Takeuchi et al., J Virol (1994), 68, 8001–8007), these latter viruses were found more than 500 fold more stable than similar pseudotypes produced in 3T3 cells.

Another advantage for the use of non murine cells to derive packaging lines is the absence of MLV-related endogenous retroviral-like sequences (like VL30 in 3T3 cells) that can cross-package with MLV-derived retroviral vectors (Torrent et al., 1994) and generate potentially harmful recombinant retroviruses.

The helper constructs were introduced into other cell lines (HT1080 (table 2) Mink Mv-1-Lu (table 2)), 3T3 (not shown), TE671 (table 2)) for the purpose of comparisons of the efficiency of the constructs.

As illustrated hereinafter (Table 2), the reverse transcriptase (RT) activity (provided by expression of the pol gene) in cells transfected with CeB is significantly higher than that of the same cells transfected by the parental plasmid pCRIP or that of cells chronically infected by MLV. This enhancement of viral gene expression is correlated with the titers of lacZ retroviral vectors when an envelope is provided in CeB-lacZ cells after comparison with titers of lacZ pseudotypes of either replication-competent viruses or other helper-free packaging systems.

For the generation of final packaging cell lines, the best clonal env transfectants have been selected. Packaging systems obtained in this way will be able to produce helper-free retroviral vectors at titers greater than $10^8$ infectious particles per ml, which would be 10–100 fold higher to helper-free preparations of others.

Because of the way the selectable markers are expressed (see above), growing the packaging cells in phleamycin and blasticidin selective pressure increase and stabilize the expression of the retroviral components and particularly the envelopes, as it is possible that env glycoproteins have toxic effects for the producer cells in the long term which may lead to a decrease of expression.

Such an enhancement of viral production observed with the packaging systems described herein might increase the emergence of unwanted retroviruses having recombined between the genomes of both the retroviral vector and either of the two packaging-deficient constructs. However, the constructs have been designed in such a way that it reduces the probability of emergence of recombinant viruses compared to the parental constructs. To check their safety, attempts have been made to detect the presence of replication-competent retroviruses by a mobilisation assay of a lacZ provirus. No RC viruses have been found in all retroviral vector preparations tested so far.

The following Examples illustrate the invention.

EXAMPLE 1

Preparation of Cell lines and viruses

The following cell lines were used: A204 (ATCC HTB 82), HeLa (ATCC CCL2), HT1080 (ATCC CCL121), MRC5 (ATCC CCL171), T24 (ATCC HTB 4), VERO (ATCC CCL81) and D17 (ATCC CCL183) were purchased from ATCC.

HOS, TE671 and Mv-1-Lu cells and their clones harboring MFGnlslacZ retroviral vector as described by Takeuchi et al., J Virol (1994), 68, 8001–8007.

The above cell lines were grown in DMEM (Gibco-BRL, U.K.) supplemented with 10% fetal calf serum.

EB8 (Battini et al., J. Virol (1992) 66: 1468–1475); psiCRE, psiCRELLZ and psiCRIP (Danos et al., Proc. Natl. Acad. Sci USA (1988) 85: 6460–6464); Cells GP+EAM12 (Markowitz et al., Virology (1988), 167, 400–406); and NIH-3T3 murine fibroblasts.

These cell lines were grown in DMEM (GIBCO-BRL, U.K.) supplemented with 10% new-born calf serum. Mv-1-Lu, TE671 and HT1080 cells were transfected using calcium-phosphate precipitation method (Sambrook et., "Molecular Cloning" 1989, Cold Spring Harbour Laboratory Press: N.Y.) as described elsewhere (Battini et al., supra). CeB-transfected Mv-1-Lu, TE671 and HT1080 cells were selected with 3, 6–8 and 4 μg/ml of blasticidin S (ICN, UK), respectively, and blasticidin-resistant colonies were isolated 2–3 weeks later. Cells transfected with the various env-expression plasmids were selected with phleomycin (CAYLA, France): 50 μg/ml (for FBASALF-transfected cells) or 10 μg/ml (for FBASAF-, FbdelPASAF-, FbdelPMOSAF, FBdelPIOAISAF or FBdelPRDSAF-transfected cells). Phleomycin-resistant colonies were isolated 2–3 weeks later.

Production of lacZ pseudotypes using replication competent viruses, amphotropic murine leukemia virus (MLV-A) 1504 strain and cat endogenous virus RD114, was carried out as described previously (Takeuchi et al., J Virol (1994), 68, 8001–8007).

EXAMPLE 2
Preparation of Plasmids

The env gene of pCRIP (Danos et al., supra) was excised by HpaI/ClaI digestion. A 500 bp PCR-generated DNA fragment was obtained using pSV2-bsr (Izumi et al., Experimental Cell Research (1991), 197, 299–233) as template and a pair of oligonucleotides:

(5'>CGGAATTCGGATCCGAGCTCGGCCCAGCCGG-CCACCATGAAAACATTTAACATTTC TC) (SEQ ID NO: 10) at 5' end and (5'>GATCCATCGATAAGCTTGGTGGTAAAACTTTT) (SEQ ID No 11) at 3' end, with SfiI and ClaI sites, respectively. This fragment was inserted in HpaI/ClaI sites of pCRIP by co-ligation with a 85 bp HpaI/SfiI DNA fragment isolated from pOXEnv (Russell et al., Nucleic Acids Research (1993), 21, 1081–1085) which provides the end of the Moloney murine leukemia virus (MOMLV) pol gene. The resulting plasmid named CeB (FIG. 1) could express the MOMLV gag-pol gene as well as the bsr selectable marker conferring resistance to blasticidin S, both driven by the MoMLV 5' LTR promoter.

A series of env-expression plasmids was generated using the 4070A MLV (amphotropic) env gene (Ott et al., J Virol (1990), 64, 757–766) and the FB29 Friend MLV promoter (Perryman et al., Nucleic Acid Res (1991), 19, 6950). In FBASALF (FIG. 1) a BglII/ClaI fragment containing the env gene was cloned in BamHI/ClaI sites of plasmid FB3LPh which also contained the C57 Friend MLV LTR driving the expression of the phleo selection marker. A 136 bp env fragment was generated by PCR using plasmid FB3 (Heard et al., J Virol (1991), 65, 4026–4032) as template and a pair of oligonucleotides: (5'>GCTCTTCGGACCCTGCATTC) (SEQ ID NO 12) at 5' end (before ClaI site) and (5'>TAGCATGGCGCC-CTATGGCTCGTACTCTATAGGC)(SEQ ID NO 13) at 3' end, providing a KasI restriction site immediately after the env stop codon. This PCR fragment was digested using ClaI and KasI. A DNA fragment containing the FB29 LTR and the MLV-A env gene was obtained by NdeI/ClaI digestion of FBASALF. The fragments were co-ligated in NdeI/KasI digested pUT626 (kindly provided by Daniel Drocourt, CAYLA labs, France). In the resulting plasmid, named FBASAF (FIG. 1), the phleo selectable marker was expressed from the same mRNA as the env gene. A BglII restriction site was created after the MscI site at position 214 in the FB29 leader by using a commercial linker (Biolabs, France). A NdeI/BglII fragment containing the FB29 LTR was co-inserted with the BglII/ClaI env fragment in NdeI/ClaI-digested FBASAF plasmid DNA, resulting in plasmid FBdelPASAF (FIG. 1). Compared to FBASAF, FBdelPASAF has a 100 bp larger deletion in the leader region.

EXAMPLE 3
Cloning and Sequencing of the RD114 env gene

The RD114 env gene was first sub-cloned in plasmid Bluescript KS+ (Stratagene) as a 3 Kb HindIII insert isolated from SC3C, an RD114 infectious DNA clone (Reeves et al., J. Virol (1984), 52, 164–171). A 2.7 kb ScaI-Hind III fragment of this subclone containing the RD114 env gene was sequenced (FIG. 4 (SEQ ID NO 1)—EMBL accession number; X87829). The 5' non-coding sequence upstream of an NdeI site was deleted by an EcoRI/NdeI digestion followed by filling-in with Kienow enzyme and self-ligation. From this plasmid, two DNA fragments were obtained: a BamHI/NcoI 2.5 Kb fragment and a 63 bp PCR-generated DNA fragment using (5'>CGCCTCATGGCCTTCATTAA) (SEQ ID NO 14) at 5' end (before NotI site) and (5'>TAGCATGGCGCCTCAATCCTGAGCTTCTTCC) (SEQ ID NO 15) at 3' end, providing a KasI restriction site just after RD114 env gene stop codon. The PCR fragment was digested with NcoI and KasI. Both fragments were co-inserted between BglII and KasI sites of FBdelPASAF and the resulting plasmid was named FBdelPRDSAF (FIG. 1).

Plasmid pCRIPAMgag- (Danos, O. et al., Proc Natl Acad Sci USA (1988) 85: 6460–6464) was used for transfection.

EXAMPLE 4
Infection Assays

Target cells were seeded in 24-multiwell plates ($4\times10^4$ cells per well) and were incubated overnight. Infections were then carried out at 37° C. by plating 1 ml dilutions of viral supernatants in the presence of 4 μg/ml polybrene (Sigma) on target cells. 3h later virus-containing medium was replaced by fresh medium and infected cells were incubated for two days before X-gal staining, performed as previously described (Tailor et al., J Virol (1993), 67, 6737–6741, Takeuchi et al., J Virol (1994), 68, 8001–8007). Viral titers were determined by counting lacZ-positive colonies as previously described (Cosset et al., J. Virol. (1990) 64: 1070–1078). Stability of lacZ pseudotypes in fresh human serum was examined by titrating surviving virus after incubation in 1:1 mixture of virus harvest in serum-free medium and fresh human serum for 1 h at 37° C. as described before (Takeuchi et al. supra).

EXAMPLE 5
Reverse Transcriptase (RT) Assay.

RT assays were performed either as described previously (Takeuchi et al. supra) or using an RT assay kit (Boehringer Mannheim, U.K.) following the manufacturer's instruction but using $MnCl_2$ (2 mM) instead of $MgCl_2$.

EXAMPLE 6
Screening Producer Cell Lines

Viral particles generated with RD114 envelopes have been found to be more stable in human serum than virions with MLV-A envelopes and that the producer cell line also controls sensitivity (Takeuchi et al. supra). A panel of cell lines was screened for their ability to produce high titer viruses and for the sensitivity of these virions to human serum. To do this, cells were infected at high multiplicity with lacZ pseudotypes of either MLV-A or RD114 and cells producing helper-positive lacZ pseudotypes were established. Human HT1080 and TE671 and mink Mv-1-Lu cells were found to release high titer lacZ(RD114) and lacZ (MLV-A) viruses. LacZ(MLV-A) pseudotypes produced by HT1080 cells were more resistant to human serum than those produced by other cells. The titer of these viruses was only four-fold less following a 1 hr incubation with human serum than a control incubation (Table 1). LacZ(RD114) pseudotypes produced by human cells or mink Mv-1-Lu cells were in general stable in human serum (Table 1). These results suggested that HT1080, TE671 and Mv-1-Lu cells provided the best combination of high lacZ titers and resistance to human serum and they were therefore used for the generation of retroviral packaging cells.

TABLE 1

Titer and stability of lacZ pseudotypes.

| Producer cell | LacZ (MLV-A) | | LacZ (RD114) | |
|---|---|---|---|---|
| | Titer[a] | Stability[b] | Titer[a] | Stability[b] |
| A204 | 650 | <3 | 1,200 | 105 |
| HeLa | 9 | nd | 2,000 | 115 |
| HOS | 4,500 | 6 | 23,000 | 86 |
| HT1080 | 2,000,000 | 26 | 400,000 | 129 |
| MRC-5 | 450 | 10 | 1,000 | nd |
| T24 | 350 | nd | 1,200 | nd |
| TE671 | 15,000 | 2 | 90,000 | 38 |
| VERO | 260 | nd | 90 | nd |
| D17 | 900 | <1 | 200,000 | 1 |
| Mv-1-Lu | 80,000 | 1 | 200,000 | 120 |

[a]Titration on TE671 cells as lacZ i.u./ml
[b]% of infectivity of human serum-treated viruses compared to fetal calf serum-treated viruses

EXAMPLE 7
Construction of an Improved gag-pol Expression Vector

A MoMLV gag-pol expression plasmid, CeB (FIG. 1), was derived from pCRIP (Danos et al., Proc. Natl. Acad Aci USA (1988) 85: 6460–6464). Approximately 2 Kb of env sequence were removed from PCRIP and the bsr selectable marker, conferring resistance to blasticidin S (Izumi et al., Experimental Cell Research (1991) 197: 229–233), was inserted 74 nts downstream of the gag-pol gene. This 74 nts interval had no ATG triplets and was thought to provide an optimal distance between the stop codon of the pol reading frame and the start codon of the bsr gene to allow re-initiation of translation (Kozak Mol Cell Biol., 1987, 7: 3438–3445). There was no "Kozak" consensus sequence (Kozak Cell, (1986) 44: 283–292) at the 5' end of the marker gene. Therefore, bsr could only be expressed by re-initiation of translation after the upstream gag-pol gene had been expressed. Consequently, after transfection of CeB in Mv-1-Lu/MFGnlsLacZ (ML), TE671/MFGnlsLacZ (TEL) or HT1080 cells, blasticidin S-resistant bulk populations and most cell clones expressed high levels of gag-pol proteins assessed by the reverse-transcriptase (RT) activity found in cell supernatants (Table 2). Considerably higher RT activities were found in bulk populations of CeB-transfected ML cells compared to bulk population of ML cells stably transfected with the parental pCRIP construct. Similarly the RT activities of two packaging cell lines generated using pCRIPenv- construct, psiCRE cells (Danos et al., supra) and EB8 cells (Battini supra.) were less than that of CeB transfected clones (Table 2). Finally, RT activity in CeB transfected cell supernatants was higher than that of cells chronically infected by replication-competent MLV-A (Table 2).

TABLE 2

Secreted reverse transcriptase expression

| Cell[a] | RT activity[b] | LacZ Titer[c] |
|---|---|---|
| ML/MLV-A | 1 | 8 × 10⁴ |
| MLSvB | 0.1 | <1 |
| MLCRIP (bulk) | 0.15 | nd |
| MLCeB (bulk) | 1.7 | nd |
| MLCeB1 | 4.2 | 1 × 10⁶ |
| MLCeB4 | 1.6 | 1 × 10⁶ |
| TEL/MLV-A | 3.6 | 2 × 10⁶ |
| TELCeB6 | 5.2 | 4 × 10⁷ |
| HT1080/MLV-A | 1.1 | 1 × 10⁶ |
| HTCeB6 | 1.9 | 1 × 10⁶ |
| HTCeB18 | 2.7 | 2 × 10⁶ |
| HTCeB22 (FLY) | 6.9 | 5 × 10⁶ |
| HTCeB48 | 5.5 | 3 × 10⁶ |
| EB8 | 0.22 | 1 × 10⁴ |
| psiCRE-LLZ | 1.2 | 1 × 10⁵ᵈ |

[a]ML, Mv-1-Lu cells harboring a MFGnlslacZ provirus; TEL, TE671 cells harboring a MFGnlslacZ provirus; /MLV-A, cells chronically infected with MLV-A 1504 strain; MLSvB, ML cells transfected with a plasmid pSV2bsr alone; MLCRIP, ML cells co-transfected with pCRIP and pSV2bsr.
[b]Average of arbitrary units relative to ML/MLV-A RT activity of at least two independent experiments was shown. The standard errors did not exceed 20% of the values.
[c]titration on TE671 cells as lacZ i.u./ml. After polyclonal transfection of a plasmid which expresses MLV-A env in MLCeB clones, TELCeB clones, HTCeB clones and EB8 cells; nd, not done.
[d]titration on NIH3T3 cells To rescue infectious lacZ viruses, MLCeB and TELCeB clones were transfected with FBASALF DNA, a plasmid designed to express the MLV-A env gene (FIG. 1). Bulk populations of stable FBASALF transfectants were isolated and supernatants were titrated using TE671 cells as targets. Titers of lacZ viruses were higher than either MLV-A infected ML or TEL cells, or FBASALF-transfected EB8 cells (Table 2). These data suggested that CeB was an extremely efficient MLV gag-pol expression vector in mink Mv-1-Lu and TE671 cells. CeB was therefore used to derive packaging cells by transfection of HT1080 cells. 41/49 blasticidin S-resistant colonies had detectable levels of RT; 9 had RT activity higher than that of control MLV-A-infected HT1080 cells (data not shown). Expression of gag precursor was confirmed in cell lysates and supernatants of these 9 HTCeB clones by immunoblotting using antibodies against p30-CA (data not shown). The 4 clones with the highest expression of gag proteins (clones 6,18,22 and 48) were infected at high-multiplicity with helper free, lacZ pseudotypes bearing MLV-A envelopes (MFGnlslacZ(A)) produced by TELCeB6/FBASALF (Table 3) and then transfected with FBASALF. Supernatants of bulk, phleomycin-resistant transfectants were assessed for RT activity and lacZ titer (Table 2). Clone HTCeB22, named FLY, was found to be the best gag-pol producer clone and was used to introduce env expression vectors for the generation of packaging cell lines.

TABLE 3

Titer following env construct transfection

| Producer cell | Env source | Titer[a] |
|---|---|---|
| psiCRIP lacZ 5 | pCRIPAMgag-envAM | $6 \times 10^{4b}$ |
| GP + EAM12 lacZ 25 | | $3 \times 10^{5b}$ |
| TELCeB6 | FBASALF[c] | $5 \times 10^7$ |
| | FBASAF[c] | $2 \times 10^7$ |
| | FbdelPASAF[c] | $2 \times 10^7$ |
| TELCeB6 | FBdelPASAF 1 | $3 \times 10^7$ |
| | FbdelPASAF 4 | $2 \times 10^7$ |
| | FbdelPASAF 6 | $1 \times 10^7$ |
| | FbdelPASAF 7 | $5 \times 10^7$ |
| | FbdelPASAF 8 | $1 \times 10^7$ |
| | FbdelPRDSAF 2 | $1 \times 10^6$ |
| | FbdelPRDSAF 4 | $3 \times 10^5$ |
| | FbdelPRDSAF 7 | $1 \times 10^7$ |
| | FbdelPRDSAF 8 | $2 \times 10^6$ |
| FLY[d] | FBdelPASAF 1 | $1 \times 10^1$ |
| | FbdelPASAF 4 | $1.5 \times 10^6$ |
| | FbdelPASAF 5 | $1 \times 10^6$ |
| | FbdelPASAF 7 | $1 \times 10^6$ |
| | FbdelPASAF 13 | $7 \times 10^6$ |
| | FbdelPASAF 14 | $4 \times 10^6$ |
| | FbdelPASAF 15 | $1 \times 10^6$ |
| | FbdelPASAF 16 | $5 \times 10^6$ |
| | FbdelPASAF 17 | $6 \times 10^6$ |
| FLYA4 lacZ 3 | FBdelPASAF 4 | $2 \times 10^{7b}$ |
| FLY[d] | FBdelPRDSAF 1 | $2.5 \times 10^6$ |
| | FbdelPRDSAF 2 | $1 \times 10^7$ |
| | FbdelPRDSAF 6 | $5 \times 10^6$ |
| | FbdelPRDSAF 10 | $2 \times 10^6$ |
| | FbdelPRDSAF 11 | $3 \times 10^6$ |
| | FbdelPRDSAF 13 | $1 \times 10^6$ |
| | FbdelPRDSAF 17 | $5 \times 10^6$ |
| | FbdelPRDSAF 18 | $3 \times 10^7$ |
| | FbdelPRDSAF 19 | $6 \times 10^6$ |

Average titers of at least three independent experiments were shown. The standard errors did not exceed 30% of the titer values.
[a]titrated on TE671 cells as lacZ i.u./ml
[b]results of best MFGnlslacZ producer clones.
[c]bulk populations of env-transfectants in TELCeB6 cells.
[d]titration after bulk infection with helper-free MFGnlslacZ.

EXAMPLE 8
Construction of env Expression Vectors.

A series of MLV-A env expression plasmids were then generated (FIG. 1). In FBASALF, the env gene was inserted between two Friend-MLV LTRs, its expression driven by the FB29 MLV LTR (Perryman et al., supra). Most of the packaging signal located in the leader region was deleted. This plasmid also expressed the phleo selectable marker (Gatignol et al., supra) driven by the 3' LTR. FBASAF and FBdelPASAF were then designed following the same strategy used for CeB. These two vectors differed only by the extent of deletion of the packaging signal, FBdelPASAF having virtually no leader sequence. Compared to pCRIPAMgag- and pCRIPgag-2 env plasmids expressed in psiCRIP or psiCRE packaging cells (Danos et al., supra) about 5 Kb of gag-pol sequences was removed. In addition the 258 bp retroviral sequence containing the end of env gene and the begining of U3 found in pCRIPAMgag- and pCRIPgag-2 was also removed. For both FBASAF and FBdelPASAF plasmids, the phleo selectable marker was inserted downstream of the env gene by positioning a 76 nts linker with no ATG codons between the two open-reading frames. Phleo could therefore-only be expressed by re-initiation of translation by the same ribosomal unit that had expressed the upstream env open reading frame. FBdelPASAF was also used to generate FBdelPRDSAF, an RD114 envelope expression plasmid (FIG. 1).

After transfection of the env plasmids into TELCeB6 cells (Table 2), bulk populations of phleomycin-resistant colonies were isolated and their production of lacZ virus measured (Table 3). FBASALF gave a titer of $5 \times 10^7$ lacZ-i.u./ml, whilst titers with either FBASAF or FBdelPASAF were $2 \times 10^7$ lacZ-i.u./ml (Table 3). Titers of $5 \times 10^7$ or $10^7$ lacZ-i.u./ml could be obtained with some FBdelPASAF cell clones or FBdelPRDSAF clones, respectively.

As FBdelPASAF has minimal virus-derived sequences and was shown to be the safest construct (see below and Table 4), it and FBdelPRDSAF were used to generate packaging lines from FLY cells (clone HTCeB22, Table 2). Envelope expression of these clones was assayed by interference to challenge with MFGnlslacZ(A) or MFGnlslacZ (RD) pseudotypes produced by TELCeBG/FBdelPASAF-7 or TELCeB6/FBdelPRDSAF-7, respectively (Table 3). The cell lines showing most interference were is cross-infected at high multiplicity with these pseudotypes to provide MFGnlslacZ proviruses, and supernatants were then titrated on TE671 cells (Table 3). FLY-FBdelPASAF-13 (FLYA13 packaging line) and FLY-FBdelPRDSAF-18 (FLYRD18 packaging line) gave the highest productions of lacZ viruses, around $10^7$ lacZ-i.u./ml. The best MFGnlslacZ producer clones derived from either psiCRIP cells (Danos et al., supra) or GP+EAM12 cells (Markowitz et al., supra) gave approximately 50 fold lower titers (Table 3). The lacZ titers of the FLY-derived lines shown in Table 3 are lower than the best TELCeB6-derived lines after transfection of either FBdelPASAF or FBdelPRDSAF (Table 3). However it should be noted that the lacZ provirus expressed in TEL-CeB6 cells was obtained after clonal selection but was introduced polyclonally in FLY-derived env-transfected cell clones. When FLY-FBdelPASAF-4 cells (FLYA4 packaging line), infected with helper-free MFGnlslacZ(RD), were cloned by limiting dilution the best clones (eg. FLYA4lacZ3) were found to produce 20 times more infectious viruses than the bulk population, reaching the range of titers obtained with the best TELCeB6-FBdelPASAF clones (Table 3).

EXAMPLE 9
Assays for Transfer of gag-pol or env Functions

To assay for replication-competent viruses, supernatants were used to infect TEL cells (a clone of TE671 cells harboring an MFGnlslacZ provirus). Infected cells were passaged for 6 days or longer and their supernatants were used for infection of fresh TE671 cells. No transmission of lacZ viruses could be detected (Table 4), demonstrating that the supernatants of pCRIPAMgag-, FBASALF-, FBASAF-, or FBdelPASAF-transfected TELCeB6 cells were helper-free. Similar absence of replication competent recombinant retroviruses was demonstrated using supernatant from a clone of psiCRIP-MFGnlslacZ cells or from two clones of FLYA-MFGnlslacZ cells (Table 4).

There have been reports that helper-free retroviral vector stocks may nevertheless contain recombinant retroviruses (replication incompetent) carrying either gag-pol or env genes (Bestwick et al., Proc Natl Acad Sci USA (1988), 85, 5404–6408, Cosset et al., Virology (1993), 193, 385–395, Girod et al., Virology (1995), in press). To assay for such recombinant retroviruses, mobilisation of an MFGnlslacZ provirus from two indicator cell lines which could cross-complement potential recombinant viruses carrying either gag-pol or env functional genes was attempted. The TEL-CeB6 line (Table 2) expressing gag-pol proteins was used as indicator cell line to test for the presence of env recombinant (ER) viruses. The TELMOSAF indicator line expressing MoMLV env glycoproteins (obtained by transfection of FBMOSAF, a plasmid expressing the MoMLV env gene using FBASAF backbone, in TEL cells) was used to detect the presence of gag-pol recombinant retroviruses (GPR viruses). After passaging 4–8 days, the supernatants of the infected indicator cells were used to infect either human TE671 cells or murine NIH3T3 cells.

TELCe26 cells transfected with various env-expressing constructs, pCRIPAMgag-, FEASAF and FBdelPASAF were compared. Although the supernatants of TELCeB6-FBdelPASAF cells were devoid of replication-competent retroviruses, they were found sporadically to transfer gag-pol genomes (Table 4). No GPR viruses could be detected when less than $2 \times 10^5$ virions were used to infect the indicator cells. Similarly TELCeB6 indicator cells infected with various helper-free viruses were shown sporadically to release lacZ virions (Table 4). The number depended both on the env-expression vector used and on the virus input quantity. Compared to lacZ viruses generated using pCRIPAMgag-plasmid, the frequency of detection of the env-recombinant viruses was lower for supernatants generated by using FBASAF and FBdelPASAF constructs (Table 4). For FBdelPASAF construct when less than $5 \times 10^5$ MFGnlslacZ(A) helper-free virions were used to infect the indicator cells, no ER retroviruses could be detected. From these experiments, it could be estimated that a supernatant, produced from TELCeB6-FBdelPASAF cells, containing $1 \times 10^7$ infectious units of MFGnlslacZ retroviral vector contained no replication-competent virus, and about 100 gag-pol and 100 env recombinant retroviruses.

TABLE 4

Transfer of packaging function

| Producer cell | Indicator cell | Input virus$^a$ (lacZ-i.u.) | Detection$^b$ ++ | + | - |
|---|---|---|---|---|---|
| Replication competent virus | | | | | |
| psiCRIP lacZ 5 | TEL | $2 \times 10^4$ | 0/4 | 0/4 | 4/4 |
| TELCeB6-pCRIPAMgag- | TEL | $5 \times 10^6$ | 0/4 | 0/4 | 4/4 |
| TELCeB6-FBASAF | TEL | $5 \times 10^6$ | 0/4 | 0/4 | 4/4 |
| TELCeB6-FBdelPASAF | TEL | $5 \times 10^6$ | 0/4 | 0/4 | 4/4 |
| FLYA4 lacZ 3 | TEL | $1 \times 10^7$ | 0/4 | 0/4 | 4/4 |
| FLYA4 lacZ 7 | TEL | $1 \times 10^7$ | 0/4 | 0/4 | 4/4 |
| Gag-pol recombinant | | | | | |
| TELCeB6-FBdelPASAF 7 | TELMOSAF | $2 \times 10^7$ | 0/4 | 1/4 | 3/4 |
| TELCeB6-FBdelPASAF 7 | TELMOSAF | $2 \times 10^6$ | 0/4 | 2/4 | 2/4 |
| TELCeB6-FBdelPASAF 7 | TELMOSAF | $2 \times 10^5$ | 0/4 | 2/4 | 2/4 |
| TELCeB6-FBdelPASAF 7 | TELMOSAF | $2 \times 10^4$ | 0/4 | 0/4 | 4/4 |
| Env recombinent | | | | | |
| TELCeB6-pCRIPAMgag- | TELCeB6 | $5 \times 10^6$ | 2/4 | 1/4 | 1/4 |
| TELCeB6-pCRIPAMgag- | TELCeB6 | $5 \times 10^5$ | 1/4 | 1/4 | 2/4 |
| TELCeB6-pCRIPAMgag- | TELCeB6 | $5 \times 10^4$ | 0/4 | 2/4 | 2/4 |
| TELCeB6-FBASAF | TELCeB6 | $5 \times 10^6$ | 0/4 | 2/4 | 2/4 |
| TELCeB6-FBASAF | TELCeB6 | $5 \times 10^5$ | 0/4 | 1/4 | 3/4 |
| TELCeB6-FBASAF | TELCeB6 | $5 \times 10^4$ | 0/4 | 1/4 | 3/4 |
| TELCeB6-FBdelPASAF | TELCeB6 | $5 \times 10^6$ | 0/4 | 1/4 | 3/4 |
| TELCeB6-FBdelPASAF | TELCeB6 | $5 \times 10^5$ | 1/4 | 3/4 | 0/4 |
| TELCeB6-FBdelPASAF | TELCeB6 | $5 \times 10^4$ | 0/4 | 0/4 | 4/4 |

$^a$number of lacZ i.u. used to infect indicator cells
$^b$number of incidence out of four experiments. The ranges of lacZ titers rescued from infected indicator cells are shown for each virus input: >100 lacZ i.u./ml (++) 1–100 lacZ i.u./ml (+) and <1 lacZ i.u./ml (–).

Titers were determined on TE671 cells for replication competent virus and env recombinant and NIH3T3 cells for gag-pol recombinant.

EXAMPLE 10

In order to confirm resistance to complement and absence of replication competent virus in our best packaging lines, MFGnlslacZ(A) and (RD) harvested from FLYA13 and FLYRD18, respectively, after polyclonal transduction of MFGnlslacZ (Table 3 above) were tested for stability in fresh human serum and generation of replication competent virus. Titers of MFGnlslacZ(RD) from FLYRD18 after 1 hr incubation with 3 independent samples of fresh human serum were 80 to 120% of control incubations, while titers of MFGnlslacZ(A) from FLYA13 were 50 to 90% of controls (data not shown). No replication competent virus was detected in the same assay described above (Table 4) when $1 \times 10^7$ i.u. each of MFGnlslacZ(A) and (RD) were tested.

EXAMPLE 11

Generation of Plasmids

CeB plasmid (FIG. 5) expressing MoMLV gag-pol gene, was further modified to remove the splice donor site located in the leader region. A 272 bp fragment was PCR-generated by using OUSD-(5'-TCTCGCTTCTGTTCGCGCGC SEQ ID NO: 16) and OLSD-(5'-TCGATCAAGCTTGCGGCCGCGGTG-GTGGGTCGGTGGTCC SEQ ID NO: 17) as primers and further digested with BssHII and HindIII. A 1008 bp HindIII-XhoI fragment isolated from CeB (encompassing a part of leader sequence and beginning MoMLV gag) and the PCR fragment were co-inserted into pCeB from which the 1275 bp BssHII-XhoI fragment (encompassing R-U5-leader-gag) had been removed. The resulting plasmid, named pCeB DS- (FIG. 5), beared the deletion of splice donor (SD) site and a NotI restriction site created just downstream to the lost SD site.

A series of gag-pol expression plasmids in which the MoMLV LTR promoter was replaced by the human cytomegalovirus immediate early promoter (hCMV promoter) was derived from both CeB DS- and hCMV-G (Yee et al., 1994 PNAS, 91: 9564–9568), a plasmid used as a source for the hCMV promoter. A NotI-filled/EcoRI 7260 bp fragment was isolated from CeB DS- and cloned into hCMV-G which had been opened with SalI (further rendered blunt-ended) and EcoRI to remove the VSV-G gene. The resulting plasmid was cutted with ClaI and EcoRI to remove a 1155 bp fragment encompassing sequence derived from 3'-LTR and SV40 polyA sequence and self-ligated after filling both protruding DNA ends. The resulting plasmid, named phCMV-intron (FIG. 5), had gag-pol and bsr ORFs inserted between the CMV promoter and rabbit beta-globin polyA post-transcriptional regulatory sequences.

An intermediate plasmid was generated by sub-cloning a 7260 bp EcoRI fragment (isolated from CeB DS-) into hCMVG opened with EcoRI. A 1155 bp fragment (encompassing sequence derived from 3'-LTR and SV40 polyA sequence) was removed from this intermediate plasmid which was then re-circularized by self ligation after filling both ends. The resulting plasmid, named phCMV+intron 2P (Fig. 5), was digested with NotI and the vector was treated with klenow enzyme. A 1440 bp fragment (encompassing hCMV promoter and rabbit beta-1 globin intron B (Rohrbaugh et al., 1985 Mol. Cell Biol, 5: 147–160)) was isolated from phCMV+intron 2P by NotI/EcoRI digestion. This fragment was further treated with klenow enzyme and ligated back into the vector. The resulting plasmid, named hCMV+intron (FIG. 5), could express gag-pol and bsr genes driven by the hCMV promoter and beared an intron sequence derived from rabbit beta-1 globin intron B having both SD and SA (splice acceptable) sites.

A 2450 bp fragment was removed from phCMV+intron 2P by NotI/XhoI digestion. The resulting vector fragment was then used to co-ligate a 1330 bp fragment (containing hCMV promoter +5' end of rabbit beta-1 globin intron B (with SD site)) isolated from phCMVG by ApaI-filled/NotI digestion and a 1 kb fragment isolated from phCMV+intron 2P by NotI-filled/XhoI digestion. Compared to phCMV+ intron 2P, the resulting plasmid, named hCMV+SD intron (FIG. 5), had the deletion of the 3' end of the rabbit beta-1 globin intron B and thus no SA site in the leader region.

Construct phCMV+leader (FIG. 5) has been described elsewhere (Savard et al., unpublished). This plasmid, in which gag-pol and bsr genes were driven by the hCMv promoter, had the MoMLV SD site in the leader region.

Gag-pol expression

The different constructs, including the parental CeB plasmid, were analysed comparatively in a complementation assay after transfection in TEL-FBdelPASAF cells expressing 4070A-MLV (amphotropic) envelope and harboring a MFGnlslacZ provirus. The transient production of lacZ retroviruses as well as the stable production of lacZ retroviral vectors after selection with blasticidin S were determined (Table 5). All the constructs were able to rescue infectious lacZ retroviruses indicating the expression of gag-pol proteins after transient transfection. Most likely due to the efficient hCMV and rabbit beta-1 globin intron B (post)-transcriptional regulatory sequences, hCMV+intron was particularly potent in transient retroviral vector production. However, 10 times less blasticidin-resistant colonies were obtained with hCMV+intron comparatively to CeB, and stable lacZ virus production from hCMV+intron was about 5–10 times lower than that of CeB. Clonal examination of lacZ retrovirus production from blasticidin-resistant colonies indicated that 80–90% of colonies could express high levels of gag-pol proteins for both hCMV+intron and CeB plasmids. In contrast, despite variation in their ability to form blasticidin-resistant colonies after transfection and despite their ability to express gag-pol proteins from transient transfectants, all other constructs had a weak capacity for rescuing lacZ retroviral vectors from stable transfectants (Table 5).

TABLE 5

Comparative study of gag-pol-bsr plasmids.

| gag-pol-bsr plasmid | Transient (lacZ i.u./ml) | no clones bsr+ | Stable (lacZ i.u./ml | % gag-pol/ bsr |
|---|---|---|---|---|
| Ceb | 300/ml | 50 | $10^7$ | 90% |
| Ceb DS- | 144/ml | 5 | $10^5$ | 50% |
| hCMV + intron 2P | ND | 20 | $10^6$ | 50% |
| hCMV − intron | 812/ml | 0 | — | — |
| hCMV + SD intron | 150/ml | 1000 | $10^2$ | nd |
| hCMV + leader | 328/ml | 1000 | $10^2$–$10^3$ | nd |
| hCMV + intron | 12000/ml | 5 | $10^6$–$10^7$ | 80% |

Northern blot analyses were performed on stable transfectants (blasticidin-resistant) obtained with some of the gag-pol-bsr plasmids. As expected, the results (not shown) displayed a correlation between expression of gag-pol mRNAs and gag-pol protein expression detected by rescue analysis (Table 5). CeB construct was found to produce 2–3 fold more gag-pol mRNAs compared to hCMV+intron. Interestingly, an unexpected 2.45 kb RNA band was found for hCMV+intron construct at a ratio of 2:1 compared to the abundancy of the gag-pol mRNA band (at 5.95 kb). Further investigations by using other probes revealed that a cryptic splice donnor (SD) site located in the gag gene (right in the middle of the CA coding region at position 1596–1597 —numbering according to Shinnick et al., 1981 Nature (London) 293: 543–548) was activated in this latter construct. The 2.45 RNA species, lacking the 3' half of the gag gene and most of the pol gene, is unlikely to give rise to any useful any useful translational product. It is therefore interesting to notice that hCMV+intron construct was able to give rise to slightly more transcripts (gag-pol 5.95 mRNA +2.45 alternative RNA band) compared to gag-pol mRNA expressed from CeB construct. Therefore we decided to inactivate the cryptic SD site in the hCMV+intron construct in order to increase the ratio of gag-pol mRNAs.

Assays for Transfer of gag-pol Functions

Although the supernatants of pacakaging cell lines generated with CeB gag-pol expression contruct were devoid of replication-competent retroviruses, they were found sporadically to transfer gag-pol genomes (example 9, Table 4) (Cosset et al., 1995 J. Virol 69: 7430–7436). Because gag-pol-bsr constructs generated here by using the hCMV promoter had much less retroviral sequences homologous to the retroviral vector than the parental CeB construct (FIG. 5), they are less likely to give rise to gag-pol recombinant (GPR) viruses. Therefore, the most efficient gag-pol-bsr plasmids, hCMV+intron and CeB, were further analysed for emergence of GPR viruses. To assay for such recombinant retroviruses, we attempted to mobilise an lacZ provirus from an indicator cell lines which could cross-complement potential recombinant viruses carrying gag-pol functional genes. Results displayed in Table 6 showed that consistently with data reported previously (example 9, Table 4) (Cosset et al., 1995 Supra), lacZ retrovirus vectors generated by using CeB gag-pol construct were contaminated with GPR viruses. In contrast lacZ retrovirus vectors generated by using hCMV+ intron construct were completely devoid of such GPR viruses, suggesting that this construct was improved compared to CeB with respects with emergence of recombinant viruses.

TABLE 6

Comparative study of gag-pol-bsr plasmids.

| plasmid | input virus (lacZ i.u.)[a] | no of experiments giving titers of[b] | | |
|---|---|---|---|---|
| CeB | $5 \times 10^6$ | 5 | 3 | 0 |
| | $5 \times 10^5$ | 2 | 4 | 2 |
| | $5 \times 10^4$ | 0 | 1 | 7 |
| hCMV + intron | $5 \times 10^6$ | 0 | 0 | 8 |
| | $5 \times 10^5$ | 0 | 0 | 8 |
| | $5 \times 10^4$ | 0 | 0 | 8 |

4 x 10E4 cells of TEL/MOSAF in 24 wells were challenged with lacZ(A) of i.u. indicated in the table (a), and incubated at 37° C. for 3 days. Cells were trypsinized and transferred into small flasks. Cell sup was harvested on day 5 after lacZ(A) challenge and plated on either TE571 (not shown) and 3T3 cells (b). No lacZ was mobilized into TE671 at all. LacZ(A) from CMV-int 10 again did not rescue lacZ from TEL/MOSAF.

EXAMPLE 12

Generic primers to detect D-type (Medstrand and Blomberg J. Virol. (1993) 67: 6778–6787) (SEQ ID NOS: 22 & 23), C-type (Shih et al., J Virol. (1989) 63: 64–75) (SEQ ID NOS: 20 & 21), human endogenous virus RTVL-H (Wilkinson et al., J. Virol. (1993) 67: 2981–2989) (SEQ ID NOS: 24 & 25), by RT-PCR were employed (Patience et al., supra). Primers to detect mouse endogenous VL30 element (Adams et al Mol. Cel. Biol. (1988) 8: 2989–2998) (SEQ ID NOS: 26 & 27), and MFGnlslacZ RNA (SEQ ID NOS: 18 & 19) were designed and synthesized (TABLE 7). Overnight supernatants (in 4 ml of culture medium) from 106 cells of GP+EAM121acZ25, FLYA41acZ3 and TELCeB6FBASALF cells (Table 3) were harvested and centrifuged in sucrose gradient as described previously (Patience et al., J.Virol., 70: 2654–2657). Fractions containing retrovirus particles were collected, and RNA extracted. One twentieth of the RNA preparation or dilution's thereof were applied to RT-PCR as described previously (Table 7). A 1/200 of RNA harvested from GP+EAM121acZ25 cells was positive for VL30 RNA. MFGnlslacZ RNA was found from 1/20 of RNA from GP+EAM121acZ and TELCeB6FBASALF cells and 1/200 of RNA from FLYA41acZ3 cells. The primer combinations for RTVL-H, C- and D-type RNA did not give detectable PCR product.

of pools of phleomycin-resistant colonies for each TECB-lacZ-FBMOSALF lines. A good correlation was found between gag-pol expression into the TE-CeB clones (as determined by RT-assays and anti-gag immunoblots) and their ability to release infectious lacZ particles. TE-CeB15 cells could release approximately the same number of lacZ particles when compared to TELCeB6 cells although TEL-CeB6 cells had the advantage of being selected for lacZ expression (Cosset et al., J. Virol. 69: 7430–7436 (1995)). TE-CeB15 cells were therefore used to derive retroviral packaging cell lines.

TABLE 7

RT-PCR detection of endogenous retrovirus RNA associated with virus particles.

| RNA | primer (5'-3') forward (F)/reverse (R) | | | rt-pcr of virion associated RNA from[a] | | |
|---|---|---|---|---|---|---|
| | | | | GP + EAM12 lacZ25 | FLYA4 lacZ3 | TELCeB6F BASALF |
| MFGnls | F) | CTCTGGCTCACAGTACGACGTAG | SEQ ID NO: 18 | + | ++ | + |
| lacZ | R) | CCATCAATCCGGTAGGTTTTCCG | SEQ ID NO: 19 | | | |
| C-type | F) | CARRGKTTCAARAACWSYCCCAC | SEQ ID NO: 20 | – | – | – |
| | R) | AGYARVGTAGCNGGGTTHAGG | SEQ ID NO: 21 | | | |
| D-type | F) | TCCCCTTGGAATACTCCTGTTTTYGT | SEQ ID NO: 22 | – | – | – |
| | R) | CATTCCTTGTGGTAAAACTTTCCAYTG | SEQ ID NO: 23 | | | |
| RTVL-H | F) | CCTCACCCTGATCACRYTTG | SEQ ID NO: 24 | NT | – | – |
| | R) | GAATTATGTCTGACAGAAGGG | SEQ ID NO: 25 | | | |
| VL30 | F) | GTTGACATCTGCAGAGAAAGACC | SEQ ID NO: 26 | ++ | NT | NT |
| | R) | TCTGAGGTCTGTACACACAATGG | SEQ ID NO: 27 | | | | a:–, not detected;
+ detected in 1/20 RNA preparation;
++ detected in 1/200 RNA preparation;
NT, not tested because the cells do not possess the corresponding genes.

EXAMPLE 13
Generation of gag-pol Pre-packaging Cells by Using TE671 Cells

CeB, a plasmid designed to over-express MoMLV gag and pol proteins was introduced in TE671 human rhabdomyosarcoma cells (ATCC CRL8805). After selection with blasticidin, 50 bsr-positive colonies were isolated and the RT (reverse transcriptase) activity was analysed in their supernatants. 12 TE671-CeB (TECeB) clones with high RT activity were selected for further analysis. The best TECeB clone, clone #15, had a RT activity roughly equivalent to that TELCeB6 cells (Cosset et al., J. Virol. 69: 7430–7436 (1995); see also Example 7, Table 6 in this patent application) but displayed 2–3 fold more gag-precursors into cells as demonstrated in immunoblots by using anti-CA antibodies. The biological activity of gag-pol proteins expressed in the six best TECeB clones was further confirmed by their ability to produce infectious retroviruses in a complementation assay. A lacZ provirus was introduced into each of the TECeB clones by polyclonal cross-infection by using lacZ(RD114) helper-free retrovirus vectors. FBMOSALF, a MoMLV env expression plasmid (Cosset et al., J. Virol. 69: 6314–6322), was then transfected in each of the TECeB-lacZ lines and in the TELCeB6 cell line for comparison. After selection with phleomycin, the titer of lacZ retrovirus vectors was determined in the supernantant Construction of env-expression Plasmids.

A series of plasmid (FIG. 3) was designed to allow expression of different retroviral envelope genes (isolated from MoMLV, GALV -Gibbon Ape Leukemia Virus-, and MLV-10A1) FBdelPMOSAF (FIG. 3, nucleotide sequence in FIG. 10 SEQ ID NO: 6) and FBdelP10A1SAF, expressing ecotropic MoMLV or MLV-10A1 envelopes, were generated by replacing the BglII/ClaI fragment from FBdelPASAF (Cosset et al., J. Virol. 69: 7430–7436 (1995); see also Example 7, FIG. 2 and nucleotide sequence in FIG. 9 SEQ ID NO: 5) encompassing most of the env gene and splice acceptor site with that of MoMLV (position 5407 to 7679, Shinnik et al., 1981) or with that of MLV-10A1 (Ott et al., J. Virol. 64: 757–766 (1990)).

Nucleotides 7514–7516 of GALV (Delassus et al., Virology 173: 205–213 (1989)) were mutated by PCR-mediated mutagenesis to create a ClaI site (AAG to CGA), thereby introducing a conservative modification (a lysine (amino-acid 665 of GALV env precursor) to an arginine). The BamHI/ClaI fragment (nts 4994 (Delassus et al. Virology 173: 205–213 (1989)) to 7517) was then sub-cloned into FBdelPASAF in which the EglII/ClaI encompassing most of the env gene and splice acceptor site had been removed. The resulting plasmid, expressing GALV envelope glycoproteins, was named FBdelPGASAF (FIG. 3, nucleotide sequence in FIG. 11 SEQ ID NO: 7). CMV10A1 was generated by inserting a Klenow enzyme-filled EagI/SalI fragment from FBdelPlOAlSAF (encompassing 10A1 MLV env gene and phleo selectable marker) into hCMV-G digested with BamHI and filled with Klenow enzyme. The resulting plasmid, CMV10A1 (FIG. 3 and nucleotide sequence in FIG. 13) could express 10A1 envelopes under control of the hCMV promoter and the phleo selectable marker by translation re-initiation.

Generation of a Multi-tropic Set of TE671-based Retroviral Packaging Lines

FBdelPRDSAF (FIG. 3, nucleotide sequence in FIG. 12 SEQ ID NO: 12), FBdelPASAF, FBdelPGASAF, FBdelP-MOSAF and FBdelP10AlSAF were independently introduced into cells of the TE-CeB15 pre-packaging line, expressing MoMLV gag-pol proteins. Transfected cells were phleomycin-selected and 15–20 phleo-resistant colonies were isolated for each env-expression plasmid transfected.

Individual colonies were then analysed for expression of envelope glycoproteins by immunoblots on cell lysates by using antibodies against RD114 SU glycoproteins or against Rausher leukemia virus SU (to screen MoMLV, MLV-4070A and MLV-10A1 env-producer clones) or against GALV. The best env-producer colonies as determined in this assay were further analysed by a complementation assay after introducing a lacZ retroviral vector. LacZ pseudotypes released from the different packaging cell lines were titrated by using NIH 3T3 cells or TE671 cells as target. Titers higher than $1 \times 10^7$ lacZ i.u./ml were obtained for the best clones. Depending on the envelope specificities expressed in these cells, the new TE671-based retroviral packaging cell lines were named TE-FLYE, TE-FLYA, TE-FLYRD, TE-FLY10A1, and TE-FLYGA and could express the MoMLV, MLV-4070A, RD114, MLV-10A1, and GALV env genes, respectively.

Assays for detecting replication-competent retroviruses (RCRs) were performed in the supernatants of these cells and were negative (less than 1/ml).

TE671 cells are very potent for transient expression resulting in more than 95% of cells expressing transgene three days after plasmid transfection (Hatziioannou and Cosset, unpublished data, (1996)). The ability of retroviral packaging cell lines to transiently produce retroviral vectors is of crucial importance for gene therapy where vectors carrying toxic gene have to be prepared. Transient expression of retroviral vectors was comparatively determined from cells of the TE-FLYA line and from the BING line (Pear et al., Proc Natl Acad Sci U S A 90, 8392–6 (1993)), a retroviral packaging cell line designed to transiently express retroviral vectors. Results (Table 8) showed that TE-FLYA cells were more efficient for transient expression of a lacZ retroviral vector hence resulting in higher titers.

TABLE 8

Comparative study of transient production of lacZ vectors.

| packaging cell line | cell number[a] | % transfected cells[b] | transient titer[c] |
| --- | --- | --- | --- |
| BING | 281 | 5.3 | $2 \times 10^2$ |
| TE-FLYA | 117 | 35 | $1.3 \times 10^3$ |

Cells were transfected by MFGnlslacZ retroviral vectors with calcium phosphate precipitation method and titers of of lacZ vectors (c) released in cell supernatant were determined as lacZ i.u./ml at day 3 following transfection. The relative number of cells (a) (average per microscope field) and the % of transfected cells (b) determined after X-gal staining are shown.

Retroviral vectors prepared from TE671-based packaging cell lines were analysed for their sensitivity to human-complement mediated inactivation. Experiments were conducted as previously described (Cosset et al., J. Virol. 69: 7430–7436 (1995); see also Example 10 in this patent application) by using three human sera of individual donnors (Table 9). As expected MLV-A prepared from mouse 3T3 cells were highly sensitive to inactivation after 1 hr incubation witn sera. In contrast, titers of lacZ vectors produced from TE-FLYRD cells were 17 to 55% of control incubations, while titers of lacZ vectors from TE-FLYA cells were 1 to 30% of controls.

TABLE 9

Human serum sensitivity oif viruses produced from TE671-based packaging cell lines.

| Virus from: | hu56[a] | hu57[a] | BTS[a] |
| --- | --- | --- | --- |
| 3T3/A | <0.2, <0.2 | <0.2, <0.2 | <0.2, <0.2 |
| TE-FLYE | 15, 7.8 | 16, 11 | 48, 60 |
| TE-FLYA | 1, 0.6 | 2.2, 7.1 | 28, 19 |
| TE-FLYRD | 17, 22 | 30, 44 | 54, 63 |

Three human fresh serum samples were tested in duplicate; hu56 (A+), hu57 (AB+), BTS (AB+). (a) % control (average for FCS and opti-MEM treatment) is shown.

We claim:

1. A recombinant expression vector comprising a gene of interest and a selectable marker gene, wherein the selectable marker gene is arranged downstream of the gene of interest and a stop codon associated with the gene of interest is spaced from a start codon of said selectable marker gene at a distance which is sufficient to ensure that said selectable marker protein is expressed from the corresponding mRNA as a result of translation reinitiation.

2. A recombinant expression vector according to claim 1 wherein the vector is a viral vector.

3. A recombinant expression vector according to claim 1 wherein the gene of interest is included as part of a viral packaging construct.

4. A recombinant expression vector according to claim 1, wherein the number of nucleotides in the space between the stop codon of the gene of interest and the start codon of the selectable marker is in the range of from 20 to 200 nucleotides.

5. A host cell transformed with a recombinant expression vector according to claim 1.

6. A retroviral packaging cell line according to claim 1, wherein a packaging-deficient construct comprising a viral env gene and second selectable marker is the FBdelPASAF (SEQ ID No. 5), the FBdelPMOSAF (SEQ ID No. 6), FbdelPGASAF (SEQ ID No. 7), the FbdelPRDSAF (SEQ ID No. 8), the FbdelPXSAF (FIG. 3), the FbdelP10A1SAF (FIG. 3), or the FbdelPVSVGSAF (FIG. 3) expression construct.

7. A recombinant expression vector according to claim 2 wherein the vector is a retroviral vector.

8. A recombinant expression vector according to claim 7, wherein the vector is a human complement-resistant retroviral vector.

9. A recombinant expression vector according to claim 4, wherein the number of nucleotides in the space between the stop codon of the gene of interest and the start codon of the selectable marker is in the range of from 60 to 80 nucleotides.

10. A nucleic acid construct comprising a gene of interest and a selectable marker gene, the selectable marker gene being operably linked 3' to the gene of interest, said gene of interest associated with a stop codon spaced from a start codon of said selectable marker gene at a distance sufficient to ensure that said selectable marker protein is expressed from the corresponding mRNA as a result of translation reinitiation.

11. A vector comprising the nucleic acid construct of claim 10.

12. A process for producing a cell line in which a gene of interest is expressed, which process comprises:

transforming host cells with a nucleic acid construct according to claim 10; selecting those cells where expression of the selectable marker gene may be detected, and growing said transformed cells in the presence of a selection agent, thereby producing a cell line expressing said gene of interest.

13. A process according to claim 12, wherein the host cell is a eukaryotic cell.

14. A vector as claimed in claim 11, said vector being selected from the group consisting of plasmids, recombinant retroviral vectors and viral vectors.

15. A retroviral packaging cell line comprising a host cell transformed with a first and a second recombinant expression vector, said first recombinant expression vector having a packaging-deficient construct comprising a viral gag-pol gene and a first selectable marker gene downstream thereof, and said second recombinant expression vector having a packaging-deficient construct comprising a viral env gene and a second selectable marker gene downstream thereof; wherein the start codon of the first and second selectable markers are spaced from the stop codons of the viral gag-pol gene and the viral env gene respectively by a distance which ensures that said selectable marker protein is expressed from the corresponding mRNA as a result of translation reinitiation.

16. A retroviral packaging cell line according to claim 15, wherein said retroviral packaging cell line is human complement-resistant.

17. A retroviral packaging cell line according to claim 15, wherein the first selectable marker is a bsr selectable marker and the second selectable marker is a phleo selectable marker.

18. A retroviral packaging cell line according to claim 15, wherein the packaging-deficient construct comprising the viral gag-pol gene and first selectable marker is the CeB (SEQ ID No. 2) expression construct.

19. A retroviral packaging cell line according to claim 15, wherein recombinant expression vector is a packaging-deficient retroviral helper construct.

20. A retroviral packaging cell line according to claim 15, wherein the viral gag-pol gene and the selectable marker are expressed under the control of a non-retroviral promoter.

21. A retroviral packaging cell line according to claim 15, wherein the viral env gene and the selectable marker are under the control of a non-retroviral promoter.

22. A retroviral packaging cell line according to claim 15, wherein the cell line is the HT1080 line, the TE671 line, the 3T3 line, the 293 line or the MV-1-1U line.

23. A retroviral packaging cell line according to claim 15, wherein the retroviral packaging cell is a human HT 1080 cell and expresses RD114 envelopes.

24. A retroviral packaging cell line according to claim 15, wherein said second recombinant expression vector is a packaging-deficient retroviral helper construct.

25. A retroviral packaging cell line according to claim 17, wherein the retroviral packaging cells comprises human TE671 cells and express RD114 envelopes.

26. A retroviral packaging cell line according to claim 19, wherein overlapping sequences between genomes of a retroviral vector sequence and a packaging-deficient construct are reduced by minimizing the extent of non-coding retroviral sequences in a packaging deficient genome.

27. A retroviral packaging cell line according to claim 20, wherein the promoter is fused to rabbit beta-1 globin intron.

28. A retroviral packaging cell line according to claim 20, wherein the promoter is a hCMV promoter.

29. A retroviral packaging cell line according to claim 20, wherein the viral gag-pol gene and the selectable marker is a hCMV+intron (SEQ ID No. 3) or a hCMV+intronkaSD (SEQ ID No. 4) expression construct.

30. A retroviral packaging cell line according to claim 21, wherein the promoter is fused to rabbit beta-1 globin intron.

31. A retroviral packaging cell line according to claim 21, wherein the promoter is a hCMV promoter.

32. A retroviral packaging cell line according to claim 21, wherein the viral env gene and the selectable marker is a CMV10A1 (SEQ ID No. 9) expression construct.

33. A process for producing a retroviral packaging cell line in which at least one gene of interest is expressed, which process comprises:

transforming host cells with a first and a second recombinant expression vector, said first recombinant expression vector having a packaging-deficient construct comprising a viral gag-pol gene, said gag-pol gene optionally being operably linked to a gene of interest and a first selectable marker gene downstream thereof, and said second recombinant expression vector having a packaging-deficient construct comprising a viral env gene, said env gene optionally being operably linked to a gene of interest and a second selectable maker gene downstream thereof; wherein the start codon of the first and second selectable markers are spaced from the stop codons of the viral gag-pol gene and the viral env gene respectively by a distance which ensures that said selectable marker protein is expressed from the corresponding mRNA as a result of translation reinitiation; and selecting transformed cells which express at least one and optionally both first and second marker genes, thereby producing a retroviral packaging cells line expressing said at least one gene of interest.

34. A packaging deficient construct for use in a process according to claim 33, which expresses a viral gag-pol gene and a selectable marker wherein a start codon of the selectable marker is spaced from a stop codon of the viral gag-pol gene by a distance which ensures that said selectable marker protein is expressed from the corresponding mRNA as a result of translation reinitiation.

35. A packaging deficient construct for use in a process according to claim 33, which expresses a viral env gene and a selectable marker gene; wherein a start codon of the selectable marker is spaced from a stop codon of the viral env gene by a distance which ensures that said selectable marker protein is expressed from the corresponding mRNA as a result of translation reinitiation.

* * * * *

EX PARTE REEXAMINATION CERTIFICATE (6179th)
United States Patent
Collins et al.

(10) Number: US 6,165,715 C1
(45) Certificate Issued: Apr. 8, 2008

(54) EXPRESSION SYSTEMS

(75) Inventors: Mary Katherine Levinge Collins, London (GB); Robin Anthony Weiss, London (GB); Yasuhiro Takeuchi, London (GB); Francois-Lois Cosset, Lyons (FR)

(73) Assignee: Cancer Research Campaign Technology Limited Regents Park, London (GB)

Reexamination Request:
No. 90/007,898, Jan. 26, 2006

Reexamination Certificate for:
Patent No.: 6,165,715
Issued: Dec. 26, 2000
Appl. No.: 09/011,745
Filed: Jun. 22, 1998

(22) PCT Filed: Aug. 23, 1996
(86) PCT No.: PCT/GB96/02061
§ 371 (c)(1), (2), (4) Date: Jun. 22, 1998
(87) PCT Pub. No.: WO97/08330
PCT Pub. Date: Mar. 6, 1997

(51) Int. Cl.
*C12N 15/67* (2006.01)
*C12N 15/867* (2006.01)

(52) U.S. Cl. .................. 435/6; 435/320.1; 435/325; 435/354; 435/366; 435/371; 435/372.1; 435/455; 435/456; 435/69.1; 536/23.1; 536/24.1

(58) Field of Classification Search .................. None
See application file for complete search history.

(56) References Cited

FOREIGN PATENT DOCUMENTS

| WO | WO 93/03143 | 2/1993 |
| WO | WO 93/25698 | 12/1993 |
| WO | WO 94/23048 | 10/1994 |
| WO | WO 94/24870 | 11/1994 |
| WO | WO 97/08330 | 3/1997 |

OTHER PUBLICATIONS

Luukkonen et al., "Efficiency of Reinitiation of Translation on Human Immunodeficiency Virus Type 1 mRNAs is Determined by the Length of the Upstream Open Reading Frame and by Intercistronic Distance," Journal of Virology, 69(7):4086–4094 (1995).

Herzog et al., "Translation of the Second Gene of Peanut Clump Virus RNA 2 Occurs by Leaky Scanning in Vitro," Virology 208:215–225 (1995).

Fouillot et al., "Translation of the Hepatitis B Virus P Gene by Ribosomal Scanning as an Alternative to Internal Initiation," Journal of Virology, 67(8):4886–4895 (1993).

Lin and Lo, "Evidence for Involvement of a Ribosomal Leaky Scanning Mechanism in the Translation of the Hepatitis B Virus Pol Gene from the Viral Pregenome RNA," Virology, 188:342–352 (1992).

Cosset et al., "Newcastle Disease Virus (NDV) Vaccine Based on Immunization with Avian Cells Expressing the NDV Hemagglutinin–Neuraminidase Glycoprotein," Virology, 185:862–866 (1991).

Kozak, M., "Effects of Intercistronic Length on the Efficiency of Reinitiation by Eucaryotic Ribosomes," Molecular and Cellular Bioloby, 7(10):3438–3445 (1987).

Izumi et al., "Blasticidin S–Resistance Gene (bsr): A Novel Selectable Marker for Mammalian Cells," Experimental Cell Research, 197:229–233 (1991).

Danos and Mulligan, "Safe and Efficient Generation of Recombinant Retroviruses with Amphotropic and Ecotropic Host Ranges," Proceedings of the National Academy of Sciences USA, 85:6460–6464 (1988).

Cosset et al., "High–Titer Packaging Cells Producing Recombinant Retroviruses Resistant to Human Serum," Journal of Virology, 69(12):7430–7436 (1995).

Liu et al., "Initiation of Translation at Internal AUG Codons in Mammalian Cells," Nature, 309:82–85 (1984).

Levine et al., "Efficient Gene Expression in Mammalian Cells from a Dicistronic Transcriptional Unit in an Improved Retroviral Vector," Gene, 108:167–174 (1991).

*Primary Examiner*—Padmashri Ponnaluri

(57) ABSTRACT

The invention relates to new expression systems and in particular to an expression system in which a gene of interest is expressed at an optimal level. The invention provides a recombinant expression vector comprising a gene of interest and a selectable marker gene, wherein the selectable marker gene is arranged downstream of the gene of interest and a stop codon associated with the gene of interest is spaced from a start codon of said selectable marker gene at a distance which is sufficient to ensure that translation reinitiation is required before said selectable marker protein is expressed from the corresponding mRNA. Examples of such expression systems are vector viral packaging cell lines and a number of preferred cell lines have been identified.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 15–18, 20–22 and 27–32 is confirmed.

Claims 1–14 and 24 are cancelled.

Claims 19, 23, 25, 26, 33, 34 and 35 are determined to be patentable as amended.

New claim 36 is added and determined to be patentable.

19. A retroviral packaging cell line according to claim 15, wherein *the first and/or second* recombinant expression vector is a packaging-deficient retroviral helper construct.

23. A retroviral packaging cell line according to claim 15, wherein the retroviral packaging [cell is a] *cells comprise* human HT1080 [cell] *cells* and expresses RD114 envelopes.

25. A retroviral packaging cell line according to claim [17] *15*, wherein the retroviral packaging cells comprises human TE671 cells and express RD114 envelopes.

26. A retroviral packaging cell line according to claim 19, wherein *the* overlapping sequences between *the retroviral* genomes of [a retroviral vector sequence and a packaging-deficient construct are ] *the recombinant expression vectors is* reduced by minimizing the extent of non-coding retroviral sequences in [a genome] *the packaging deficient retroviral helper construct.*

33. A process for producing a retroviral packaging cell line [in which at least one gene of interest is expressed], which process comprises:

transforming host cells with a first and a second recombinant expression vector, said first recombinant expression vector having a packaging-deficient construct comprising a viral gag-pol gene[, said gag-pol gene optionally being operably linked to a gene of interest] and a first selectable marker gene downstream thereof, and said second recombinant expression vector having a packaging-deficient construct comprising a viral env gene[, said env gene optionally being operably linked to a gene of interest] and a second selectable maker gene downstream thereof; wherein the start codon of the first and second selectable markers are spaced from the stop codons of the viral gag-pol gene and the viral env gene respectively by a distance which ensures that said selectable marker protein is expressed from the corresponding mRNA as a result of translation reinitiation; and selecting transformed cells which express [at least one and optionally both] *said* first [and] *and/or* second marker genes[, thereby producing a retroviral packaging cells line expressing said at least one gene of interest].

34. A packaging deficient construct for use in a process according to claim 33, which expresses a viral gag-pol gene and a selectable marker *gene* wherein a start codon of the selectable marker *gene* is spaced *downstream* from a stop codon of the viral gag-pol gene by a distance which ensures that said selectable marker protein is expressed from the corresponding mRNA as a result of translation reinitiation.

35. A packaging deficient construct for use in a process according to claim 33, which expresses a viral env gene and a selectable marker gene; wherein a start codon of the selectable marker is spaced *downstream* from a stop codon of the viral env gene by a distance which ensures that said selectable marker protein is expressed from the corresponding mRNA as a result of translation reinitiation.

*36. A retroviral packaging cell line according to claim 15, wherein the packaging-deficient construct comprising the viral env gene and second selectable marker is the FBdelPASAF (SEQ ID No. 5), the FBdelPMOSAF (SEQ ID No. 6), FbdelPGASAF (SEQ ID No. 7), the FbdelPRDSAF (SEQ ID No. 8), the FbdelPXSAF (FIG. 3), the FbdelP10AlSAF (FIG. 3), or the FbdelPVSVGSAF (FIG. 3) expression construct.*

* * * * *

SEQUENCE LISTING

<160> NUMBER OF SEQ ID NOS: 29

<210> SEQ ID NO 1
<211> LENGTH: 2518
<212> TYPE: DNA
<213> ORGANISM: RD114
<220> FEATURE:
<221> NAME/KEY: misc_feature
<222> LOCATION: (1)
<223> OTHER INFORMATION: n is any nucleotide -continued

```
<400> SEQUENCE: 1
ngagctcagg acaggtagaa agaatgaata gaacaataaa agagacccct actaaattga        60
ccttagagac tggcttaaaa gattggagac gcctcctatc tctggctttg ttaagagcca       120
gaaatacgcc caaccgtttt cggctcaccc catatgaaat cctttatggg ggaccccccc       180
ctttgtcaac cttgctcaat tccttctccc cctccgatcc taagactgat ttacaagccc       240
gactaaaagg gctgcaaggc gtgcaggccc aaatctggac accctggcc gaattgtacc        300 ggccaggaca tccacaaact agccacccat ttcaggtggg agactccgtg tacgtccggc       360
ggcaccgctc tcaaggattg gagcctcgtt ggaagggacc ttacatcgtc ctgctgacca       420
cgcccaccgc cataaaggtt gacgggatcg ccgcctggat tcacgcatcg cacgccaagg       480
cagccccaaa aacccctgga ccagaaactc ccaaaacctg gaagctccgc cgttcggaga       540
accctcttaa gataagactc tcccgtgtct gactgctaat ccaccttgtc cctgtactaa       600
cccaaaatga aactcccaac aggaatggtc attttatgta gcctaataat agttcgggca       660
gggtttgacg accccgcaa ggctatcgca ttagtacaaa aacaacatgg taaaccatgc        720
gaatgcagcg gagggcaggt atccgaggcc ccaccgaact ccatccaaca ggtaacttgc       780
ccaggcaaga cggcctactt aatgaccaac caaaaatgga aatgcagagt cactccaaaa       840
atctcaccta gcgggggaga actccagaac tgcccctgta acactttcca ggactcgatg       900
cacagttctt gttatactga ataccggcaa tgcaggcgaa ttaataagac atactacacg       960
gccaccttgc ttaaaatacg gtctgggagc ctcaacgagg tacagatatt acaaaacccc      1020
aatcagctcc tacagtcccc ttgtagggc tctataaatc agcccgtttg ctggagtgcc       1080
acagccccca tccatatctc cgatggtgga ggacccctcg atactaagag agtgtggaca      1140
gtccaaaaaa ggctagaaca aattcataag gctatgactc ctgaacttca ataccacccc      1200
ttagccctgc ccaaagtcag agatgacctt agccttgatg cacggacttt tgatatcctg      1260
aataccactt ttaggttact ccagatgtcc aattttagcc ttgcccaaga ttgttggctc      1320
tgtttaaaac taggtacccc taccctcttt gcgatacccg ctcctctctt aacctactcc      1380
ctagcagact ccctagcgaa tgcctcctgt cagattatac ctccctctct ggttcaaccg      1440
atgcagttct ccaactcgtc ctgtttatct tccccttca ttaacgatac ggaacaaata       1500
gacttaggtg cagtcacctt tactaactgc acctctgtag ccaatgtcag tagtcctttta      1560 tgtgccctaa acgggtcagt cttcctctgt ggaaataaca tggcatacac ctatttaccc      1620
caaaactgga ccagactttg cgtccaagcc tccctcctcc ccgacattga catcaacccg      1680
ggggatgagc cagtcccccat tcctgccatt gatcattata tacatagacc taaacgagct      1740
gtacagttca tccctttact agctggactg ggaatcaccg cagcattcac caccggagct      1800
acaggcctag tgtctccgt cacccagtat acaaaattat cccatcagtt aatatctgat       1860
gtccaagtct tatccggtac catacaagat ttacaagacc aggtagactc gttagctgaa      1920
gtagttctcc aaaataggag gggactggac ctactaacgg cagaacaagg aggaattgtg      1980
ttagccttac aagaaaaatg ctgttttttat gctaacaagt caggaattgt gagaaacaaa      2040
ataagaaccc tacaagaaga attacaaaaa cgcaggaaa gcctggcaac caaccctctc       2100
tggaccgggc tgcagggctt tcttccgtac ctcctacctc tcctgggacc cctactcacc      2160
ctcctactca tactaaccat tgggccatgc gttttcagtc gcctcatggc cttcattaat      2220
gatagactta atgttgtaca tgccatggtg ctggcccagc aataccaagc actcaaagct      2280
gaggaagaag ctcaggattg agcttccggg acaaaagcag ggggaatga gaagtcagaa      2340
```

-continued

```
cccccccacct tgctacata ataaccgct  ttcatttcgc ttctgtaaaa cgcttatgcg    2400
ccccacccta gccggaaagt ccccagccgc tacgcaaccc gggccccgag ttgcatcagc    2460
cgttcgcaac ccgggctccg agttgcatca gccgaaagaa acttcatttc ccaagctt     2518
```

<210> SEQ ID NO 2
<211> LENGTH: 7616
<212> TYPE: DNA
<213> ORGANISM: Artificial Sequence
<220> FEATURE:
<223> OTHER INFORMATION: Description of Artificial Sequence: Portion of
      construct

<400> SEQUENCE: 2

```
aatgaaagac cccacctgta ggtttggcaa gctagcttaa gtaacgccat tttgcaaggc      60
atggaaaaat acataactga gaatagagaa gttcagatca aggtcaggaa cagatggaac     120
agctgaatat gggccaaaca ggatatctgt ggtaagcagt tcctgccccg gctcagggcc     180
aagaacagat ggaacagctg aatatgggcc aaacaggata tctgtggtaa gcagttcctg     240
ccccggctca gggccaagaa cagatggtcc ccagatgcgg tccagccctc agcagtttct     300
agagaaccat cagatgtttc cagggtgccc caaggacctg aaatgaccct gtgccttatt     360
tgaactaacc aatcagttcg cttctcgctt ctgttcgcgc gcttctgctc cccgagctca     420
ataaaagagc ccacaacccc tcactcgggg cgccagtcct ccgattgact gagtcgcccg     480
ggtacccgtg tatccaataa accctcttgc agttgcatcc gacttgtggt ctcgctgttc     540
cttgggaggg tctcctctga gtgattgact acccgtcagc ggggtctttt catttggggg     600
ctcgtccggg atcgggagac cctgcccag ggaccaccga cccaccaccg ggaggtaagc     660
tggaagcttc tgcagcatcg ttctgtgttg tctctgtctg actgtgtttc tgtatttgtc     720
tgagaatatg ggccagactg ttaccactcc cttaagtttg accttaggtc actggaaaga     780
tgtcgagcgg atcgctcaca accagtcggt agatgtcaag aagagacgtt gggttacctt     840
ctgctctgca gaatggccaa cctttaacgt cggatggccg cgagacggca cctttaaccg     900
agacctcatc acccaggtta agatcaaggt cttttcacct ggcccgcatg gacacccaga     960
ccaggtcccc tacatcgtga cctgggaagc cttggctttt gaccccctc cctgggtcaa    1020 gccctttgta caccctaagc ctccgcctcc tcttcctcca tccgccccgt ctctcccct     1080 tgaacctcct cgttcgaccc cgcctcgatc ctccctttat ccagccctca ctccttctct    1140
aggcgccaaa cctaaacctc aagttctttc tgacagtggg gggccgctca tcgacctact    1200
tacagaagac ccccgccctt atagggaccc aagaccaccc ccttccgaca gggacggaaa    1260
tggtggagaa gcgacccctg cgggagaggc accggacccc tccccaatgg catctcgcct    1320
acgtgggaga cgggagcccc ctgtggccga ctccactacc tcgcaggcat tcccctccg    1380 cgcaggagga acggacagc ttcaatactg gccgttctcc tcttctgacc tttacaactg     1440
gaaaaataat aaccccttctt tttctgaaga tccaggtaaa ctgacagctc tgatcgagtc    1500
tgttctcatc acccatcagc ccacctggga cgactgtcag cagctgttgg ggactctgct    1560
gaccggagaa gaaaaacaac gggtgctctt agaggctaga aaggcggtgc ggggcgatga    1620
tgggcgcccc actcaactgc ccaatgaagt cgatgccgct tttcccctcg agcgcccaga    1680
ctgggattac accaccagg caggtaggaa ccacctagtc cactatcgcc agttgctcct    1740
agcgggtctc caaaacgcgg gcagaagccc caccaatttg gccaaggtaa aggaataac     1800 acaagggccc aatgagtctc cctcggcctt cctagagaga cttaaggaag cctatcgcag    1860
```

```
gtacactcct tatgaccctg aggacccagg gcaagaaact aatgtgtcta tgtctttcat   1920
ttggcagtct gccccagaca ttgggagaaa gttagagagg ttagaagatt taaaaaacaa   1980
gacgcttgga gatttggtta gagaggcaga aaagatcttt aataaacgag aaaccccgga   2040
agaaagagag gaacgtatca ggagagaaac agaggaaaaa gaagaacgcc gtaggacaga   2100
ggatgagcag aaagagaaag aaagagatcg taggagacat agagagatga gcaagctatt   2160
ggccactgtc gttagtggac agaaacagga tagacaggga ggagaacgaa ggaggtccca   2220
actcgatcgc gaccagtgtg cctactgcaa agaaaagggg cactgggcta agattgtcc    2280 caagaaacca cgaggacctc ggggaccaag accccagacc tccctcctga ccctagatga   2340
ctagggaggt cagggtcagg agccccccc tgaacccagg ataaccctca aagtcggggg    2400
gcaacccgtc accttcctgg tagatactgg ggcccaacac tccgtgctga cccaaaatcc   2460 tggacccta agtgataagt ctgcctgggt ccaaggggct actggaggaa agcggtatcg    2520
ctggaccacg gatcgcaaag tacatctagc taccggtaag gtcacccact ctttcctcca   2580
tgtaccagac tgtccctatc ctctgttagg aagagatttg ctgactaaac taaaagccca   2640
aatccacttt gagggatcag gagctcaggt tatgggacca atggggcagc ccctgcaagt   2700
gttgacccta aatatagaag atgagcatcg gctacatgag acctcaaaag agccagatgt   2760
ttctctaggg tccacatggc tgtctgattt tcctcaggcc tgggcggaaa ccgggggcat   2820
gggactggca gttcgccaag ctcctctgat catacctctg aaagcaacct ctaccccgt    2880 gtccataaaa caataccca tgtcacaaga agccagactg gggatcaagc cccacataca    2940
gagactgttg gaccagggaa tactggtacc ctgccagtcc ccctggaaca cgcccctgct   3000
acccgttaag aaaccaggga ctaatgatta taggcctgtc caggatctga gagaagtcaa   3060
caagcgggtg gaagacatcc accccaccgt gcccaacct tacaacctct gagcgggct    3120 cccaccgtcc caccagtggt acactgtgct tgatttaaag gatgcctttt tctgcctgag   3180
actccacccc accagtcagc ctctcttcgc ctttgagtgg agagatccag agatgggaat   3240
ctcaggacaa ttgacctgga ccagactccc acagggtttc aaaaacagtc ccaccctgtt   3300
tgatgaggca ctgcacagag acctagcaga cttccggatc cagcacccag acttgatcct   3360
gctacagtac gtggatgact tactgctggc cgccacttct gagctagact gccaacaagg   3420
tactcgggcc ctgttacaaa ccctagggaa cctcgggtat cgggcctcgg ccaagaaagc   3480
ccaaatttgc cagaaacagg tcaagtatct ggggtatctt ctaaaagagg gtcagagatg   3540
gctgactgag gccagaaaag agactgtgat ggggcagcct actccgaaga cccctcgaca   3600
actaagggag ttcctaggga cggcaggctt ctgtcgcctc tggatccctg gtttgcaga    3660 aatggcagcc cccttgtacc ctctcaccaa aacgggact ctgtttaatt ggggcccaga    3720
ccaacaaaag gcctatcaag aaatcaagca agctcttcta actgccccag ccctgggtt    3780 gccagatttg actaagccct ttgaactctt tgtcgacgag aagcagggct acgccaaagg   3840
tgtcctaacg caaaaactgg gaccttggcg tcggccggtg gcctacctgt ccaaaaagct   3900
agacccagta gcagctgggt ggcccccttg cctacggatg gtagcagcca ttgccgtact   3960
gacaaaggat gcaggcaagc taaccatggg acagccacta gtcattctgg cccccatgc    4020 agtagaggca ctagtcaaac aaccccccga ccgctggctt tccaacgccc ggatgactca   4080
ctatcaggcc ttgcttttgg acacggaccg ggtccagttc ggaccggtgg tagccctgaa   4140
cccggctacg ctgctcccac tgcctgagga agggctgcaa cacaactgcc ttgatatcct   4200
```

-continued

```
ggccgaagcc cacggaaccc gacccgacct aacggaccag ccgctcccag acgccgacca      4260
cacctggtac acggatggaa gcagtctctt acaagaggga cagcgtaagg cgggagctgc      4320
ggtgaccacc gagaccgagg taatctgggc taaagccctg ccagccggga catccgctca      4380
gcgggctgaa ctgatagcac tcacccaggc cctaaagatg gcagaaggta agaagctaaa      4440
tgtttatact gatagccgtt atgcttttgc tactgcccat atccatggag aaatatacag      4500
aaggcgtggg ttgctcacat cagaaggcaa agagatcaaa aataaagacg agatcttggc      4560
cctactaaaa gccctctttc tgcccaaaag acttagcata atccattgtc caggacatca      4620
aaagggacac agcgccgagg ctagaggcaa ccggatggct gaccaagcgg cccgaaaggc      4680
agccatcaca gagactccag acacctctac cctcctcata gaaaattcat caccctacac      4740
ctcagaacat tttcattaca cagtgactga tataaaggac ctaaccaagt tgggggccat      4800
ttatgataaa acaaagaagt attgggtcta ccaaggaaaa cctgtgatgc ctgaccagtt      4860
tacttttgaa ttattagact ttcttcatca gctgactcac ctcagcttct caaaaatgaa      4920
ggctctccta gagagaagcc acagtcccta ctacatgctg aaccgggatc gaacactcaa      4980
aaatatcact gagacctgca aagcttgtgc acaagtcaac gccagcaagt ctgccgttaa      5040
acagggaact agggtccgcg ggcatcggcc cggcactcat tgggagatcg atttcaccga      5100
gataaagccc ggattgtatg gctataaata tcttctagtt tttatagata ccttttctgg      5160
ctggatagaa gccttcccaa ccaagaaaga aaccgccaag gtcgtaacca agaagctact      5220
agaggagatc ttccccaggt tcggcatgcc tcaggtattg ggaactgaca atgggcctgc      5280
cttcgtctcc aaggtgagtc agacagtggc cgatctgttg gggattgatt ggaaattaca      5340
ttgtgcatac agacccaaa gctcaggcca ggtagaaaga atgaatagaa ccatcaagga      5400
gactttaact aaattaacgc ttgcaactgg ctctagagac tgggtgctcc tactcccctt      5460
agccctgtac cgagcccgca acacgccggg ccccatggcc ctcaccccat atgagatctt      5520 atatgggggca cccccgcccc ttgtaaactt ccctgaccct gacatgacaa gagttactaa      5580
cagcccctct ctccaagctc acttacaggc tctctactta gtccagcacg aagtctggag      5640
acctctggcg gcagcctacc aagaacaact ggaccgaccg gtggtacctc acccttaccg      5700
agtcggcgac acagtgtggg tccgccgaca ccagactaag aacctagaac ctcgctggaa      5760
aggaccttac acagtcctgc tgaccacccc caccgccctc aaagtagacg gcatcgcagc      5820
ttggatacac gccgccacg tgaaggctgc cgaccccggg ggtggaccat cctctagact      5880
gacatggcgc gttcaacgct ctcaaaaccc cttaaaaata aggttaaccc gcgaggcccc      5940
ctaatcccct taattcttct gatgctcaga ggggtcagta ctgcttcgcc cggctccagt      6000
gcggcccagc cggccaccat gaaaacattt aacatttctc aacaagatct agaattagta      6060
gaagtagcga cagagaagat tacaatgctt tatgaggata ataaacatca tgtgggagcg      6120
gcaattcgta cgaaaacagg agaaatcatt tcggcagtac atattgaagc gtatatagga      6180
cgagtaactg tttgtgcaga agccattgcg attggtagtc cagtttcgaa tggacaaaag      6240
gattttgaca cgattgtagc tgttagacac ccttattctg acgaagtaga tagaagtatt      6300
cgagtggtaa gtccttgtgg tatgtgtagg gagttgattt cagactatgc accagattgt      6360
tttgtgttaa tagaaatgaa tggcaagtta gtcaaaacta cgattgaaga actcattcca      6420
ctcaaatata cccgaaatta aagttttac caccaagctt atcgattagt ccaatttgtt      6480
aaagacagga tatcagtggt ccaggctcta gttttgactc aacaatatca ccagctgaag      6540
cctatagagt acgagccata gataaaataa aagatttat ttagtctcca gaaaagggg       6600
```

```
ggaatgaaag accccacctg taggtttggc aagctagctt aagtaacgcc attttgcaag    6660
gcatggaaaa atacataact gagaatagag aagttcagat caaggtcagg aacagatgga    6720
acagtcgaga acttgtttat tgcagcttat aatggttaca aataaagcaa tagcatcaca    6780
aatttcacaa ataaagcatt tttttcactg cattctagtt gtggtttgtc caaactcatc    6840
aatgtatctt atcatgtctg gatccccagg aagctcctct gtgtcctcat aaaccctaac    6900
ctcctctact tgagaggaca ttccaatcat aggctgccca tccaccctct gtgtcctcct    6960
gttaattagg tcacttaaca aaaggaaat tgggtagggg ttttttcacag accgctttct    7020 aagggtaatt ttaaaatatc tgggaagtcc cttccactgc tgtgttccag aagtgttggt    7080
aaacagccca caaatgtcaa cagcagaaac atacaagctg tcagctttgc acaagggccc    7140
aacaccctgc tcatcaagaa gcactgtggt tgctgtgtta gtaatgtgca aaacaggagg    7200
cacattttcc ccacctgtgt aggttccaaa atatctagtg ttttcatttt tacttggatc    7260
aggaacccag cactccactg gataagcatt atccttatcc aaaacagcct tgtggtcagt    7320
gttcatctgc tgactgtcaa ctgtagcatt ttttggggtt acagtttgag caggatattt    7380
ggtcctgtag tttgctaaca caccctgcag ctccaaaggt tccccaccaa cagcaaaaaa    7440
atgaaaattt gacccttgaa tgggttttcc agcaccattt tcatgagttt tttgtgtccc    7500
tgaatgcaag tttaacatag cagttacccc aataacctca gttttaacag taacagcttc    7560
ccacatcaaa atatttccac aggttaagtc ctcatttaaa ttaggcaaag gaattc        7616

<210> SEQ ID NO 3
<211> LENGTH: 7308
<212> TYPE: DNA
<213> ORGANISM: Artificial Sequence
<220> FEATURE:
<223> OTHER INFORMATION: Description of Artificial Sequence: Portion of
      construct

<400> SEQUENCE: 3
agatctcccg atcccctatg gtcgactctc agtacaatct gctctgatgc cgcatagtta      60
agccagtatc tgctccctgc ttgtgtgttg gaggtcgctg agtagtgcgc gagcaaaatt     120
taagctacaa caaggcaagg cttgaccgac aattgcatga agaatctgct tagggttagg     180
cgttttgcgc tgcttcgcga tgtacgggcc agatatacgc gttgacattg attattgact     240
agttattaat agtaatcaat tacggggtca ttagttcata gcccatatat ggagttccgc     300
gttacataac ttacggtaaa tggcccgcct ggctgaccgc ccaacgaccc cgcccattg      360 acgtcaataa tgacgtatgt tcccatagta acgccaatag ggactttcca ttgacgtcaa     420
tgggtggact atttacggta aactgcccac ttggcagtac atcaagtgta tcatatgcca     480
agtacgcccc ctattgacgt caatgacggt aaatggcccg cctggcatta tgcccagtac     540
atgaccttat gggactttcc tacttggcag tacatctacg tattagtcat cgctattacc     600
atggtgatgc ggttttggca gtacatcaat gggcgtggat agcggtttga ctcacgggga     660
tttccaagtc tccaccccat tgacgtcaat gggagtttgt tttggcacca aaatcaacgg     720
gactttccaa aatgtcgtaa caactccgcc ccattgacgc aaatgggcgg taggcgtgta     780
cggtgggagg tctatataag cagagctctc tggctaacta gagaacccac tgcttaactg     840
gcttatcgaa atgtcgactg agaacttcag ggtgagtttg ggaccccttg attgttcttt     900 cttttttcgct attgtaaaat tcatgttata tggagggggc aaagttttca gggtgttgtt     960
tagaatggga agatgtccct tgtatcacca tggaccctca tgataatttt gtttctttca    1020
```

```
ctttctactc tgttgacaac cattgtctcc tcttattttc ttttcatttt ctgtaacttt    1080
ttcgttaaac tttagcttgc atttgtaacg aattttaaaa ttcacttttg tttatttgtc    1140
agattgtaag tactttctct aatcactttt ttttcaaggc aatcagggta tattatattg    1200
tacttcagca cagttttaga gaacaattgt tataattaaa tgataaggta gaatatttct    1260
gcatataaat tctggctggc gtggaaatat tcttattggt agaaacaact acatcctggt    1320
catcatcctg cctttctctt tatggttaca atgatataca ctgtttgaga tgaggataaa    1380
atactctgag tccaaaccgg gccccctctgc taaccatgtt catgccttct tctttttcct    1440
acagctcctg ggcaacgtgc tggttgttgt gctgtctcat catttttggca agaattggcc    1500 gcaagcttct gcagcatcgt tctgtgttgt ctctgtctga ctgtgtttct gtatttgtct    1560
gagaatatgg gccagactgt taccactccc ttaagtttga ccttaggtca ctggaaagat    1620
gtcgagcgga tcgctcacaa ccagtcggta gatgtcaaga agagacgttg ggttaccttc    1680
tgctctgcag aatggccaac ctttaacgtc ggatggccgc gagacggcac ctttaaccga    1740
gacctcatca cccaggttaa gatcaaggtc ttttcacctg gcccgcatgg acacccagac    1800
caggtcccct acatcgtgac ctgggaagcc ttggcttttg accccctcc ctgggtcaag    1860 ccttttgtac accctaagcc tccgcctcct cttcctccat ccgcccgtc tctccccctt    1920 gaacctcctc gttcgacccc gcctcgatcc tcccttatc cagccctcac tccttctcta    1980
ggcgccaaac ctaaacctca agttctttct gacagtgggg ggccgctcat cgacctactt    2040
acagaagacc ccccgcctta tagggaccca agaccacccc cttccgacag ggacggaaat    2100
ggtggagaag cgaccctgc gggagaggca ccggacccct ccccaatggc atctcgccta    2160
cgtgggagac gggagccccc tgtggccgac tccactacct cgcaggcatt ccccctccgc    2220
gcaggaggaa acgacagct tcaatactgg ccgttctcct cttctgacct ttacaactgg    2280
aaaaataata acccttcttt ttctgaagat ccaggtaaac tgacagctct gatcgagtct    2340
gttctcatca cccatcagcc cacctgggac gactgtcagc agctgttggg gactctgctg    2400
accggagaag aaaaacaacg ggtgctctta gaggctagaa aggcggtgcg gggcgatgat    2460
gggcgcccca ctcaactgcc caatgaagtc gatgccgctt ttccctcga gcgcccagac    2520 tgggattaca ccacccaggc aggtaggaac cacctagtcc actatcgcca gttgctccta    2580
gcgggtctcc aaaacgcggg cagaagcccc accaatttgg ccaaggtaaa aggaataaca    2640
caagggccca atgagtctcc ctcggccttc ctagagagac ttaaggaagc ctatcgcagg    2700
tacactcctt atgaccctga ggacccaggg caagaaacta atgtgtctat gtctttcatt    2760
tggcagtctg ccccagacat tgggagaaag ttagagaggt tagaagattt aaaaaacaag    2820
acgcttggag atttggttag agaggcagaa aagatcttta ataaacgaga aaccccggaa    2880
gaaagagagg aacgtatcag gagagaaaca gaggaaaaag aagaacgccg taggacagag    2940
gatgagcaga aagagaaaga aagagatcgt aggagacata gagagatgag caagctattg    3000
gccactgtcg ttagtggaca gaaacaggat agacaggag gagaacgaag gaggtcccaa    3060
ctcgatcgcg accagtgtgc ctactgcaaa gaaaaggggc actgggctaa agattgtccc    3120
aagaaaccac gaggacctcg gggaccaaga ccccagacct ccctcctgac cctagatgac    3180
tagggaggtc aggtcaggga gccccccct gaacccagga taaccctcaa agtcggggg    3240 caacccgtca ccttcctggt agatactggg gcccaacact ccgtgctgac ccaaaatcct    3300
ggacccctaa gtgataagtc tgcctgggtc caaggggcta ctggaggaaa gcggtatcgc    3360
```

-continued

```
tggaccacgg atcgcaaagt acatctagct accggtaagg tcacccactc tttcctccat    3420
gtaccagact gtccctatcc tctgttagga agagatttgc tgactaaact aaaagcccaa    3480
atccactttg agggatcagg agctcaggtt atgggaccaa tggggcagcc cctgcaagtg    3540
ttgaccctaa atatagaaga tgagcatcgg ctacatgaga cctcaaaaga gccagatgtt    3600
tctctagggt ccacatggct gtctgatttt cctcaggcct gggcggaaac cgggggcatg    3660
ggactggcag ttcgccaagc tcctctgatc ataccctctga aagcaacctc taccccgtg     3720 tccataaaac aataccccat gtcacaagaa gccagactgg ggatcaagcc ccacatacag    3780
agactgttgg accagggaat actggtaccc tgccagtccc cctggaacac gcccctgcta    3840
cccgttaaga aaccagggac taatgattat aggcctgtcc aggatctgag agaagtcaac    3900
aagcgggtgg aagacatcca ccccaccgtg cccaacccctt acaacctctt gagcgggctc    3960
ccaccgtccc accagtggta cactgtgctt gatttaaagg atgccttttt ctgcctgaga    4020
ctccacccca ccagtcagcc tctcttcgcc tttgagtgga gagatccaga gatgggaatc    4080
tcaggacaat tgacctggac cagactccca cagggtttca aaaacagtcc caccctgttt    4140
gatgaggcac tgcacagaga cctagcagac ttccggatcc agcacccaga cttgatcctg    4200
ctacagtacg tggatgactt actgctggcc gccacttctg agctagactg ccaacaaggt    4260
actcgggccc tgttacaaac cctagggaac ctcgggtatc gggcctcggc caagaaagcc    4320
caaatttgcc agaaacaggt caagtatctg gggtatcttc taaaagaggg tcagagatgg    4380
ctgactgagg ccagaaaaga gactgtgatg gggcagccta ctccgaagac ccctcgacaa    4440
ctaagggagt tcctagggac ggcaggcttc tgtcgcctct ggatccctgg gtttgcagaa    4500
atggcagccc ccttgtaccc tctcaccaaa acggggactg tgtttaattg gggcccagac    4560
caacaaaagg cctatcaaga aatcaagcaa gctcttctaa ctgccccagc cctggggttg    4620
ccagatttga ctaagcccctt tgaactcttt gtcgacgaga agcagggcta cgccaaaggt    4680
gtcctaacgc aaaaactggg accttggcgt cggccggtgg cctacctgtc caaaaagcta    4740
gacccagtag cagctgggtg gccccccttgc ctacggatgg tagcagccat tgccgtactg    4800
acaaaggatg caggcaagct aaccatggga cagccactag tcattctggc ccccatgca    4860 gtagaggcac tagtcaaaca acccccgac cgctggcttt ccaacgcccg gatgactcac    4920
tatcaggcct tgcttttgga cacggaccgg gtccagttcg gaccggtggt agccctgaac    4980
ccggctacgc tgctcccact gcctgaggaa gggctgcaac acaactgcct tgatatcctg    5040
gccgaagccc acggaacccg acccgaccta acggaccagc cgctcccaga cgccgaccac    5100
acctggtaca cggatggaag cagtctctta caagagggac agcgtaaggc gggagctgcg    5160
gtgaccaccg agaccgaggt aatctgggct aaagccctgc cagccgggac atccgctcag    5220
cgggctgaac tgatagcact cacccaggcc ctaaagatgg cagaaggtaa gaagctaaat    5280
gtttatactg atagccgtta tgcttttgct actgcccata tccatggaga aatatacaga    5340
aggcgtgggt tgctcacatc agaaggcaaa gagatcaaaa ataaagacga gatcttggcc    5400
ctactaaaag ccctctttct gcccaaaaga cttagcataa tccattgtcc aggacatcaa    5460
aagggacaca cgcgccgaggc tagaggcaac cggatggctg accaagcggc ccgaaaggca    5520
gccatcacag agactccaga cacctctacc ctcctcatag aaaattcatc accctacacc    5580
tcagaacatt ttcattacac agtgactgat ataaaggacc taaccaagtt gggggccatt    5640
tatgataaaa caaagaagta ttgggtctac caaggaaaac ctgtgatgcc tgaccagttt    5700
acttttgaat tattagactt tcttcatcag ctgactcacc tcagcttctc aaaaatgaag    5760
```

```
gctctcctag agagaagcca cagtccctac tacatgctga accgggatcg aacactcaaa    5820
aatatcactg agacctgcaa agcttgtgca caagtcaacg ccagcaagtc tgccgttaaa    5880
cagggaacta gggtccgcgg gcatcggccc ggcactcatt gggagatcga tttcaccgag    5940
ataaagcccg gattgtatgg ctataaatat cttctagttt ttatagatac cttttctggc    6000
tggatagaag ccttcccaac caagaaagaa accgccaagg tcgtaaccaa gaagctacta    6060
gaggagatct tccccaggtt cggcatgcct caggtattgg gaactgacaa tgggcctgcc    6120
ttcgtctcca aggtgagtca gacagtggcc gatctgttgg ggattgattg gaaattacat    6180
tgtgcataca gaccccaaag ctcaggccag gtagaaagaa tgaatagaac catcaaggag    6240
actttaacta aattaacgct tgcaactggc tctagagact gggtgctcct actcccctta    6300
gccctgtacc gagcccgcaa cacgccgggc ccccatggcc tcacccata tgagatctta    6360 tatggggcac ccccgcccct tgtaaacttc cctgaccctg acatgacaag agttactaac    6420
agcccctctc tccaagctca cttacaggct ctctacttag tccagcacga agtctggaga    6480
cctctggcgg cagcctacca agaacaactg gaccgaccgg tggtacctca cccttaccga    6540
gtcggcgaca cagtgtgggt ccgccgacac cagactaaga acctagaacc tcgctggaaa    6600
ggaccttaca cagtcctgct gaccacccc accgccctca agtagacgg catcgcagct    6660 tggatacacg ccgcccacgt gaaggctgcc gaccccgggg gtggaccatc tctagactg    6720 acatggcgcg ttcaacgctc tcaaaacccc ttaaaaataa ggttaacccg cgaggccccc    6780 taatccccctt aattcttctg atgctcagag gggtcagtac tgcttcgccc ggctccagtg    6840
cggcccagcc ggccaccatg aaaacattta acatttctca acaagatcta gaattagtag    6900
aagtagcgac agagaagatt acaatgcttt atgaggataa taaacatcat gtgggagcgg    6960
caattcgtac gaaaacagga gaaatcattt cggcagtaca tattgaagcg tatataggac    7020
gagtaactgt ttgtgcagaa gccattgcga ttggtagtgc agtttcgaat ggacaaaagg    7080
attttgacac gattgtagct gttagacacc cttattctga cgaagtagat agaagtattc    7140
gagtggtaag tccttgtggt atgtgtaggg agttgatttc agactatgca ccagattgtt    7200
ttgtgttaat agaaatgaat ggcaagttag tcaaaactac gattgaagaa ctcattccac    7260
tcaaatatac ccgaaattaa aagttttacc accaagctta tcgaattc                 7308
```

<210> SEQ ID NO 4
<211> LENGTH: 7308
<212> TYPE: DNA
<213> ORGANISM: Artificial Sequence
<220> FEATURE:
<223> OTHER INFORMATION: Description of Artificial Sequence: Portion of
      construct

<400> SEQUENCE: 4

```
agatctcccg atcccctatg gtcgactctc agtacaatct gctctgatgc cgcatagtta      60
agccagtatc tgctccctgc ttgtgtgttg gaggtcgctg agtagtgcgc gagcaaaatt     120
taagctacaa caaggcaagg cttgaccgac aattgcatga agaatctgct tagggttagg     180
cgttttgcgc tgcttgcgcga tgtacgggcc agatatacgg gttgacattg attattgact     240
agttattaat agtaatcaat tacggggtca ttagttcata gcccatatat ggagttccgc     300
gttacataac ttacggtaaa tggcccgcct ggctgaccgc ccaacgaccc ccgcccattg     360
acgtcaataa tgacgtatgt tcccatagta acgccaatag ggactttcca ttgacgtcaa     420
tgggtggact atttacggta aactgcccac ttggcagtac atcaagtgta tcatatgcca     480
```

```
agtacgcccc ctattgacgt caatgacggt aaatggcccg cctggcatta tgcccagtac    540
atgaccttat gggactttcc tacttggcag tacatctacg tattagtcat cgctattacc    600
atggtgatgc ggttttggca gtacatcaat gggcgtggat agcggtttga ctcacgggga    660
tttccaagtc tccaccccat tgacgtcaat gggagtttgt tttggcacca aaatcaacgg    720
gactttccaa aatgtcgtaa caactccgcc ccattgacgc aaatgggcgg taggcgtgta    780
cggtgggagg tctatataag cagagctctc tggctaacta gagaacccac tgcttaactg    840
gcttatcgaa atgtcgactg agaacttcag ggtgagtttg ggaccccttg attgttcttt    900
ctttttcgct attgtaaaat tcatgttata tggagggggc aaagttttca gggtgttgtt    960
tagaatggga agatgtccct tgtatcacca tggaccctca tgataatttt gtttctttca   1020
ctttctactc tgttgacaac cattgtctcc tcttattttc ttttcatttt ctgtaacttt   1080
ttcgttaaac tttagcttgc atttgtaacg aattttttaaa ttcacttttg tttatttgtc   1140
agattgtaag tacttttctct aatcactttt ttttcaaggc aatcagggta tattatattg   1200
tacttcagca cagtttttaga gaacaattgt tataattaaa tgataaggta gaatatttct   1260
gcatataaat tctggctggc gtggaaatat tcttattggt agaaacaact acatcctggt   1320
catcatcctg cctttctctt tatggttaca atgatataca ctgtttgaga tgaggataaa   1380
atactctgag tccaaaccgg gcccctctgc taaccatgtt catgccttct tcttttttcct   1440 acagctcctg ggcaacgtgc tggttgttgt gctgtctcat cattttggca agaattggcc   1500
gcaagcttct gcagcatcgt tctgtgttgt ctctgtctga ctgtgtttct gtatttgtct   1560
gagaatatgg gccagactgt taccactccc ttaagtttga ccttaggtca ctggaaagat   1620
gtcgagcgga tcgctcacaa ccagtcggta gatgtcaaga agagacgttg ggttaccttc   1680
tgctctgcag aatggccaac ctttaacgtc ggatggccgc gagacggcac ctttaaccga   1740
gacctcatca cccaggttaa gatcaaggtc ttttcacctg gcccgcatgg acacccagac   1800
caggtcccct acatcgtgac ctgggaagcc ttggcttttg accccctcc ctgggtcaag   1860 ccctttgtac accctaagcc tccgcctcct cttcctccat ccgcccgtc tctccccctt   1920 gaacctcctc gttcgacccc gcctcgatcc tccctttatc cagccctcac tccttctcta   1980
ggcgccaaac ctaaacctca agttctttct gacagtgggg ggccgctcat cgacctactt   2040
acagaagacc ccccgcctta tagggaccca agaccacccc cttccgacag ggacggaaat   2100
ggtggagaag cgacccctgc gggagaggca ccggaccccct ccccaatggc atctcgccta   2160
cgtgggagac gggagccccc tgtggccgac tccactacct cgcaggcatt ccccctccgc   2220
gcaggaggaa acgacagct tcaatactgg ccgttctcct cttctgacct ttacaactgg   2280
aaaaataata acccttcttt ttctgaagat ccaggtaaac tgacagctct gatcgagtct   2340
gttctcatca cccatcagcc cacctgggac gactgtcagc agctgttggg gactctgctg   2400
accggagaag aaaaacaacg ggtgctctta gaggctagaa aggcggtgcg gggcgatgat   2460
gggcgcccca ctcaactgcc caatgaagtc gatgccgctt tccccctcga gcgcccagac   2520
tgggattaca ccacccaggc aggacgcaac cacctagtcc actatcgcca gttgctccta   2580
gcgggtctcc aaaacgcggg cagaagcccc accaatttgg ccaaggtaaa aggaataaca   2640
caagggccca atgagtctcc ctcggccttc ctagagagac ttaaggaagc ctatcgcagg   2700
tacactcctt atgaccctga ggacccaggg caagaaacta atgtgtctat gtctttcatt   2760
tggcagtctg ccccagacat tgggagaaag ttagagaggt tagaagattt aaaaaacaag   2820
```

-continued

```
acgcttggag atttggttag agaggcagaa aagatctttta ataaacgaga aaccccggaa    2880
gaaagagagg aacgtatcag gagagaaaca gaggaaaaag aagaacgccg taggacagag    2940
gatgagcaga aagagaaaga aagagatcgt aggagacata gagagatgag caagctattg    3000
gccactgtcg ttagtggaca gaaacaggat agacagggag gagaacgaag gaggtcccaa    3060
ctcgatcgcg accagtgtgc ctactgcaaa gaaaaggggc actgggctaa agattgtccc    3120
aagaaaccac gaggacctcg gggaccaaga ccccagacct ccctcctgac cctagatgac    3180
tagggaggtc agggtcagga gccccccccct gaacccagga taaccctcaa agtcgggggg    3240
caacccgtca ccttcctggt agatactggg gcccaacact ccgtgctgac ccaaaatcct    3300 ggaccccctaa gtgataagtc tgcctgggtc caaggggcta ctggaggaaa gcggtatcgc    3360
tggaccacgg atcgcaaagt acatctagct accggtaagg tcacccactc tttcctccat    3420
gtaccagact gtccctatcc tctgttagga agagatttgc tgactaaact aaaagcccaa    3480
atccactttg agggatcagg agctcaggtt atgggaccaa tggggcagcc cctgcaagtg    3540
ttgaccctaa atatagaaga tgagcatcgg ctacatgaga cctcaaaaga gccagatgtt    3600
tctctagggt ccacatggct gtctgatttt cctcaggcct gggcggaaac cggggcatg    3660 ggactggcag ttcgccaagc tcctctgatc atacctctga aagcaacctc tacccccgtg    3720
tccataaaac aatacccccat gtcacaagaa gccagactgg ggatcaagcc ccacatacag    3780
agactgttgg accagggaat actggtaccc tgccagtccc cctggaacac gcccctgcta    3840
cccgttaaga aaccagggac taatgattat aggcctgtcc aggatctgag agaagtcaac    3900
aagcgggtgg aagacatcca ccccaccgtg cccaaccctt acaacctctt gagcgggctc    3960
ccaccgtccc accagtggta cactgtgctt gatttaaagg atgccttttt ctgcctgaga    4020
ctccacccca ccagtcagcc tctcttcgcc tttgagtgga gagatccaga gatgggaatc    4080
tcaggacaat tgacctggac cagactccca cagggtttca aaaacagtcc caccctgttt    4140
gatgaggcac tgcacagaga cctagcagac ttccggatcc agcacccaga cttgatcctg    4200
ctacagtacg tggatgactt actgctggcc gccacttctg agctagactg ccaacaaggt    4260
actcgggccc tgttacaaac cctagggaac ctcgggtatc gggcctcggc caagaaagcc    4320
caaatttgcc agaaacaggt caagtatctg gggtatcttc taaaagaggg tcagagatgg    4380
ctgactgagg ccagaaaaga gactgtgatg gggcagccta ctccgaagac ccctcgacaa    4440
ctaagggagt tcctagggac ggcaggcttc tgtcgcctct ggatccctgg gtttgcagaa    4500
atggcagccc ccttgtaccc tctcaccaaa acggggactc tgtttaattg ggcccagac    4560 caacaaaagg cctatcaaga aatcaagcaa gctcttctaa ctgccccagc cctggggttg    4620
ccagatttga ctaagcccct tgaactcttt gtcgacgaga agcagggcta cgccaaaggt    4680
gtcctaacgc aaaaactggg accttggcgt cggccggtgg cctacctgtc caaaaagcta    4740
gacccagtag cagctgggtg gccccttgc ctacggatgg tagcagccat tgccgtactg    4800
acaaaggatg caggcaagct aaccatggga cagccactag tcattctggc cccccatgca    4860
gtagaggcac tagtcaaaca acccccgac cgctggcttt ccaacgcccg gatgactcac    4920
tatcaggcct tgcttttgga cacggaccgg gtccagttcg gaccggtggt agccctgaac    4980
ccggctacgc tgctcccact gcctgaggaa gggctgcaac acaactgcct tgatatcctg    5040
gccgaagccc acgaacccg accgaccta acggaccagc cgctcccaga cgccgaccac    5100
acctggtaca cggatggaag cagtctctta caagagggac agcgtaaggc gggagctgcg    5160
gtgaccaccg agaccgaggt aatctgggct aaagccctgc cagccgggac atccgctcag    5220
```

```
cgggctgaac tgatagcact cacccaggcc ctaaagatgg cagaaggtaa gaagctaaat   5280
gtttatactg atagccgtta tgcttttgct actgcccata tccatggaga aatatacaga   5340
aggcgtgggt tgctcacatc agaaggcaaa gagatcaaaa ataaagacga gatcttggcc   5400
ctactaaaag ccctctttct gcccaaaaga cttagcataa tccattgtcc aggacatcaa   5460
aagggacaca gcgccgaggc tagaggcaac cggatggctg accaagcggc ccgaaaggca   5520
gccatcacag agactccaga cacctctacc ctcctcatag aaaattcatc accctacacc   5580
tcagaacatt ttcattacac agtgactgat ataaaggacc taaccaagtt gggggccatt   5640
tatgataaaa caagaagta ttgggtctac caaggaaaac ctgtgatgcc tgaccagttt   5700
acttttgaat tattagactt tcttcatcag ctgactcacc tcagcttctc aaaaatgaag   5760
gctctcctag agaagccaa cagtccctac tacatgctga accgggatcg aacactcaaa   5820
aatatcactg agacctgcaa agcttgtgca caagtcaacg ccagcaagtc tgccgttaaa   5880
cagggaacta gggtccgcgg gcatcggccc ggcactcatt gggagatcga tttcaccgag   5940
ataaagcccg gattgtatgg ctataaatat cttctagttt ttatagatac cttttctggc   6000
tggatagaag ccttcccaac caagaaagaa accgccaagg tcgtaaccaa gaagctacta   6060
gaggagatct tccccaggtt cggcatgcct caggtattgg gaactgacaa tgggcctgcc   6120
ttcgtctcca aggtgagtca gacagtggcc gatctgttgg ggattgattg gaaattacat   6180
tgtgcataca gaccccaaag ctcaggccag gtagaaagaa tgaatagaac catcaaggag   6240
actttaacta aattaacgct tgcaactggc tctagagact gggtgctcct actccccta   6300 gccctgtacc gagcccgcaa cacgccgggc ccccatggcc tcaccccata tgagatctta   6360 tatgggcac ccccgcccct tgtaaacttc cctgaccctg acatgacaag agttactaac   6420 agccctctc tccaagctca cttacaggct ctctacttag tccagcacga agtctggaga   6480
cctctggcgg cagcctacca agaacaactg gaccgaccgg tggtacctca cccttaccga   6540
gtcggcgaca cagtgtgggt ccgccgacac cagactaaga acctagaacc tcgctggaaa   6600
ggaccttaca cagtcctgct gaccaccccc accgccctca agtagacgg catcgcagct   6660 tggatacacg ccgcccacgt gaaggctgcc gaccccgggg gtggaccatc ctctagactg   6720
acatggcgcg ttcaacgctc tcaaaacccc ttaaaaataa ggttaacccg cgaggccccc   6780
taatcccctt aattcttctg atgctcagag gggtcagtac tgcttcgccc ggctccagtg   6840
cggcccagcc ggccaccatg aaaacattta acatttctca acaagatcta gaattagtag   6900
aagtagcgac agagaagatt acaatgcttt atgaggataa taaacatcat gtgggagcgg   6960
caattcgtac gaaaacagga gaaatcattt cggcagtaca tattgaagcg tatataggac   7020
gagtaactgt ttgtgcagaa gccattgcga ttggtagtgc agtttcgaat ggacaaaagg   7080
attttgacac gattgtagct gttagacacc cttattctga cgaagtagat agaagtattc   7140
gagtggtaag tccttgtggt atgtgtaggg agttgatttc agactatgca ccagattgtt   7200
ttgtgttaat agaaatgaat ggcaagttag tcaaaactac gattgaagaa ctcattccac   7260
tcaaatatac ccgaaattaa aagttttacc accaagctta tcgaattc          7308

<210> SEQ ID NO 5
<211> LENGTH: 6028
<212> TYPE: DNA
<213> ORGANISM: Artificial Sequence
<220> FEATURE:
<223> OTHER INFORMATION: Description of Artificial Sequence: Portion of
      construct
```

```
<220> FEATURE:
<221> NAME/KEY: misc_feature
<222> LOCATION: (3774)
<223> OTHER INFORMATION: n is any nucleotide
<220> FEATURE:
<221> NAME/KEY: misc_feature
<222> LOCATION: (3775)
<223> OTHER INFORMATION: n is any nucleotide
<220> FEATURE:
<221> NAME/KEY: misc_feature
<222> LOCATION: (3776)
<223> OTHER INFORMATION: n is any nucleotide
<220> FEATURE:
<221> NAME/KEY: misc_feature
<222> LOCATION: (3777)
<223> OTHER INFORMATION: n is any nucleotide
<220> FEATURE:
<221> NAME/KEY: misc_feature
<222> LOCATION: (3962)
<223> OTHER INFORMATION: n is any nucleotide
<220> FEATURE:
<221> NAME/KEY: misc_feature
<222> LOCATION: (3963)
<223> OTHER INFORMATION: n is any nucleotide
<220> FEATURE:
<221> NAME/KEY: misc_feature
<222> LOCATION: (3964)
<223> OTHER INFORMATION: n is any nucleotide
<220> FEATURE:
<221> NAME/KEY: misc_feature
<222> LOCATION: (3965)
<223> OTHER INFORMATION: n is any nucleotide

<400> SEQUENCE: 5
catatgcggt gtgaaatacc gcacagatgc gtaaggagaa ataccgcat caggcgccat      60 tcgccattca ggctgcgcaa ctgttgggaa gggcgatcgg tgcgggcctc ttcgctatta    120
cgccagctgg cgaaaggggg atgtgctgca aggcgattaa gttgggtaac gccagggttt    180
tcccagtcac gacgttgtaa aacgacggcc agtgaattcc gattagttca atttgttaaa    240
gacaggatct cagtagtcca ggctttagtc ctgactcaac aataccacca gctaaaacca    300
ctagaatacg agccacaata aataaaagat tttatttagt ttccagaaaa aggggggaat    360
gaaagacccc accaaattgc ttagcctgat agccgcagta acgccatttt gcaaggcatg    420
gaaaaatacc aaaccaagaa tagagaagtt cagatcaagg gcgggtacac gaaaacagct    480
aacgttgggc caaacaggat atctgcggtg agcagtttcg gccccggccc ggggccaaga    540
acagatggtc accgcggttc ggccccggcc cggggccaag aacagatggt ccccagatat    600
ggcccaaccc tcagcagttt cttaagaccc atcagatgtt tccaggctcc cccaaggacc    660
tgaaatgacc ctgtgcctta tttgaattaa ccaatcagcc tgcttctcgc ttctgttcgc    720
gcgcttctgc ttcccgagct ctataaaaga gctcacaacc cctcactcgg cgcgccagtc    780
ctccgataga ctgagtcgcc cgggtacccg tgtatccaat aaatcctctt gctgttgcat    840
ccgactcgtg gtctcgctgt tccttgggag ggtctcctca gagtgattga ctaccgtct    900 cgggggtctt tcatttgggg gctcgtccgg gatctggaga ccctgccca gggaccaccg    960 acccaccacc gggaggtaag ctggccaaga tcttatatgg ggcacccccg ccccttgtaa   1020
acttccctga ccctgacatg accagagtta ctaacagccc ctctctccaa gctcacttac   1080
aggctctcta cttagtccag cacgaagttt ggagaccact ggcggcagct taccaagaac   1140
aactggaccg gccggtggtg cctcacccctt accgggtcgg cgacacagtg tgggtccgcc   1200
gacatcaaac caagaaccta gaacctcgct ggaaaggacc ttacacagtc ctgctgacca   1260
cccccaccgc cctcaaagta gacggtatcg cagcttggat acacgcagcc cacgtaaagg   1320
```

-continued

```
cggccgacac cgagagtgga ccatcctctg gacggacatg gcgcgttcaa cgctctcaaa      1380
accccctcaa gataagatta acccgtggaa gcccttaata gtcatgggag tcctgttagg      1440
agtagggatg gcagagagcc cccatcaggt ctttaatgta acctggagag tcaccaacct      1500
gatgactggg cgtaccgcca atgccacctc cctcctggga actgtacaag atgccttccc      1560
aaaattatat tttgatctat gtgatctggt cggagaggag tgggacccctt cagaccagga     1620 accgtatgtc gggtatggct gcaagtaccc cgcagggaga cagcggaccc ggacttttga      1680
cttttacgtg tgccctgggc ataccgtaaa gtcgggtgt gggggaccag gagagggcta      1740
ctgtggtaaa tgggggtgtg aaaccaccgg acaggcttac tggaagccca catcatcgtg     1800
ggacctaatc tcccttaagc gcggtaacac ccctgggac acgggatgct ctaaagttgc      1860
ctgtggcccc tgctacgacc tctccaaagt atccaattcc ttccaagggg ctactcgagg     1920
gggcagatgc aaccctctag tcctagaatt cactgatgca ggaaaaaagg ctaactggga    1980
cgggcccaaa tcgtggggac tgagactgta ccggacagga acagatccta ttaccatgtt   2040
ctccctgacc cggcaggtcc ttaatgtggg accccgagtc cccataggc ccaacccagt    2100 attacccgac caaagactcc cttcctcacc aatagagatt gtaccggctc cacagccacc   2160
tagccccctc aataccagtt accccccttc cactaccagt acaccctcaa cctcccctac   2220
aagtccaagt gtcccacagc caccccagg aactggagat agactactag ctctagtcaa    2280
aggagcctat caggcgctta acctcaccaa tcccgacaag acccaagaat gttggctgtg    2340
cttagtgtcg ggacctcctt attacgaagg agtagcggtc gtgggcactt ataccaatca    2400
ttccaccgct ccggccaact gtacggccac ttcccaacat aagcttaccc tatctgaagt    2460
gacaggacag ggcctatgca tgggggcagt acctaaaact caccaggcct tatgtaacac    2520
cacccaaagc gccggctcag gatcctacta ccttgcagca cccgccggaa caatgtgggc    2580
ttgcagcact ggattgactc cctgcttgtc caccacggtg ctcaatctaa ccacagatta    2640
ttgtgtatta gttgaactct ggcccagagt aatttaccac tcccccgatt atatgtatgg    2700
tcagcttgaa cagcgtacca aatataaaag agagccagta tcattgaccc tggcccttct    2760
actaggagga ttaaccatgg gagggattgc agctggaata gggacgggga ccactgcctt    2820
aattaaaacc cagcagtttg agcagcttca tgccgctatc cagacagacc tcaacgaagt    2880
cgaaaagtca attaccaacc tagaaaagtc actgacctcg ttgtctgaag tagtcctaca    2940
gaaccgcaga ggcctagatt tgctattcct aaaggaggga ggtctctgcg cagccctaaa    3000
agaagaatgt tgtttttatg cagaccacac ggggctagtg agagacagca tggccaaatt    3060
aagagaaagg cttaatcaga gacaaaaact atttgagaca ggccaaggat ggttcgaagg    3120
gctgtttaat agatccccct ggtttaccac cttaatctcc accatcatgg gacctctaat    3180
agtactctta ctgatcttac tctttggacc ttgcattctc aatcgattag ttcaatttgt    3240
taaagacagg atctcagtag tccaggcttt agtcctgact caacaatacc accagctaaa    3300
gcctatagag tacgagccat agggcgccta gtgttgacaa ttaatcatcg gcatagtata    3360
cggcatagta taatacgact cactatagga gggccaccat ggccaagttg accagtgccg    3420
ttccggtgct caccgcgcgc gacgtcgccg gagcggtcga gttctggacc gaccggctcg    3480
ggttctcccg ggacttcgtg gaggacgact cgcggtgt ggtccgggac gacgtgaccc      3540
tgttcatcag cgcggtccag gaccaggtgg tgccggacaa cacctggcc tgggtgtggg     3600 tgcgcggcct ggacgagctg tacgccgagt ggtcggaggt cgtgtccacg aacttccggg    3660
acgcctccgg gccggccatg accgagatcg gcgagcagcc gtggggcgg gagttcgccc     3720
```

```
tgcgcgaccc ggccggcaac tgcgtgcact tcgtggccga ggagcaggac tgannnncgg    3780
accggtcgac ttgttaactt gtttattgca gcttataatg gttacaaata aagcaatagc    3840
atcacaaatt tcacaaataa agcattttt tcactgcatt ctagttgtgg tttgtccaaa     3900
ctcatcaatg tatcttatca tgtctggatc cagatctggg cccatgcggc cgcggatcga    3960
tnnnnacatg tgagcaaaag gccagcaaaa ggccaggaac cgtaaaaagg ccgcgttgct    4020
ggcgtttttc cataggctcc gcccccctga cgagcatcac aaaaatcgac gctcaagtca    4080
gaggtggcga aacccgacag gactataaag ataccaggcg tttcccctg gaagctccct     4140 cgtgcgctct cctgttccga ccctgccgct taccggatac ctgtccgcct ttctcccttc    4200
gggaagcgtg gcgctttctc aatgctcacg ctgtaggtat ctcagttcgg tgtaggtcgt    4260
tcgctccaag ctgggctgtg tgcacgaacc ccccgttcag cccgaccgct gcgccttatc    4320
cggtaactat cgtcttgagt ccaacccggt aagacacgac ttatcgccac tggcagcagc    4380
cactggtaac aggattagca gagcgaggta tgtaggcggt gctacagagt tcttgaagtg    4440
gtggcctaac tacggctaca ctagaaggac agtatttggt atctgcgctc tgctgaagcc    4500
agttaccttc ggaaaaagag ttggtagctc ttgatccggc aaacaaacca ccgctggtag    4560
cggtggtttt tttgtttgca agcagcagat tacgcgcaga aaaaaggat ctcaagaaga     4620 tcctttgatc ttttctacgg ggtctgacgc tcagtggaac gaaaactcac gttaagggat    4680
tttggtcatg agattatcaa aaaggatctt cacctagatc cttttaaatt aaaaatgaag    4740
ttttaaatca atctaaagta tatatgagta aacttggtct gacagttacc aatgcttaat    4800
cagtgaggca cctatctcag cgatctgtct atttcgttca tccatagttg cctgactccc    4860
cgtcgtgtag ataactacga tacgggaggg cttaccatct ggccccagtg ctgcaatgat    4920
accgcgagac ccacgctcac cggctccaga tttatcagca ataaaccagc cagccggaag    4980
ggccgagcgc agaagtggtc ctgcaacttt atccgcctcc atccagtcta ttaattgttg    5040
ccgggaagct agagtaagta gttcgccagt taatagtttg cgcaacgttg ttgccattgc    5100
tacaggcatc gtggtgtcac gctcgtcgtt tggtatggct tcattcagct ccggttccca    5160
acgatcaagg cgagttacat gatcccccat gttgtgcaaa aaagcggtta gctccttcgg    5220
tcctccgatc gttgtcagaa gtaagttggc cgcagtgtta tcactcatgg ttatggcagc    5280
actgcataat tctcttactg tcatgccatc cgtaagatgc ttttctgtga ctggtgagta    5340
ctcaaccaag tcattctgag aatagtgtat gcggcgaccg agttgctctt gcccggcgtc    5400
aatacgggat aataccgcgc cacatagcag aactttaaaa gtgctcatca ttggaaaacg    5460
ttcttcgggg cgaaaactct caaggatctt accgctgttg agatccagtt cgatgtaacc    5520
cactcgtgca cccaactgat cttcagcatc ttttactttc accagcgttt ctgggtgagc    5580
aaaaacagga aggcaaaatg ccgcaaaaaa gggaataagg gcgacacgga aatgttgaat    5640
actcatactc ttccttttc aatattattg aagcatttat cagggttatt gtctcatgag     5700
cggatacata tttgaatgta tttagaaaaa taaacaaata ggggttccgc gcacatttcc    5760
ccgaaaagtg ccacctgacg tctaagaaac cattattatc atgacattaa cctataaaaa    5820
taggcgtatc acgaggccct ttcgtctcgc gcgtttcggt gatgacggtg aaaacctctg    5880
acacatgcag ctcccggaga cggtcacagc ttgtctgtaa gcggatgccg ggagcagaca    5940
agcccgtcag ggcgcgtcag cgggtgttgg cgggtgtcgg ggctggctta actatgcggc    6000
atcagagcag attgtactga gagtgcac                                       6028
```

```
<210> SEQ ID NO 6
<211> LENGTH: 6061
<212> TYPE: DNA
<213> ORGANISM: Artificial Sequence
<220> FEATURE:
<223> OTHER INFORMATION: Description of Artificial Sequence: Portion of
      construct
<220> FEATURE:
<221> NAME/KEY: misc_feature
<222> LOCATION: (3807)
<223> OTHER INFORMATION: n is any nucleotide
<220> FEATURE:
<221> NAME/KEY: misc_feature
<222> LOCATION: (3808)
<223> OTHER INFORMATION: n is any nucleotide
<220> FEATURE:
<221> NAME/KEY: misc_feature
<222> LOCATION: (3809)
<223> OTHER INFORMATION: n is any nucleotide
<220> FEATURE:
<221> NAME/KEY: misc_feature
<222> LOCATION: (3810)
<223> OTHER INFORMATION: n is any nucleotide
<220> FEATURE:
<221> NAME/KEY: misc_feature
<222> LOCATION: (3995)
<223> OTHER INFORMATION: n is any nucleotide
<220> FEATURE:
<221> NAME/KEY: misc_feature
<222> LOCATION: (3996)
<223> OTHER INFORMATION: n is any nucleotide
<220> FEATURE:
<221> NAME/KEY: misc_feature
<222> LOCATION: (3997)
<223> OTHER INFORMATION: n is any nucleotide
<220> FEATURE:
<221> NAME/KEY: misc_feature
<222> LOCATION: (3998)
<223> OTHER INFORMATION: n is any nucleotide

<400> SEQUENCE: 6
catatgcggt gtgaaatacc gcacagatgc gtaaggagaa ataccgcat caggcgccat       60 tcgccattca ggctgcgcaa ctgttgggaa gggcgatcgg tgcgggcctc ttcgctatta    120
cgccagctgg cgaaaggggg atgtgctgca aggcgattaa gttgggtaac gccagggttt    180
tcccagtcac gacgttgtaa aacgacggcc agtgaattcc gattagttca atttgttaaa    240
gacaggatct cagtagtcca ggctttagtc ctgactcaac aataccacca gctaaaacca    300
ctagaatacg agccacaata aataaaagat tttatttagt ttccagaaaa aggggggaat    360
gaaagacccc accaaattgc ttagcctgat agccgcagta acgccatttt gcaaggcatg    420 gaaaatacc aaaccaagaa tagagaagtt cagatcaagg gcgggtacac gaaaacagct    480
aacgttgggc caaacaggat atctgcggtg agcagtttcg gccccggccc ggggccaaga    540
acagatggtc accgcggttc ggccccggcc cggggccaag aacagatggt ccccagatat    600
ggcccaaccc tcagcagttt cttaagaccc atcagatgtt tccaggctcc cccaaggacc    660
tgaaatgacc ctgtgcctta tttgaattaa ccaatcagcc tgcttctcgc ttctgttcgc    720
gcgcttctgc ttcccgagct ctataaaaga gctcacaacc cctcactcgg cgcgccagtc    780
ctccgataga ctgagtcgcc cgggtacccg tgtatccaat aaatcctctt gctgttgcat    840
ccgactcgtg gtctcgctgt tccttgggag ggtctcctca gagtgattga ctaccgtct     900 cggggtctt tcatttgggg gctcgtccgg gatctggaga ccctgcccca gggaccaccg    960
acccaccacc gggaggtaag ctggccaaga tcttatatgg ggcaccccg ccccttgtaa    1020 acttccctga ccctgacatg acaagagtta ctaacagccc ctctctccaa gctcacttac   1080
```

-continued

```
aggctctcta cttagtccag cacgaagtct ggagacctct ggcggcagcc taccaagaac    1140
aactggaccg accggtggta cctcaccctt accgagtcgg cgacacagtg tgggtccgcc    1200
gacaccagac taagaaccta gaacctcgct ggaaaggacc ttacacagtc ctgctgacca    1260
cccccaccgc cctcaaagta gacggcatcg cagcttggat acacgccgcc cacgtgaagg    1320
ctgccgaccc cggggtgga ccatcctcta gactgacatg gcgcgttcaa cgctctcaaa     1380
accccttaaa aataaggtta acccgcgagg cccctaatc cccttaattc ttctgatgct     1440 cagagggtc agtactgctt cgcccggctc cagtcctcat caagtctata atatcacctg     1500
ggaggtaacc aatggagatc gggagacggt atgggcaact tctggcaacc accctctgtg    1560
gacctggtgg cctgaccta ccccagattt atgtatgtta gccaccatg gaccatctta      1620 ttgggggcta gaatatcaat ccccttttc ttctcccccg ggcccccttt gttgctcagg     1680
gggcagcagc ccaggctgtt ccagagactg cgaagaacct taacctccc tcacccctcg     1740 gtgcaacact gcctggaaca gactcaagct agaccagaca actcataaat caaatgaggg    1800
attttatgtt tgccccgggc cccaccgccc ccgagaatcc aagtcatgtg ggggtccaga    1860
ctccttctac tgtgcctatt ggggctgtga gacaaccggt agagcttact ggaagccctc    1920
ctcatcatgg gatttcatca cagtaaacaa caatctcacc tctgaccagg ctgtccaggt    1980
atgcaaagat aataagtggt gcaacccctt agttattcgg tttacagacg ccgggagacg    2040
ggttacttcc tggaccacag gacattactg gggcttacg ttgtatgtct ccggacaaga     2100
tccagggctt acatttggga tccgactcag ataccaaaat ctaggacccc gcgtcccaat    2160
agggccaaac cccgttctgg cagaccaaca gccactctcc aagcccaaac ctgttaagtc    2220
gccttcagtc accaaaccac ccagtgggac tcctctctcc cctacccaac ttccaccggc    2280
gggaacggaa aataggctgc taaacttagt agacggagcc taccaagccc tcaacctcac    2340
cagtcctgac aaaacccaag agtgctggtt gtgtctagta gcgggacccc cctactacga    2400 agggttgcc gtcctgggta cctactccaa ccatacctct gctccagcca actgctccgt     2460
ggcctcccaa cacaagttga ccctgtccga agtgaccgga cagggactct gcataggagc    2520
agttcccaaa acacatcagg ccctatgtaa taccacccag acaagcagtc gagggtccta    2580
ttatctagtt gcccctacag gtaccatgtg ggcttgtagt accgggctta ctccatgcat    2640
ctccaccacc atactgaacc ttaccactga ttattgtgtt cttgtcgaac tctggccaag    2700
agtcacctat cattccccca gctatgttta cggcctgttt gagagatcca accgacacaa    2760
aagagaaccg gtgtcgttaa ccctggccct attattgggt ggactaacca tgggggaat    2820 tgccgctgga ataggaacag gactactgc tctaatggcc actcagcaat tccagcagct     2880
ccaagccgca gtacaggatg atctcaggga ggttgaaaaa tcaatctcta acctagaaaa    2940
gtctctcact tccctgtctg aagttgtcct acagaatcga aggggcctag acttgttatt    3000
tctaaaagaa ggagggctgt gtgctgctct aaaagaagaa tgttgcttct atgcggacca    3060
cacaggacta gtgagagaca gcatggccaa attgagagag aggcttaatc agagacagaa    3120
actgtttgag tcaactcaag gatggtttga gggactgttt aacagatccc cttggtttac    3180
caccttgata tctaccatta tgggacccct cattgtactc ctaatgattt tgctcttcgg    3240
accctgcatt cttaatcgat tagttcaatt tgttaaagac aggatctcag tagtccaggc    3300
tttagtcctg actcaacaat accaccagct aaagcctata gagtacgagc catagggcgc    3360
ctagtgttga caattaatca tcggcatagt atacggcata gtataatacg actcactata    3420
ggagggccac catggccaag ttgaccagtg ccgttccggt gctcaccgcg cgcgacgtcg    3480
```

-continued

```
ccggagcggt cgagttctgg accgaccggc tcggttctc ccgggacttc gtggaggacg    3540
acttcgccgg tgtggtccgg gacgacgtga ccctgttcat cagcgcggtc caggaccagg    3600
tggtgccgga caacaccctg gcctgggtgt gggtgcgcgg cctggacgag ctgtacgccg    3660
agtggtcgga ggtcgtgtcc acgaacttcc gggacgcctc cgggccggcc atgaccgaga    3720
tcggcgagca gccgtgggg cgggagttcg ccctgcgcga cccggccggc aactgcgtgc     3780
acttcgtggc cgaggagcag gactgannnn cggaccggtc gacttgttaa cttgtttatt    3840
gcagcttata atggttacaa ataaagcaat agcatcacaa atttcacaaa taaagcattt    3900
ttttcactgc attctagttg tggtttgtcc aaactcatca atgtatctta tcatgtctgg    3960
atccagatct gggcccatgc ggccgcggat cgatnnnnac atgtgagcaa aaggccagca    4020
aaaggccagg aaccgtaaaa aggccgcgtt gctggcgttt ttccataggc tccgcccccc    4080
tgacgagcat cacaaaaatc gacgctcaag tcagaggtgg cgaaacccga caggactata    4140
aagataccag gcgtttcccc ctggaagctc cctcgtgcgc tctcctgttc cgaccctgcc    4200
gcttaccgga tacctgtccg cctttctccc ttcgggaagc gtggcgcttt ctcaatgctc    4260
acgctgtagg tatctcagtt cggtgtaggt cgttcgctcc aagctgggct gtgtgcacga    4320
accccccgtt cagcccgacc gctgcgcctt atccggtaac tatcgtcttg agtccaaccc    4380
ggtaagacac gacttatcgc cactggcagc agccactggt aacaggatta gcagagcgag    4440
gtatgtaggc ggtgctacag agttcttgaa gtggtggcct aactacggct acactagaag    4500
gacagtattt ggtatctgcg ctctgctgaa gccagttacc ttcggaaaaa gagttggtag    4560
ctcttgatcc ggcaaacaaa ccaccgctgg tagcggtggt ttttttgttt gcaagcagca    4620
gattacgcgc agaaaaaaag gatctcaaga agatcctttg atcttttcta cggggtctga    4680
cgctcagtgg aacgaaaact cacgttaagg gattttggtc atgagattat caaaaaggat    4740
cttcacctag atccttttaa attaaaaatg aagttttaaa tcaatctaaa gtatatatga    4800
gtaaacttgg tctgacagtt accaatgctt aatcagtgag gcacctatct cagcgatctg    4860
tctatttcgt tcatccatag ttgcctgact ccccgtcgtg tagataacta cgatacggga    4920
gggcttacca tctggcccca gtgctgcaat gataccgcga acccacgct caccggctcc     4980 agatttatca gcaataaacc agccagccgg aagggccgag cgcagaagtg gtcctgcaac    5040
tttatccgcc tccatccagt ctattaattg ttgccgggaa gctagagtaa gtagttcgcc    5100
agttaatagt ttgcgcaacg ttgttgccat tgctacaggc atcgtggtgt cacgctcgtc    5160
gtttggtatg gcttcattca gctccggttc ccaacgatca aggcgagtta catgatcccc    5220
catgttgtgc aaaaaagcgg ttagctcctt cggtcctccg atcgttgtca gaagtaagtt    5280
ggccgcagtg ttatcactca tggttatggc agcactgcat aattctctta ctgtcatgcc    5340
atccgtaaga tgcttttctg tgactggtga gtactcaacc aagtcattct gagaatagtg    5400
tatgcggcga ccgagttgct cttgcccggc gtcaatacgg gataataccg cgccacatag    5460
cagaacttta aaagtgctca tcattggaaa acgttcttcg gggcgaaaac tctcaaggat    5520
cttaccgctg ttgagatcca gttcgatgta acccactcgt gcacccaact gatcttcagc    5580
atcttttact ttcaccagcg tttctgggtg agcaaaaaca ggaaggcaaa atgccgcaaa    5640
aaagggaata agggcgacac ggaaatgttg aatactcata ctcttccttt ttcaatatta    5700
ttgaagcatt tatcagggtt attgtctcat gagcggatac atatttgaat gtatttagaa    5760
aaataaacaa ataggggttc cgcgcacatt tccccgaaaa gtgccacctg acgtctaaga    5820
```

-continued

```
aaccattatt atcatgacat taacctataa aaataggcgt atcacgaggc cctttcgtct      5880
cgcgcgtttc ggtgatgacg gtgaaaacct ctgacacatg cagctcccgg agacggtcac      5940
agcttgtctg taagcggatg ccgggagcag acaagcccgt cagggcgcgt cagcgggtgt      6000
tggcgggtgt cggggctggc ttaactatgc ggcatcagag cagattgtac tgagagtgca      6060
c                                                                     6061
```

<210> SEQ ID NO 7
<211> LENGTH: 6312
<212> TYPE: DNA
<213> ORGANISM: Artificial Sequence
<220> FEATURE:
<223> OTHER INFORMATION: Description of Artificial Sequence: Portion of
      construct
<220> FEATURE:
<221> NAME/KEY: misc_feature
<222> LOCATION: (4058)
<223> OTHER INFORMATION: n is any nucleotide
<220> FEATURE:
<221> NAME/KEY: misc_feature
<222> LOCATION: (4059)
<223> OTHER INFORMATION: n is any nucleotide
<220> FEATURE:
<221> NAME/KEY: misc_feature
<222> LOCATION: (4060)
<223> OTHER INFORMATION: n is any nucleotide
<220> FEATURE:
<221> NAME/KEY: misc_feature
<222> LOCATION: (4061)
<223> OTHER INFORMATION: n is any nucleotide
<220> FEATURE:
<221> NAME/KEY: misc_feature
<222> LOCATION: (4246)
<223> OTHER INFORMATION: n is any nucleotide
<220> FEATURE:
<221> NAME/KEY: misc_feature
<222> LOCATION: (4247)
<223> OTHER INFORMATION: n is any nucleotide
<220> FEATURE:
<221> NAME/KEY: misc_feature
<222> LOCATION: (4248)
<223> OTHER INFORMATION: n is any nucleotide
<220> FEATURE:
<221> NAME/KEY: misc_feature
<222> LOCATION: (4249)
<223> OTHER INFORMATION: n is any nucleotide

<400> SEQUENCE: 7

```
catatgcggt gtgaaatacc gcacagatgc gtaaggagaa aataccgcat caggcgccat        60
tcgccattca ggctgcgcaa ctgttgggaa gggcgatcgg tgcgggcctc ttcgctatta       120
cgccagctgg cgaaaggggg atgtgctgca aggcgattaa gttgggtaac gccagggttt       180
tcccagtcac gacgttgtaa aacgacggcc agtgaattcc gattagttca atttgttaaa       240
gacaggatct cagtagtcca ggctttagtc ctgactcaac aataccacca gctaaaacca       300
ctagaatacg agccacaata aataaaagat tttatttagt ttccagaaaa agggggggaat      360 gaaagacccc accaaattgc ttagcctgat agccgcagta acgccatttt gcaaggcatg       420
gaaaaatacc aaaccaagaa tagagaagtt cagatcaagg gcgggtacac gaaaacagct       480
aacgttgggc caaacaggat atctgcggtg agcagtttcg gccccggccc ggggccaaga       540
acagatggtc accgcggttc ggccccggcc cggggccaag aacagatggt ccccagatat       600
ggcccaaccc tcagcagttt cttaagaccc atcagatgtt tccaggctcc cccaaggacc       660
tgaaatgacc ctgtgcctta tttgaattaa ccaatcagcc tgcttctcgc ttctgttcgc       720
gcgcttctgc ttcccgagct ctataaaaga gctcacaacc cctcactcgg cgcgccagtc       780
```

-continued

```
ctccgataga ctgagtcgcc cgggtacccg tgtatccaat aaatcctctt gctgttgcat    840
ccgactcgtg gtctcgctgt tccttgggag ggtctcctca gagtgattga ctacccgtct    900
cggggggtctt tcatttgggg gctcgtccgg gatctggaga cccctgccca gggaccaccg    960
acccaccacc gggaggtaag ctggccaaga tccctaaggt actcgggtca gacaatggcc   1020
cggcctttgt tgctcaggta agtcaggggac tggccactca actggggata aattggaagt   1080
tacattgtgc gtatagaccc cagagctcag gtcaggtaga aagaatgaac agaacaatta   1140
aagagacctt gaccaaatta gccttagaga ccggtgaaaa agactgggtg accctccttc   1200
ccttagcgct gcttagggcc aggaataccc ctggccggtt tggtttaact ccttatgaaa   1260
ttctctatgg aggaccaccc cccatacttg agtctggaga actttgggt cccgatgata    1320
gatttctccc tgtcttattt actcacttaa aggctttaga aattgtaagg acccaaatct   1380
gggaccagat caaagaggtg tataagcctg gtaccgtaac aatccctcac ccgttccagg   1440
tcgggggatca agtgcttgtc agacgccatc gacccagcag ccttgagcct cggtggaaag   1500
gcccatacct ggtgttgctg actacccccga ccgcggtaaa agtcgatggt attgctgcct   1560
gggtccatgc ttctcacctc aaacctgcac caccttcggc accagatgag tcctgggagc   1620
tggaaaagac tgatcatcct cttaagctgc gtattcggcg gcggcgggac gagtctgcaa   1680
aataagaacc cccaccagcc catgaccctc acttggcagg tactgtccca aactggagac   1740
gttgtctggg atacaaaggc agtccagccc ccttggactt ggtggcccac acttaaacct   1800
gatgtatgtg ccttggcggc tagtcttgag tcctgggata tcccgggaac cgatgtctcg   1860
tcctctaaac gagtcagacc tccggactca gactatactg ccgcttataa gcaaatcacc   1920
tggggagcca tagggtgcag ctaccctcgg gctaggacta gaatggcaag ctctaccttc   1980
tacgtatgtc cccgggatgg ccggacccctt tcagaagcta aaggtgcgg ggggctagaa   2040
tccctatact gtaaagaatg ggattgtgag accacgggga ccggttattg gctatctaaa   2100
tcctcaaaag acctcataac tgtaaaatgg gaccaaaata gcgaatggac tcaaaaattt   2160
caacagtgtc accagaccgg ctggtgtaac ccccttaaaa tagatttcac agacaaagga   2220
aaattatcca aggactggat aacgggaaaa acctggggat taagattcta tgtgtctgga   2280
catccaggcg tacagttcac cattcgctta aaaatcacca acatgccagc tgtggcagta   2340
ggtcctgacc tcgtccttgt ggaacaagga cctcctagaa cgtccctcgc tctcccacct   2400
cctcttcccc caagggaagc gccaccgcca tctctccccg actctaactc cacagccctg   2460
gcgactagtg cacaaactcc cacggtgaga aaaacaattg ttaccctaaa cactccgcct   2520
cccaccacag gcgacagact ttttgatctt gtgcaggggg ccttcctaac cttaaatgct   2580
accaacccag gggccactga gtcttgctgg cttttgtttgg ccatgggccc cccttattat   2640
gaagcaatag cctcatcagg agaggtcgcc tactccaccg accttgaccg gtgccgctgg   2700
gggacccaag gaaagctcac cctcactgag gtctcaggac acgggttgtg cataggaaag   2760
gtgcccttta cccatcagca tctctgcaat cagaccctat ccatcaattc ctccggagac   2820
catcagtatc tgctcccctc caaccatagc tggtgggctt gcagcactgg cctcacccct   2880
tgcctctcca cctcagtttt taatcagact agagatttct gtatccaggt ccagctgatt   2940
cctcgcatct attactatcc tgaagaagtt ttgttacagg cctatgacaa ttctcacccc   3000
aggactaaaa gagaggctgt ctcacttacc ctagctgttt tactgggggtt gggaatcacg   3060
gcgggaatag gtactggttc aactgcctta attaaaggac ctatagacct ccagcaaggc   3120
ctgacaagcc tccagatcgc catagatgct gacctccggg ccctccaaga ctcagtcagc   3180
```

-continued

```
aagttagagg actcactgac ttccctgtcc gaggtagtgc tccaaaatag gagaggcctt      3240
gacttgctgt ttctaaaaga aggtggcctc tgtgcggccc taaaggaaga gtgctgtttt      3300
tacatagacc actcaggtgc agtacgggac tccatgaaaa aactcaaaga aaaactggat      3360
aaaagacagt tagagcgcca gaaaagccaa aactggtatg aaggatggtt caataactcc      3420
ccttggttca ctaccctgct atcaaccatc gctgggcccc tattactcct ccttctgttg      3480
ctcatcctcg ggccatgcat catcaatcga ttagttcaat tgttaaaga caggatctca       3540 gtagtccagg ctttagtcct gactcaacaa taccaccagc taaagcctat agagtacgag      3600
ccatagggcg cctagtgttg acaattaatc atcggcatag tatacggcat agtataatac      3660
gactcactat aggagggcca ccatggccaa gttgaccagt gccgttccgg tgctcaccgc      3720
gcgcgacgtc gccggagcgg tcgagttctg gaccgaccgg ctcgggttct cccgggactt      3780
cgtggaggac gacttcgccg tgtggtccgg ggacgacgtg accctgttca tcagcgcggt      3840
ccaggaccag gtggtgccgg acaacaccct ggcctgggtg tgggtgcgcg gcctggacga      3900
gctgtacgcc gagtggtcgg aggtcgtgtc cacgaacttc cgggacgcct ccgggccggc      3960
catgaccgag atcggcgagc agccgtgggg gcgggagttc gccctgcgcg acccggccgg      4020
caactgcgtg cacttcgtgg ccgaggagca ggactgannn ncggaccggt cgacttgtta      4080
acttgtttat tgcagcttat aatggttaca aataaagcaa tagcatcaca aatttcacaa      4140
ataaagcatt ttttcactg cattctagtt gtggtttgtc caaactcatc aatgtatctt       4200
atcatgtctg gatccagatc tgggcccatg cggccgcgga tcgatnnnna catgtgagca      4260
aaaggccagc aaaaggccag gaaccgtaaa aaggccgcgt tgctggcgtt tttccatagg      4320
ctccgccccc ctgacgagca tcacaaaaat cgacgctcaa gtcagaggtg gcgaaacccg      4380
acaggactat aaagatacca ggcgtttccc cctggaagct ccctcgtgcg ctctcctgtt      4440
ccgaccctgc cgcttaccgg atacctgtcc gcctttctcc cttcgggaag cgtggcgctt      4500
tctcaatgct cacgctgtag gtatctcagt tcggtgtagg tcgttcgctc caagctgggc      4560
tgtgtgcacg aaccccccgt tcagcccgac cgctgcgcct tatccggtaa ctatcgtctt      4620
gagtccaacc cggtaagaca cgacttatcg ccactggcag cagccactgg taacaggatt      4680
agcagagcga ggtatgtagg cggtgctaca gagttcttga agtggtggcc taactacggc      4740
tacactagaa ggacagtatt tggtatctgc gctctgctga agccagttac cttcggaaaa      4800
agagttggta gctcttgatc cggcaaacaa accaccgctg gtagcggtgg tttttttgtt      4860
tgcaagcagc agattacgcg cagaaaaaaa ggatctcaag aagatccttt gatcttttct      4920
acggggtctg acgctcagtg gaacgaaaac tcacgttaag ggattttggt catgagatta      4980
tcaaaaagga tcttcaccta gatcctttta aattaaaaat gaagttttaa atcaatctaa      5040
agtatatatg agtaaacttg gtctgacagt taccaatgct taatcagtga ggcacctatc      5100
tcagcgatct gtctatttcg ttcatccata gttgcctgac tccccgtcgt gtagataact      5160
acgatacggg agggcttacc atctggcccc agtgctgcaa tgataccgcg agacccacgc      5220
tcaccggctc cagatttatc agcaataaac cagccagccg aagggccga gcgcagaagt       5280 ggtcctgcaa ctttatccgc ctccatccag tctattaatt gttgccggga agctagagta      5340
agtagttcgc cagttaatag tttgcgcaac gttgttgcca ttgctacagg catcgtggtg      5400
tcacgctcgt cgtttggtat ggcttcattc agctccggtt cccaacgatc aaggcgagtt      5460
acatgatccc ccatgttgtg caaaaaagcg gttagctcct tcggtcctcc gatcgttgtc      5520
```

```
agaagtaagt tggccgcagt gttatcactc atggttatgg cagcactgca taattctctt    5580
actgtcatgc catccgtaag atgcttttct gtgactggtg agtactcaac caagtcattc    5640
tgagaatagt gtatgcggcg accgagttgc tcttgcccgg cgtcaatacg ggataatacc    5700
gcgccacata gcagaacttt aaaagtgctc atcattggaa aacgttcttc ggggcgaaaa    5760
ctctcaagga tcttaccgct gttgagatcc agttcgatgt aacccactcg tgcacccaac    5820
tgatcttcag catcttttac tttcaccagc gtttctgggt gagcaaaaac aggaaggcaa    5880
aatgccgcaa aaaagggaat aagggcgaca cggaaatgtt gaatactcat actcttcctt    5940
tttcaatatt attgaagcat ttatcagggt tattgtctca tgagcggata catatttgaa    6000
tgtatttaga aaataaaca aatagggqtt ccgcgcacat ttccccgaaa agtgccacct    6060
gacgtctaag aaaccattat tatcatgaca ttaacctata aaaataggcg tatcacgagg    6120
ccctttcgtc tcgcgcgttt cggtgatgac ggtgaaaacc tctgacacat gcagctcccg    6180
gagacggtca cagcttgtct gtaagcggat gccgggagca gacaagcccg tcagggcgcg    6240
tcagcgggtg ttggcgggtg tcggggctgg cttaactatg cggcatcaga gcagattgta    6300
ctgagagtgc ac                                                        6312
```

<210> SEQ ID NO 8
<211> LENGTH: 5865
<212> TYPE: DNA
<213> ORGANISM: Artificial Sequence
<220> FEATURE:
<223> OTHER INFORMATION: Description of Artificial Sequence: Portion of
      construct
<220> FEATURE:
<221> NAME/KEY: misc_feature
<222> LOCATION: (3611)
<223> OTHER INFORMATION: n is any nucleotide
<220> FEATURE:
<221> NAME/KEY: misc_feature
<222> LOCATION: (3612)
<223> OTHER INFORMATION: n is any nucleotide
<220> FEATURE:
<221> NAME/KEY: misc_feature
<222> LOCATION: (3613)
<223> OTHER INFORMATION: n is any nucleotide
<220> FEATURE:
<221> NAME/KEY: misc_feature
<222> LOCATION: (3614)
<223> OTHER INFORMATION: n is any nucleotide
<220> FEATURE:
<221> NAME/KEY: misc_feature
<222> LOCATION: (3799)
<223> OTHER INFORMATION: n is any nucleotide
<220> FEATURE:
<221> NAME/KEY: misc_feature
<222> LOCATION: (3800)
<223> OTHER INFORMATION: n is any nucleotide
<220> FEATURE:
<221> NAME/KEY: misc_feature
<222> LOCATION: (3801)
<223> OTHER INFORMATION: n is any nucleotide
<220> FEATURE:
<221> NAME/KEY: misc_feature
<222> LOCATION: (3802)
<223> OTHER INFORMATION: n is any nucleotide

<400> SEQUENCE: 8

```
catatgcggt gtgaaatacc gcacagatgc gtaaggagaa aataccgcat caggcgccat      60
tcgccattca ggctgcgcaa ctgttgggaa gggcgatcgg tgcgggcctc ttcgctatta     120
cgccagctgg cgaaaggggg atgtgctgca aggcgattaa gttgggtaac gccagggttt     180
tcccagtcac gacgttgtaa aacgacggcc agtgaattcc gattagttca atttgttaaa     240
```

-continued

```
gacaggatct cagtagtcca ggctttagtc ctgactcaac aataccacca gctaaaacca      300
ctagaatacg agccacaata aataaagat tttatttagt ttccagaaaa agggggaat        360 gaaagacccc accaaattgc ttagcctgat agccgcagta acgccatttt gcaaggcatg      420 gaaaatacc aaaccaagaa tagagaagtt cagatcaagg gcgggtacac gaaaacagct      480
aacgttgggc caaacaggat atctgcggtg agcagtttcg gccccggccc ggggccaaga     540
acagatggtc accgcggttc ggccccggcc cggggccaag aacagatggt ccccagatat    600
ggcccaaccc tcagcagttt cttaagaccc atcagatgtt tccaggctcc cccaaggacc    660
tgaaatgacc ctgtgcctta tttgaattaa ccaatcagcc tgcttctcgc ttctgttcgc    720
gcgcttctgc ttcccgagct ctataaaaga gctcacaacc cctcactcgg cgcgccagtc    780
ctccgataga ctgagtcgcc cgggtacccg tgtatccaat aaatcctctt gctgttgcat    840
ccgactcgtg gtctcgctgt tccttgggag ggtctcctca gagtgattga ctaccgtct     900 cgggggtctt tcatttgggg gctcgtccgg gatctggaga cccctgccca gggaccaccg    960
acccaccacc gggaggtaag ctggccaaga tcccccgggc tgcaggaatt tatgaaatcc   1020
tttatggggg accccccct ttgtcaacct tgctcaattc cttctccccc tccgatccta    1080
agactgattt acaagcccga ctaaaagggc tgcaaggcgt gcaggcccaa atctggacac   1140
ccctggccga attgtaccgg ccaggacatc cacaaactag ccacccattt caggtgggag  1200
actccgtgta cgtccggcgg caccgctctc aaggattgga gcctcgttgg aagggacctt  1260
acatcgtcct gctgaccacg cccaccgcca taaaggttga cgggatcgcc gcctggattc  1320
acgcatcgca cgccaaggca gccccaaaaa cccctggacc agaaactccc aaaacctgga  1380
agctccgccg ttcggagaac cctcttaaga taagactctc ccgtgtctga ctgctaatcc  1440
accttgtccc tgtactaacc caaaatgaaa ctcccaacag gaatggtcat tttatgtagc   1500
ctaataatag ttcgggcagg gtttgacgac ccccgcaagg ctatcgcatt agtacaaaaa  1560
caacatggta aaccatgcga atgcagcgga gggcaggtat ccgaggcccc accgaactcc   1620
atccaacagg taacttgccc aggcaagacg gcctacttaa tgaccaacca aaaatggaaa  1680
tgcagagtca ctccaaaaat ctcacctagc gggggagaac tccagaactg cccctgtaac  1740
actttccagg actcgatgca cagttcttgt tatactgaat accggcaatg caggcgaatt  1800
aataagacat actacacggc caccttgctt aaaatacggt ctgggagcct caacgaggta  1860
cagatattac aaaaccccaa tcagctccta cagtcccctt gtagggctc tataaatcag    1920 cccgtttgct ggagtgccac agcccccatc catatctccg atggtggagg accccctcgat 1980 actaagagag tgtggacagt ccaaaaaagg ctagaacaaa ttcataaggc tatgactcct  2040
gaacttcaat accaccccctt agccctgccc aaagtcagag atgaccttag ccttgatgca  2100
cggacttttg atatcctgaa taccactttt aggttactcc agatgtccaa ttttagcctt   2160
gcccaagatt gttggctctg tttaaaacta ggtaccccta cccctcttgc gatacccact   2220
ccctctttaa cctactccct agcagactcc ctagcgaatc cctcctgtca gattatacct   2280
cccctcttgg ttcaaccgat gcagttctcc aactcgtcct gtttatcttc ccctttcatt   2340
aacgatacgg aacaaataga cttaggtgca gtcacccttta ctaactgcac ctctgtagcc 2400
aatgtcagta gtcctttatg tgccctaaac gggtcagtct tcctctgtgg aaataacatg 2460
gcatacacct atttacccca aaactggacc agactttgcg tccaagcctc cctcctcccc  2520
gacattgaca tcaacccggg ggatgagcca gtccccattc ctgccattga tcattatata 2580
catagaccta aacgagctgt acagttcatc cctttactag ctggactggg aatcaccgca 2640
```

-continued

```
gcattcacca ccggagctac aggcctaggt gtctccgtca cccagtatac aaaattatcc    2700
catcagttaa tatctgatgt ccaagtctta tccggtacca tacaagattt acaagaccag    2760
gtagactcgt tagctgaagt agttctccaa aataggaggg gactggacct actaacggca    2820
gaacaaggag gaatttgttt agccttacaa gaaaaatgct gttttatgc taacaagtca     2880 ggaattgtga gaaacaaaat aagaaccta caagaagaat tacaaaaacg cagggaaagc     2940
ctggcaacca accctctctg gaccgggctg cagggctttc ttccgtacct cctacctctc    3000 ctgggaccc tactcaccct cctactcata ctaaccattg ggccatgcgt tttcagtcgc     3060
ctcatggcct tcattaatga tagacttaat gttgtacatg ccatggtgct ggcccagcaa    3120
taccaagcac tcaaagctga ggaagaagct caggattgag gcgcctagtg ttgacaatta    3180
atcatcggca tagtatacgg catagtataa tacgactcac tataggaggg ccaccatggc    3240
caagttgacc agtgccgttc cggtgctcac gcgcgcgac gtcgccggag cggtcgagtt     3300
ctggaccgac cggctcgggt ctcccggga cttcgtggag gacgacttcg ccggtgtggt    3360
ccgggacgac gtgaccctgt tcatcagcgc ggtccaggac caggtggtgc ggacaacac    3420 cctggcctgg gtgtgggtgc gcggcctgga cgagctgtac gccgagtggt cggaggtcgt    3480
gtccacgaac ttccgggacg cctccgggcc ggccatgacc gagatcggcg agcagccgtg    3540
ggggcgggag ttcgccctgc gcgacccggc cggcaactgc gtgcacttcg tggccgagga    3600
gcaggactga nnnncggacc ggtcgacttg ttaacttgtt tattgcagct tataatggtt    3660
acaaataaag caatagcatc acaaatttca caaataaagc atttttttca ctgcattcta    3720
gttgtggttt gtccaaactc atcaatgtat cttatcatgt ctggatccag atctgggccc    3780
atgcggccgc ggatcgatnn nnacatgtga gcaaaaggcc agcaaaggcc aggaaccgt    3840 aaaaaggccg cgttgctggc gttttccat aggctccgcc ccctgacga gcatcacaaa     3900 aatcgacgct caagtcagag gtggcgaaac ccgacaggac tataaagata ccaggcgttt    3960 cccctggaa gctccctcgt gcgctctcct gttccgaccc tgccgcttac cggatacctg    4020
tccgcctttc tcccttcggg aagcgtggcg ctttctcaat gctcacgctg taggtatctc    4080
agttcggtgt aggtcgttcg ctccaagctg ggctgtgtgc acgaaccccc cgttcagccc    4140
gaccgctgcg ccttatccgg taactatcgt cttgagtcca acccggtaag acacgactta    4200
tcgccactgg cagcagccac tggtaacagg attagcagag cgaggtatgt aggcggtgct    4260
acagagttct tgaagtggtg gcctaactac ggctacacta aaggacagt atttggtatc    4320 tgcgctctgc tgaagccagt taccttcgga aaaagagttg gtagctcttg atccggcaaa    4380
caaaccaccg ctggtagcgg tggtttttt gtttgcaagc agcagattac gcgcagaaaa    4440
aaaggatctc aagaagatcc tttgatcttt tctacgggt ctgacgctca gtggaacgaa    4500
aactcacgtt aagggatttt ggtcatgaga ttatcaaaaa ggatcttcac ctagatcctt    4560
ttaaattaaa aatgaagttt taaatcaatc taaagtatat atgagtaaac ttggtctgac    4620
agttaccaat gcttaatcag tgaggcacct atctcagcga tctgtctatt tcgttcatcc    4680
atagttgcct gactccccgt cgtgtagata actacgatac gggagggctt accatctggc    4740
cccagtgctg caatgatacc gcgagaccca cgctcaccgg ctccagattt atcagcaata    4800
aaccagccag ccggaagggc cgagcgcaga agtggtcctg caactttatc cgcctccatc    4860
cagtctatta attgttgccg ggaagctaga gtaagtagtt cgccagttaa tagtttgcgc    4920
aacgttgttg ccattgctac aggcatcgtg gtgtcacgct cgtcgtttgg tatggcttca    4980
```

-continued

| | |
|---|---|
| ttcagctccg gttcccaacg atcaaggcga gttacatgat cccccatgtt gtgcaaaaaa | 5040 |
| gcggttagct ccttcggtcc tccgatcgtt gtcagaagta agttggccgc agtgttatca | 5100 |
| ctcatggtta tggcagcact gcataattct cttactgtca tgccatccgt aagatgcttt | 5160 |
| tctgtgactg gtgagtactc aaccaagtca ttctgagaat agtgtatgcg gcgaccgagt | 5220 |
| tgctcttgcc cggcgtcaat acgggataat accgcgccac atagcagaac tttaaaagtg | 5280 |
| ctcatcattg gaaaacgttc ttcggggcga aaactctcaa ggatcttacc gctgttgaga | 5340 |
| tccagttcga tgtaacccac tcgtgcaccc aactgatctt cagcatcttt tactttcacc | 5400 |
| agcgtttctg ggtgagcaaa aacaggaagg caaaatgccg caaaaaaggg aataagggcg | 5460 |
| acacggaaat gttgaatact catactcttc cttttcaat attattgaag catttatcag | 5520 |
| ggttattgtc tcatgagcgg atacatattt gaatgtattt agaaaaataa acaaataggg | 5580 |
| gttccgcgca catttccccg aaaagtgcca cctgacgtct aagaaaccat tattatcatg | 5640 |
| acattaacct ataaaaatag gcgtatcacg aggccctttc gtctcgcgcg tttcggtgat | 5700 |
| gacggtgaaa acctctgaca catgcagctc ccggagacgg tcacagcttg tctgtaagcg | 5760 |
| gatgccggga gcagacaagc ccgtcaggc gcgtcagcgg tgttggcgg gtgtcgggc | 5820 |
| tggcttaact atgcggcatc agagcagatt gtactgagag tgcac | 5865 |

<210> SEQ ID NO 9
<211> LENGTH: 3925
<212> TYPE: DNA
<213> ORGANISM: Artificial Sequence
<220> FEATURE:
<223> OTHER INFORMATION: Description of Artificial Sequence: Portion of
      construct
<220> FEATURE:
<221> NAME/KEY: misc_feature
<222> LOCATION: (3910)
<223> OTHER INFORMATION: n is any nucleotide
<220> FEATURE:
<221> NAME/KEY: misc_feature
<222> LOCATION: (3911)
<223> OTHER INFORMATION: n is any nucleotide
<220> FEATURE:
<221> NAME/KEY: misc_feature
<222> LOCATION: (3912)
<223> OTHER INFORMATION: n is any nucleotide
<220> FEATURE:
<221> NAME/KEY: misc_feature
<222> LOCATION: (3913)
<223> OTHER INFORMATION: n is any nucleotide

<400> SEQUENCE: 9

| | |
|---|---|
| agatctcccg atccctatg gtcgactctc agtacaatct gctctgatgc cgcatagtta | 60 |
| agccagtatc tgctccctgc ttgtgtgttg gaggtcgctg agtagtgcgc gagcaaaatt | 120 |
| taagctacaa caaggcaagg cttgaccgac aattgcatga agaatctgct tagggttagg | 180 |
| cgttttgcgc tgcttcgcga tgtacgggcc agatatacgc gttgacattg attattgact | 240 |
| agttattaat agtaatcaat tacggggtca ttagttcata gcccatatat ggagttccgc | 300 |
| gttacataac ttacggtaaa tggcccgcct ggctgaccgc ccaacgaccc ccgcccattg | 360 |
| acgtcaataa tgacgtatgt tcccatagta acgccaatag ggactttcca ttgacgtcaa | 420 |
| tgggtggact atttacggta aactgcccac ttggcagtac atcaagtgta tcatatgcca | 480 |
| agtacgcccc ctattgacgt caatgacggt aaatggcccg cctggcatta tgcccagtac | 540 |
| atgaccttat gggactttcc tacttggcag tacatctacg tattagtcat cgctattacc | 600 |
| atggtgatgc ggttttggca gtacatcaat gggcgtggat agcggtttga ctcacgggga | 660 |

-continued

```
tttccaagtc tccaccccat tgacgtcaat gggagtttgt tttggcacca aaatcaacgg    720
gactttccaa aatgtcgtaa caactccgcc ccattgacgc aaatgggcgg taggcgtgta    780
cggtgggagg tctatataag cagagctctc tggctaacta gagaacccac tgcttaactg    840
gcttatcgaa atgtcgactg agaacttcag ggtgagtttg gggacccttg attgttcttt    900 cttttcgct attgtaaaat tcatgttata tggagggggc aaagttttca gggtgttgtt    960
tagaatggga agatgtccct tgtatcacca tggaccctca tgataatttt gtttctttca    1020 cttctactc tgttgacaac cattgtctcc tcttattttc ttttcatttt ctgtaacttt    1080
ttcgttaaac tttagcttgc atttgtaacg aattttaaa ttcacttttg tttatttgtc    1140
agattgtaag tactttctct aatcactttt ttttcaaggc aatcagggta tattatattg    1200
tacttcagca cagttttaga gaacaattgt tataattaaa tgataaggta gaatatttct    1260
gcatataaat tctggctggc gtggaaatat tcttattggt agaaacaact acatcctggt    1320
catcatcctg cctttctctt tatggttaca atgatataca ctgtttgaga tgaggataaa    1380
atactctgag tccaaaccgg gccctctgc taaccatgtt catgccttct tcttttcct    1440 acagctcctg ggcaacgtgc tggttgttgt gctgtctcat cattttggca aggatcggcc    1500
ggaacagcat caggaccgac atggaaggtc cagcgttctc aaaacccctt aaagataaga    1560
ttaacccgtg gaagtcctta atggtcatgg gggtctattt aagagtaggg atggcagaga    1620 gccccccatca ggtctttaat gtaacctgga gagtcaccaa cctgatgact gggcgtaccg    1680
ccaatgccac ctcccttta ggaactgtac aagatgcctt cccaagatta tattttgatc    1740
tatgtgatct ggtcggagaa gagtgggacc cttcagacca ggaaccatat gtcgggtatg    1800
gctgcaaata ccccggaggg agaaagcgga cccggacttt tgactttac gtgtgccctg    1860 ggcataccgt aaaatcgggg tgtgggggc caagagaggg ctactgtggt gaatggggtt    1920
gtgaaaccac cggacaggct tactggaagc ccacatcatc atgggaccta atctccctta    1980
agcgcggtaa caccccctgg gacacgggat gctccaaaat ggcttgtggc ccctgctacg    2040
acctctccaa agtatccaat tccttccaag gggctactcg aggggcaga tgcaaccctc    2100 tagtcctaga attcactgat gcaggaaaaa aggctaattg ggacgggccc aaatcgtggg    2160
gactgagact gtaccggaca ggaacagatc ctattaccat gttctccctg acccgccagg    2220
tcctcaatat agggccccgc atccccattg ggcctaatcc cgtgatcact ggtcaactac    2280 cccctcccg acccgtgcag atcaggctcc ccaggcctcc tcagcctcct cctacaggcg    2340
cagcctctat agtccctgag actgccccac cttctcaaca acctgggacg ggagacaggc    2400
tgctaaacct ggtagaagga gcctatcagg cgcttaacct caccaatccc gacaagaccc    2460
aagaatgttg gctgtgctta gtgtcgggac ctccttatta cgaaggagta gcggtcgtgg    2520
gcacttatac caatcattct accgccccgg ccagctgtac ggccacttcc caacataagc    2580
ttaccctatc tgaagtgaca ggacagggcc tatgcatggg agcactacct aaaactcacc    2640
aggccttatg taacaccacc caaagtgccg gctcaggatc ctactacctt gcagcacccg    2700
ctggaacaat gtgggcttgt agcactggat tgactccctg cttgtccacc acgatgctca    2760
atctaaccac agactattgt gtattagttg agctctggcc cagaataatt taccactccc    2820
ccgattatat gtatggtcag cttgaacagc gtaccaaata taagagggag ccagtatcgt    2880
tgaccctggc ccttctgcta ggaggattaa ccatgggagg gattgcagct ggaataggga    2940
cggggaccac tgccctaatc aaaacccagc agtttgagca gcttcacgcc gctatccaga    3000
cagacctcaa cgaagtcgaa aaatcaatta ccaacctaga aaagtcactg acctcgttgt    3060
```

```
ctgaagtagt cctacagaac cgaagaggcc tagatttgct cttcctaaaa gagggaggtc    3120
tctgcgcagc cctaaaagaa gaatgttgtt tttatgcaga ccacacggga ctagtgagag    3180
acagcatggc caaactaagg gaaaggctta atcagagaca aaaactattt gagtcaggcc    3240
aaggttggtt cgaagggcag tttaatagat cccctggtt taccacctta atctccacca     3300
tcatgggacc tctaatagta ctcttactga tcttactctt tggaccctgc attctcaatc    3360
gattagttca atttgttaaa gacaggatct cagtagtcca ggctttagtc ctgactcaac    3420
aataccacca gctaaagcct atagagtacg agccataggc cgcctagtgt tgacaattaa    3480
tcatcggcat agtatacggc atagtataat acgactcact ataggagggc caccatggcc    3540
aagttgacca gtgccgttcc ggtgctcacc gcgcgcgacg tcgccggagc ggtcgagttc    3600
tggaccgacc ggctcgggtt ctcccgggac ttcgtggagg acgacttcgc cggtgtggtc    3660
cgggacgacg tgaccctgtt catcagcgcg gtccaggacc aggtggtgcc ggacaacacc    3720
ctggcctggg tgtgggtgcg cggcctggac gagctgtacg ccgagtggtc ggaggtcgtg    3780
tccacgaact tccgggacgc ctccgggccg gccatgacca gatcggcga gcagccgtgg     3840 gggcgggagt tcgccctgcg cgacccggcc ggcaactgcg tgcacttcgt ggccgaggag    3900
caggactgan nncggaccg gtcga                                           3925

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
cggaattcgg atccgagctc ggcccagccg gccaccatga aaacatttaa catttctc       58

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
gatccatcga taagcttggt ggtaaaactt tt                                   32

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
gctcttcgga ccctgcattc                                                 20

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide
```

<400> SEQUENCE: 13
tagcatggcg ccctatggct cgtactctat aggc                             34

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
cgcctcatgg ccttcattaa                                             20

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 15
tagcatggcg cctcaatcct gagcttcttc c                                31

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
tctcgcttct gttcgcgcgc                                             20

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 17
tcgatcaagc ttgcggccgc ggtggtgggt cggtggtcc                        39

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 18
ctctggctca cagtacgacg tag                                         23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 19
ccatcaatcc ggtaggtttt ccg                                         23

<210> SEQ ID NO 20
<211> LENGTH: 23

```
<212> TYPE: DNA
<213> ORGANISM: Artificial Sequence
<220> FEATURE:
<223> OTHER INFORMATION: Description of Artificial Sequence: Primer

<400> SEQUENCE: 20
carrgkttca araacwsycc cac                                           23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: misc_feature
<222> LOCATION: (12)
<223> OTHER INFORMATION: n is any nucleotide

<400> SEQUENCE: 21
agyarvgtag cngggtthag g                                             21

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 22
tccccttgga atactcctgt tttygt                                        26

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 23
cattccttgt ggtaaaactt tccaytg                                       27

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
cctcaccctg atcacryttg                                               20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
gaattatgtc tgacagaagg g                                             21

<210> SEQ ID NO 26
<211> LENGTH: 23
<212> TYPE: DNA
<213> ORGANISM: Artificial Sequence
<220> FEATURE:
```

-continued

```
<223> OTHER INFORMATION: Description of Artificial Sequence: Primer

<400> SEQUENCE: 26
gttgacatct gcagagaaag acc                                          23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 27
tctgaggtct gtacacacaa tgg                                          23

<210> SEQ ID NO 28
<211> LENGTH: 167
<212> TYPE: DNA
<213> ORGANISM: Artificial Sequence
<220> FEATURE:
<223> OTHER INFORMATION: Description of Artificial Sequence: Portion of
      construct

<400> SEQUENCE: 28
tctagactga catggcgcgt tcaacgctct caaaacccct taaaaataag gttaacccgc    60
gaggccccct aatcccctta attcttctga tgctcagagg ggtcagtact gcttcgcccg   120
gctccagtgc ggcccagccg gccaccatga aaacatttaa catttct                167

<210> SEQ ID NO 29
<211> LENGTH: 103
<212> TYPE: DNA
<213> ORGANISM: Artificial Sequence
<220> FEATURE:
<223> OTHER INFORMATION: Description of Artificial Sequence: Portion of
      construct

<400> SEQUENCE: 29
tacgagccat agggcgccta gtgttgacaa ttaatcatcg gcatagtata cggcatagta    60
taatacgact cactatagga gggccaccat ggccaagttg acc                    103
```